US012655409B2

(12) United States Patent
Díez Martínez et al.

(10) Patent No.: US 12,655,409 B2
(45) Date of Patent: Jun. 16, 2026

(54) RECOMBINANT LYSIN AND ITS USE IN THE TREATMENT OF GRAM-NEGATIVE BACTERIAL INFECTIONS

(71) Applicant: TELUM THERAPEUTICS S.L., Noáin (ES)

(72) Inventors: Roberto Díez Martínez, Noáin (ES); María Morales Areizaga, Noáin (ES)

(73) Assignee: TELUM THERAPEUTICS S.L., Noáin (ES)

( * ) Notice: Subject to any disclaimer, the term of this patent is extended or adjusted under 35 U.S.C. 154(b) by 572 days.

(21) Appl. No.: 17/910,688

(22) PCT Filed: Mar. 11, 2021

(86) PCT No.: PCT/EP2021/056264
§ 371 (c)(1),
(2) Date: Sep. 9, 2022

(87) PCT Pub. No.: WO2021/180892
PCT Pub. Date: Sep. 16, 2021

(65) Prior Publication Data
US 2023/0138922 A1 May 4, 2023

(30) Foreign Application Priority Data

Mar. 11, 2020 (EP) ..................................... 20382177
Mar. 31, 2020 (EP) ..................................... 20382254

(51) Int. Cl.
*C12N 9/36* (2006.01)
*C12N 9/80* (2006.01)
(52) U.S. Cl.
CPC .............. *C12N 9/2462* (2013.01); *C12N 9/80* (2013.01); *C12Y 302/01017* (2013.01); *C12Y 305/01028* (2013.01)
(58) Field of Classification Search
None
See application file for complete search history.

(56) References Cited

FOREIGN PATENT DOCUMENTS

| | | |
|---|---|---|
| EP | 3607062 A1 | 2/2020 |
| RU | 2614114 C2 | 3/2017 |
| WO | 2010002959 A2 | 1/2010 |
| WO | 2010149792 A2 | 12/2010 |
| WO | 201123702 A1 | 3/2011 |
| WO | 2012059545 A1 | 5/2012 |
| WO | 2015200783 A2 | 12/2015 |
| WO | 201749233 A2 | 3/2017 |
| WO | WO-2018185634 A1 * | 10/2018 ........... C12N 9/2462 |

OTHER PUBLICATIONS

Tikhe et al. NCBI sequence search SEQ ID No. 1. Submitted on Sep. 23, 2016. Downloaded on Dec. 2, 2024. Retrieved from: <https://blast.ncbi.nlm.nih.gov/Blast.cgi?PROGRAM=blastp&PAGE_TYPE=BlastSearch&BLAST_SPEC=&LINK_LOC=blasttab&LAST_PAGE=blastn> pp. 1-3 (Year: 2016).*
Schmelcher, M. et al. 2012. Bacteriophage endolysins as novel antimicrobials. Future Microbiology 7(10): 1147-1171; specif. p. 1147 (Year: 2012).*
Tikhe, C.V. et al. 2018. Whole-genome sequence of novel Enterobacter bacteriophage Arya with an integrase pseudogene, isolated from the gut of the *Formosan subterranean* termite. American Society for Microbiology—Genome Announcements 6(1): pp. 1-2; specif. pp. 1, 2 (Year: 2018).*
Morita, M. et al. 2001a. Antibacterial activity of Bacillus amyloliquefaciens phage endolysin without holin conjugation. Journal of Bioscience and Bioengineering 91(5): 469-473; specif. pp. 469, 472, 473 (Year: 2001).*
Morita, M. et al. 2001b. Functional analysis of antibacterial activity of Bacillus amyloliquefaciens phage endolysin against gram-negative bacteria. FEBS Letters 500: 56-59; specif. pp. 56, 58 (Year: 2001).*
Wang, S. et al. 2017. The antibacterial activity of *E. coli* bacteriophage lysin lysep3 is enhanced by fusing the Bacillus amyloliquefaciens bacteriophage endolysin binding domain D8 to the C-terminal region. Journal of Microbiology 55(5): 403-408; specif. pp. 403, 404, 406, 407 (Year: 2017).*
Betts, M.J. et al. Amino acid properties and consequences of substitutions. In.: Bioinformatics for Geneticists. Chapter 14. Eds.: M.R. Barnes; I.C. Gray. Copyright 2003. John Wiley & Sons, Ltd.; pp. 289-316; specif. p. 312 (Year: 2003).*
GenBank search. KX231828.1. Genome sequence of Enterobacter phage Arya as deposited by Tikhe et al. Annotated on Dec. 7, 2017. Downloaded from: < https://www.ncbi.nlm.nih.gov/nuccore/KX231828> Retrieved on: Apr. 8, 2025. pp. 1-2; specif. p. 2 (Year: 2017).*
NCBI sequence search. SEQ ID No. 1. Retrieved from: <https://https://blast.ncbi.nlm.nih.gov/Blast.cgi?PROGRAM=blastp&PAGE_TYPE=BlastSearch&BLAST_SPEC=&LINK_LOC=blasttab&LAST_PAGE=blastn; Downloaded on: Dec. 2, 2024; pp. 1-3 (Year: 2024).*
NCBI sequence search. SEQ ID No. 2. Downloaded on Aug. 5, 2025. Retrieved from: <https://blast.ncbi.nlm.nih.gov/Blast.cgi?PROGRAM=blastp&PAGE_TYPE=BlastSearch&LINK_LOC=blasthome>, pp. 1-4 (Year: 2025).*
Becker et al., "LysK CHAP endopeptidase domain is required for lysis of live staphylococcal cells," *FEMS Microbiology Letters* 294(1):52-60, Mar. 2009.
Briers et al., "Art-175 is a Highly Efficient Antibacterial against Multidrug-Resistant Strains and Persisters of *Pseudomonas aeruginosa,*" *Antimicrobial Agents and Chemotherapy* 58(7):3774-3784, Jul. 2014.
Briers et al., "Engineered Endolysin-Based 'Artilysins' to Combat Multidrug-Resistant Gram-Negative Pathogens," *American Society for Microbiology Journals* 5(4), Jul. 2014, 10 pages.

(Continued)

*Primary Examiner* — Louise W Humphrey
*Assistant Examiner* — Sharon M. Papciak
(74) *Attorney, Agent, or Firm* — Seed Intellectual Property Law Group LLP

(57) ABSTRACT

The present invention relates to a recombinant lysin and its use as antimicrobial agent in new treatment approaches for eliminating antibiotic resistant Gram-negative bacteria, and minimizing the emergence of new resistances. It further concerns polynucleotides encoding the recombinant lysin of the invention, vectors and host cells comprising the same, as well as related methods, medical uses, compositions and kits.

21 Claims, 30 Drawing Sheets

Specification includes a Sequence Listing.

(56) References Cited

OTHER PUBLICATIONS

Czaplewski et al., "Alternatives to antibiotics-a pipeline portfolio review," *The Lancet Infectious Diseases* 16(2), https://doi.org/10.1016/S1473-3099(15)00466-1, Jan. 2016, 24 pages.

Davies et al., "Origins and Evolution of Antibiotic Resistance," *Microbiology and Molecular Biology Reviews* 74(3):417-433, Sep. 2010.

European Centre for Disease Prevention and Control, "Surveillance of antimicrobial resistance in Europe 2018: Annual report of the European Antimicrobial Resistance Surveillance Network (EARS-Net)," DOI: 10.2900/22212, Nov. 2019, 110 pages.

Frankel et al., "Chapter One: Magneto-Aerotaxis," *Magnetoreception and Magnetosomes in Bacteria*, part of the Microbiology Monographs book series vol. 3, DOI 10.1007/7171_2006_036, Sep. 2006, 4 pages.

Hermoso et al., "Taking aim on bacterial pathogens: from phage therapy to enzybiotics," *Current Opinion in Microbiology* 10(5):461-472, Sep. 2007.

Heselpoth et al., "Lysocins: Bioengineered Antimicrobials That Deliver Lysins across the Outer Membrane of Gram-Negative Bacteria," *Antimicrobial Agents and Chemotherapy* 63(6), https://doi.org/10.1128/AAC.00342-19, Jun. 2019, 14 pages.

Hojckova et al., "phiBIOTICS: catalogue of therapeutic enzybiotics, relevant research studies and practical applications," *BMC Microbiology* 13(53), https://doi.org/10.1186/1471-2180-13-53, Mar. 2013, 6 pages.

Lekshmi et al., "The Food Production Environment and the Development of Antimicrobial Resistance in Human Pathogens of Animal Origin," *Microorganisms* 5(11), doi:10.3390/microorganisms5010011, Mar. 2017, 15 pages.

Lood et al., "Novel Phage Lysin Capable of Killing the Multidrug-Resistant Gram-Negative Bacterium *Acinetobacter baumannii* in a Mouse Bacteremia Model," *Antimicrobial Agents and Chemotherapy* 59(4):1983-1991, Apr. 2015.

McCullers et al., "Novel Strategy to Prevent Otitis Media Caused by Colonizing *Streptococcus pneumoniae*," *PLoS Pathogens* 3(3), doi:10.1371/journal.ppat.0030028, Mar. 2007, 3 pages.

O'Neill, "Tackling Drug-Resistant Infections Globally: Final Report and Recommendations," *The Review on Antimicrobial Resistance*, commissioned by the UK Prime Minister, May 2016, 84 pages.

Pires et al., "Genetically Engineered Phages: a Review of Advances over the Last Decade," *Microbiology and Molecular Biology Reviews* 80(3):523-543, Sep. 2016.

Schmelcher et al., "Domain shuffling and module engineering of *Listeria* phage endolysins for enhanced lytic activity and binding affinity," *Microbial Biotechnology* 4(5):651-662, doi:10.1111/j.1751-7915.2011.00263.x, Mar. 2011.

Schmelcher et al., "Bacteriophage endolysins as novel antimicrobials," *Future Microbiology* 7(10), doi:10.2217/fmb.12.97, Oct. 2012, 35 pages.

Vaara, "Agents That Increase the Permeability of the Outer Membrane," *Microbiological Reviews* 56(3):395-411, Sep. 1992.

World Health Organization, "The world health report 2007: a safer future: global public health security in the 21st century," ISBN 978 92 4 156344 4, Dec. 2007, 96 pages.

Yang et al., "Antibacterial Activity of a Novel Peptide-Modified Lysin Against *Acinetobacter baumannii* and *Pseudomonas aeruginosa*," *Frontiers in Microbiology* 6, Article 1471, https://doi.org/10.3389/fmicb.2015.01471, Dec. 2015, 9 pages.

Studier, "Protein production by auto-induction in high density shaking cultures," Protein Expr. Purif. 41(1):207-234, 2005. (28 pages).

Sun et al., "Regulation of a muralytic enzyme by dynamic membrane topology," Nat. Struct. Mol. Biol. 16 (11):1192-1194, 2009. (6 pages).

Sykilinda et al., "Structure of an Acinetobacter Broad-Range Prophage Endolysin Reveals a C-Terminal α-Helix with the Proposed Role in Activity against Live Bacterial Cells," Viruses 10(6):309, 2018. (13 pages).

Taheri-Anganeh et al. "LytU-SH3b fusion protein as a novel and efficient enzybiotic against methicillin-resistant *Staphylococcus aureus*," Molecular biology research communications 8(4):151-158, 2019. (8 pages).

Tenover et al., "Mechanisms of antimicrobial resistance in bacteria," Am. J. Infect. Control 34:S3-S10, 2006. (8 pages).

Vázquez et al., "Csl2, a novel chimeric bacteriophage lysin to fight infections caused by *Streptococcus suis*, an emerging zoonotic pathogen," Sci Rep. 7(1):16506, 2017. (13 pages).

Vázquez et al., "Phage Lysins for Fighting Bacterial Respiratory Infections: A New Generation of Antimicrobials," Front. Immunol. 9:2252, 2018. (12 pages).

Waterhouse et al., "Swiss-Model: homology modelling of protein structures and complexes," Nucleic Acids Res. 46 (W1):W296-W303, 2018. (8 pages).

Wong et al., "An intermolecular binding mechanism involving multiple LysM domains mediates carbohydrate recognition by an endopeptidase," Acta Cryst. D71:592-605, 2014. (14 pages).

World Health Organization, "The World is Running Out of Antibiotics, WHO Report Confirms," accessed at: http://www.who.int/mediacentre/news/releases/2017/running-out-antibiotics/en/, 2017. (3 pages).

Xu et al., "Disulfide Isomerization After Membrane Release of Its SAR Domain Activates P1 Lysozyme," Science 307:113-117, 2005. (6 pages).

Yang et al., "A chimeolysin with extended-spectrum streptococcal host range found by an induced lysis-based rapid screening method," Sci. Rep. 5:17257, 2015. (12 pages).

Yang et al., "Antibiofilm activities of a novel chimeolysin against *Streptococcus* mutans under physiological and cariogenic conditions," Antimicrob. Agents Chemother. 60(12):7436-7443, 2016. (8 pages).

Yoong et al., "Identification of a Broadly Active Phage Lytic Enzyme with Lethal Activity against Antibiotic-Resistant *Enterococcus faecalis* and *Enterococcus faecium*," J Bacteriol. 186(14):4808-4812, 2004. (5 pages).

Zimmer et al. "The Murein Hydrolase of the Bacteriophage φ3626 Dual Lysis System is Active against All Tested *Clostridium perfringens* Strains," Appl. Environ. Microbiol. 68(11):5311-5317, 2002. (7 pages).

Adeyi et al., "Drug-Resistant Infections: A Threat to Our Economic Future," Final Report; World Bank Group: Washington, DC, USA, 2017. (172 pages).

Antilles et al., "Analysis of antimicrobial resistance in *Escherichia coli* strains isolated from poultry in Spain from 1998 to 2013," English translation, pp. 1-9. (27 pages), 2013.

Babu et al., "The structure of DLP12 endolysin exhibiting alternate loop conformation and comparative analysis with other endolysins," Proteins 86(2):210-217, Nov. 2017. (24 pages).

Becker et al., "Differentially conserved staphylococcal SH3b_5 cell wall binding domains confer increased staphylolytic and streptolytic activity to a streptococcal prophage endolysin domain," Gene 443:32-41, 2009.

Briers et al., "Breaking barriers: expansion of the use of endolysins as novel antibacterials against Gram-negative bacteria," Future Microbiology 10(3):377-390, 2015. (4 pages).

Cani et al., "The Role of the Gut Microbiota in Energy Metabolism and Metabolic Disease," Curr Pharm Des. 15:1546-1558, 2009. (13 pages).

Cheng et al., "Removal of Group B Streptococci Colonizing the Vagina and Oropharynx of Mice with a Bacteriophage Lytic Enzyme," Antimicrob. Agents Chemother. 49(1):111-117, 2005. (7 pages).

Claus et al., "Colonization-Induced Host-Gut Microbial Metabolic Interaction," Mol Bio. 2:e00271-e00210, 2011. (8 pages).

Daopin et al., "Structural and Thermodynamic Analysis of the Packing of Two Alpha-Helices in Bacteriophage T4 Lysozyme," J Mol Biol 221:647-667, 1991. (21 pages).

David et al., "Effects of acetaminophen (paracetamol) in the embryonic development of zebrafish, *Danio rerio*," J Appl Toxicol. 7:597-602, 2009. (6 pages).

Díez-Martínez et al., "A novel chimeric phage lysin with high in vitro and in vivo bactericidal activity against *Streptococcus pneumoniae*," J. Antimicrob. Chemother. 70:1763-1773, 2015. (11 pages).

(56) References Cited

OTHER PUBLICATIONS

Düring et al., "The non-enzymatic microbicidal activity of lysozymes" FEBS Lett. 449:93-100, 1999. (8 pages).

Farber, "Antibiotics in Food Preservation," Annu. Rev. Microbiol. 13:125, 1959. (1 page).

Fischetti et al., "Reinventing phage therapy: are the parts greater than the sum?" Nat. Biotechnol. 24:1508-1511, 2006. (4 pages).

D'Costa Frankel et al., "Sampling the Antibiotic Resistome," Science 311:374-378, 2006. (5 pages).

GenPept, "putative endolysin [Enterobacter phage Arya]," NCBI Reference Sequence: YP_009284326.1, accessed online at: https://www.ncbi.nlm.nih.gov/protein/1070100424?sat=48&satkey=135615780. (2 pages), 2025.

Hawkey et al., "Treatment of infections caused by multidrug-resistant Gram-negative bacteria: report of the British Society for Antimicrobial Chemotherapy/Healthcare Infection Society/British Infection Association Joint Working Party," Journal of Antimicrobial Chemotherapy 73(3):iii2-iii78, 2018. (78 pages).

Hooper et al., "Interactions between the microbiota and the immune system," Science 336(6086):1268-1273, 2012. (16 pages).

Huttner et al., "The development and early clinical testing of the ExPEC4V conjugate vaccine against uropathogenic *Escherichia coli.*," Clin Microbiol Infect. 24(10):1046-1050, 2018. (5 pages).

Kelley et al., "The Phyre2 web portal for protein modeling, prediction and analysis," Nat Protoc. 10(6):845-58, Jun. 2015. (28 pages).

Kuroki et al., "Structural basis of the conversion of T4 lysozyme into a transglycosidase by reengineering the active site," Proc Natl Acad Sci USA 96:8949-8954, 1999. (6 pages).

Kuroki et al., "Structure-based design of a lysozyme with altered catalytic activity," Nat. Struct. Biol. 2:1007-1011, 1995. (5 pages).

Le Roy et al., "Antibiotic treatment triggers gut dysbiosis and modulates metabolism in a chicken model of gastro- intestinal infection," BMC Vet Res. 25(1):37, 2019. (13 pages).

Letrado et al., "Bactericidal synergism between antibiotics and phage endolysin Cpl-711 to kill multidrug-resistant pneumococcus," Future Microbiol. 13(11):1215-1223, 2018. (10 pages).

Ley et al., "Microbial ecology: human gut microbes associated with obesity," Nature 444:1022, 2006. (3 pages).

Lim et al., "Exogenous Lytic Activity of SPN9CC Endolysin Against Gram-Negative Bacteria," J. Microbiol. Biotechnol. 24(6):803-811, 2014. (9 pages).

Loessner et al., "C-terminal domains of *Listeria monocytogenes* bacteriophage murein hydrolases determine specific recognition and high-affinity binding to bacterial cell wall carbohydrates," Mol. Microbiol. 44:335-349, 2002.

Maciejewska et al., "Modular endolysin of Burkholderia AP3 phage has the largest lysozyme-like catalytic subunit discovered to date and no catalytic aspartate residue," Sci Rep. 7(1):14501, 2017. (12 pages).

Marine Microbial Engineering (English translation), eds. Haijin et al., China Marine University Press, 1st edition, Jul. 2016, p. 177, 2016. (8 pages).

Minogue et al., "Complete Genome Assembly of *Escherichia coli* ATCC 25922, a Serotype O6 Reference Strain," Genome Announc. 2(5):e00969-14, 2014. (2 pages).

Moody, "Synergism testing: broth microdilution checkerboard and broth macrodilution methods," Clinical Microbiology Procedures Handbook. American Society for Microbiology; DCUSA: 1992. (23 pages).

Nelson et al., "Endolysins as Antimicrobials," Adv Virus Res. 83:299-365, 2012. (67 pages).

Nelson et al., "Prevention and elimination colonization of mice by group A streptococci by using a bacteriophage lytic enzyme," Proc. Natl. Acad. Sci. USA. 98:4107-4112, 2001. (6 pages).

OECD Guidelines for Testing of Chemicals: Fish Embryo Acute Toxicity (FET) Test, Test Guideline No. 236, Jun. 2025. (25 pages).

Orito et al., "Bacillus amyloliquefaciens phage endolysin can enhance permeability of Pseudomonas aeruginosa outer membrane and induce cell lysis," Appl Microbiol Biotechnol. 65(1):105-109, 2004. (5 pages).

Pettersen et al., "UCSF Chimera—A Visualization System for Exploratory Research and Analysis," J. Comput. Chem. 25:1605-1612, 2004. (8 pages).

Pires et al., "Bacteriophage-encoded depolymerases: their diversity and biotechnological applications," Appl. Microbiol. Biotechnol. 100:2141-2151, 2016. (11 pages).

Proietti et al., "Bacterial counts and characterization of intestinal flora in organic and conventional chickens," World's Poultry Science Association (WPSA), Beekbergen, the Netherlands, 2006. (7 pages).

Rennell et al., "Systematic Mutation of Bacteriophage T4 Lysozyme," J Mol Biol 222:67-88, 1991.

Reuter et al. "Approaches to optimize therapeutic bacteriophage and bacteriophage-derived products to combat bacterial infections," Virus Genes 56(2):136-149, 2020. (4 pages).

Santin et al., "Measure of Peptidoglycan Hydrolase Activity," Methods Mol Biol. 1615: 151-158, 2017. (8 pages).

São-José, "Engineering of Phage-Derived Lytic Enzymes: Improving Their Potential as Antimicrobials," Antibiotics 7:29, 2018. (31 pages).

Schmelcher et al., "Rapid Multiplex Detection and Differentiation of Listeria Cells by Use of Fluorescent Phage Endolysin Cell Wall Binding Domains," Appl. Environ. Microbiol. 76(17):5745-5756, 2010. (12 pages).

Schulfer et al., "Intergenerational transfer of antibiotic-perturbed microbiota enhances colitis in susceptible mice," Nat Microbiol. 3:234, 2018. (20 pages).

Smith et al., "Quinolone-resistant *Campylobacter jejuni* infections in Minnesota, 1992-1998. Investigation Team," N. Engl. J. Med. 340:1525-1532, 1999. (8 pages).

Spor et al., "Unravelling the effects of the environment and host genotype on the gut microbiome," Nat Rev Microbiol 9:279, 2011. (13 pages).

Starrels et al. "Populations at Risk Patterns and Determinants of Inappropriate Antibiotic Use in Injection Drug Users," J. Gen. Intern. Med. 24:263-269, 2009. (7 pages).

Masi et al., "Mechanisms of envelope permeability and antibiotic influx and efflux in Gram-negative bacteria," Nat Microbiol 2(17001):1-7, Feb. 2017. (7 pages).

Mooers et al., "Extension to 2268 atoms of direct methods in the ab initio determination of the unknown structure of bacteriophage P22 lysozyme," Acta Cryst. D62:165-176, 2006. (12 pages).

Pillai et al., "Chapter 9: Antimicrobial combinations," Antibiotics in Laboratory Medicine, V. Lorian (eds.), The Williams & Wilkins Co., p. 365-440, 1996. (76 pages).

* cited by examiner

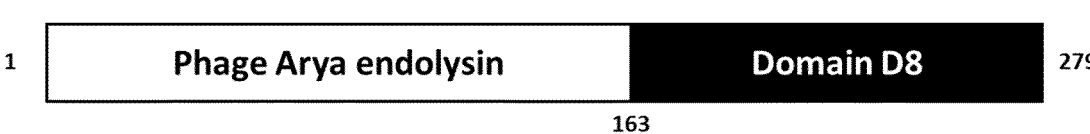

1 | Phage Arya endolysin | Domain D8 | 279
163

MKTSPNGIAVTKYFESFEARAYPDPATGGKPYTIGFGTTVYPSGAPVRLGDVCTKEQAEKYLQNDLAKF
EKIVSDAVRVPLNQGQFDALVSFTYNLGPANLRSSTLLKKLNAGDYAGAAKEFPRWNRANGKVMKGLTR
RRAAEQCLFEGMGGASAIERGVAAANSGTPKNVSRGTSSTKTTPKYKVKNGDNLTKIAKKHNTTVATLL
KLNPGIKDPNMIRVGQTLNVTGSGGKTHKVKSGDTLSKIAVDNKTTVSKLMNLNPEITNPNHIKVGQTI
RLS

B)

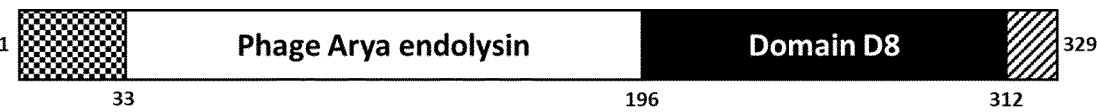

1 | | Phage Arya endolysin | Domain D8 | | 329
33                                    196                        312 amino acids provided by the plasmid

MKETAAAKFERQHMDSPDLGTLVPRGSMAISDPMKTSPNGIAVTKYFESFEARAYPDPATGGKPYTIGF
GTTVYPSGAPVRLGDVCTKEQAEKYLQNDLAKFEKIVSDAVRVPLNQGQFDALVSFTYNLGPANLRSST
LLKKLNAGDYAGAAKEFPRWNRANGKVMKGLTRRRAAEQCLFEGMGGASAIERGVAAANSGTPKNVSRG
TSSTKTTPKYKVKNGDNLTKIAKKHNTTVATLLKLNPGIKDPNMIRVGQTLNVTGSGGKTHKVKSGDTL
SKIAVDNKTTVSKLMNLNPEITNPNHIKVGQTIRLSLGTLVPRGSLEHHHHHH amino acids provided by the plasmid

C)

1 | Phage Arya endolysin | 163

MKTSPNGIAVTKYFESFEARAYPDPATGGKPYTIGFGTTVYPSGAPVRLGDVCTKEQAEKYLQNDLAKF
EKIVSDAVRVPLNQGQFDALVSFTYNLGPANLRSSTLLKKLNAGDYAGAAKEFPRWNRANGKVMKGLTR
RRAAEQCLFEGMGGASAIERGVAAA

FIG. 4
A
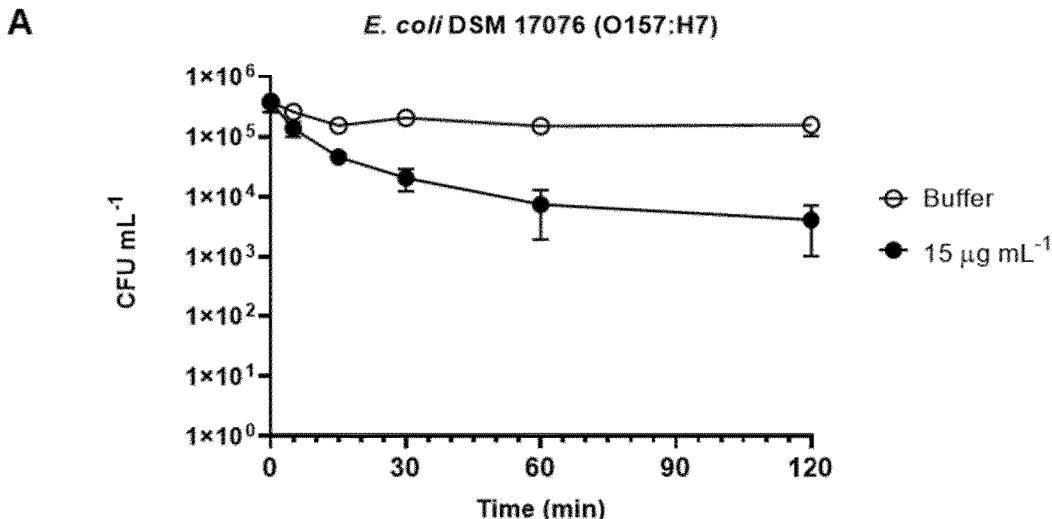
B
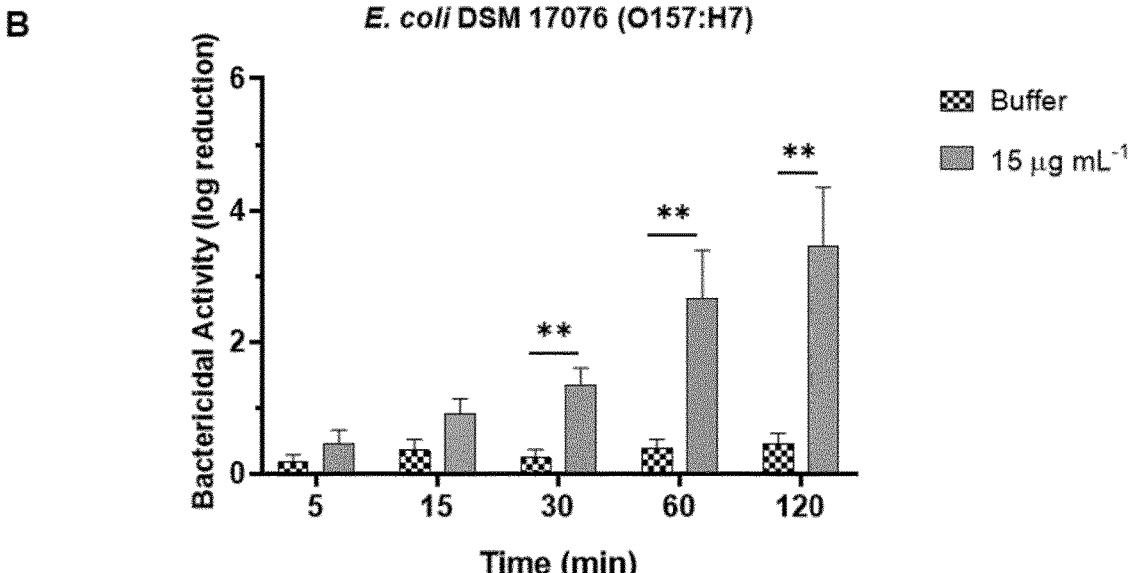

FIG. 5
A
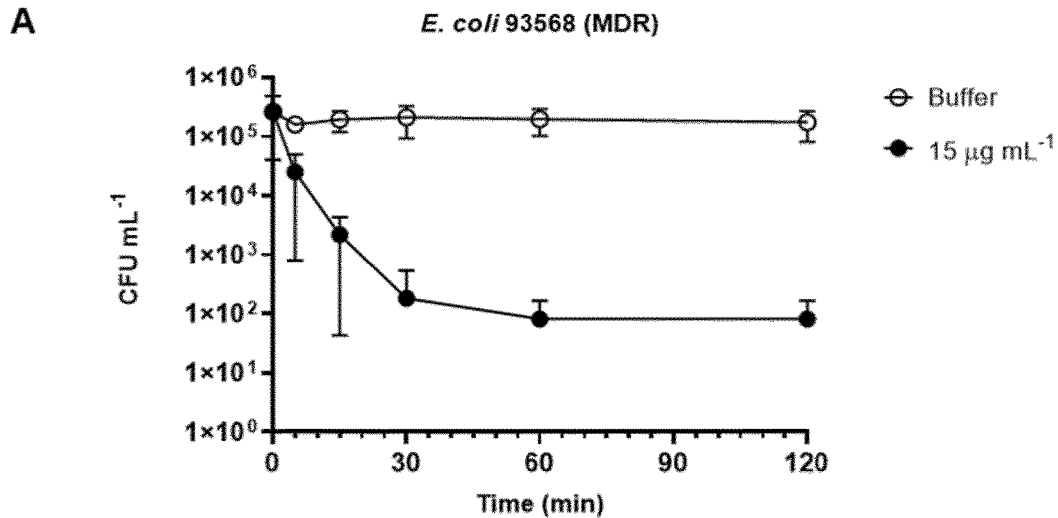
B
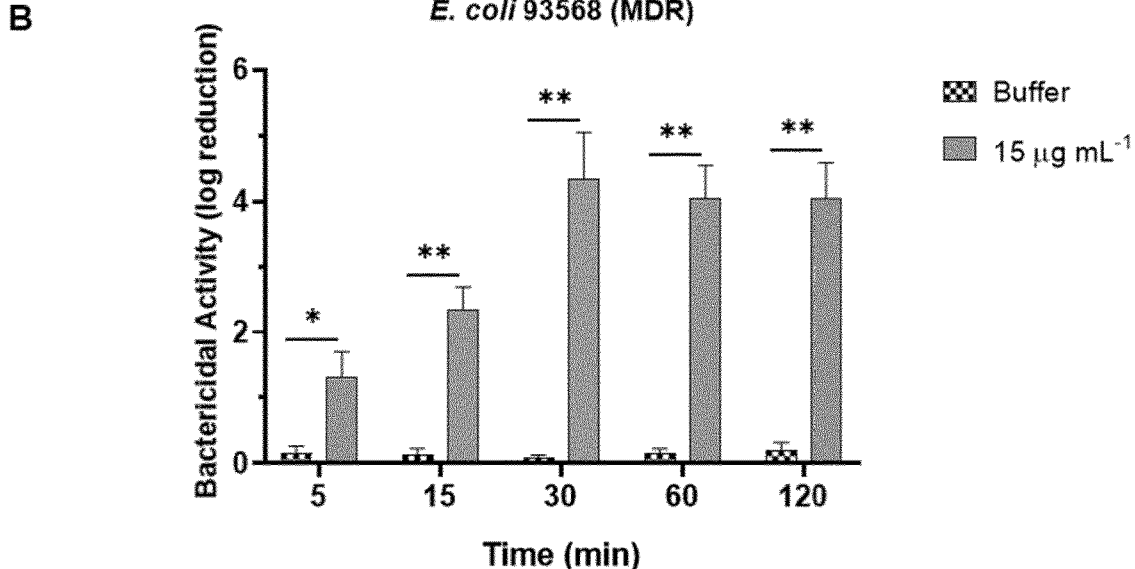

FIG. 5 (cont.)
C
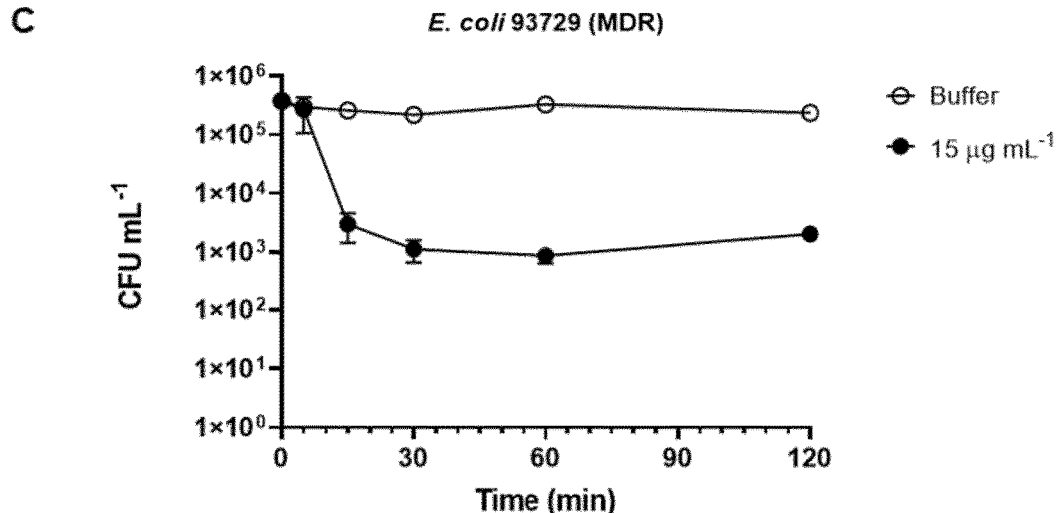
D
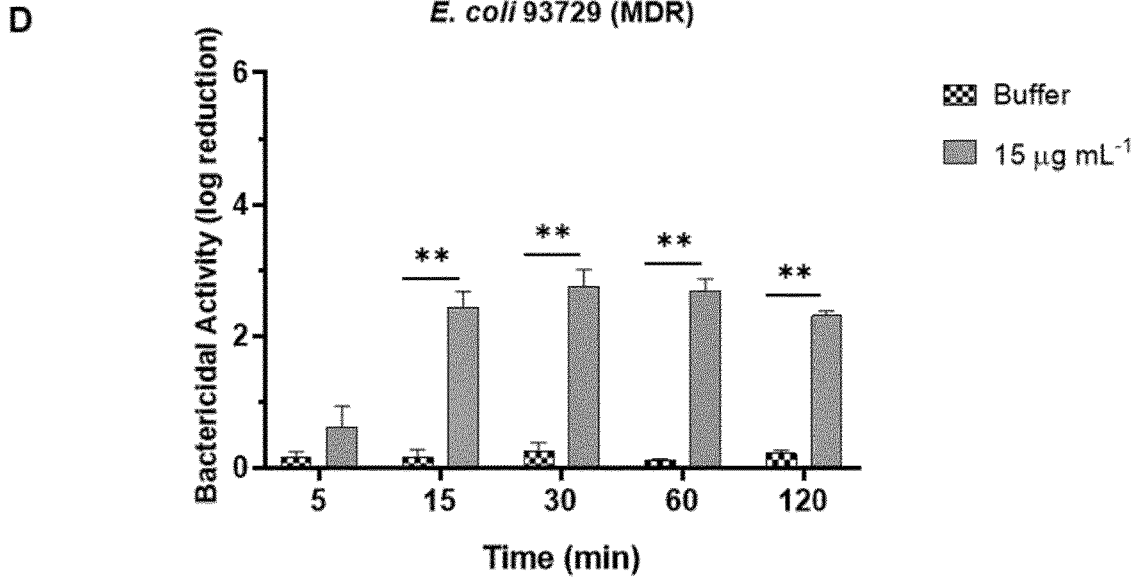

FIG. 5 (cont.)
E
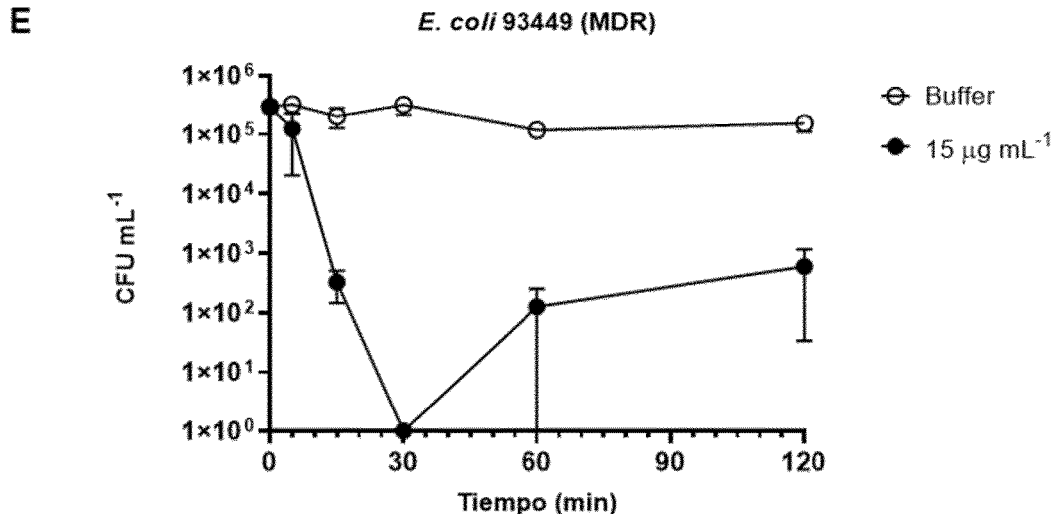
F
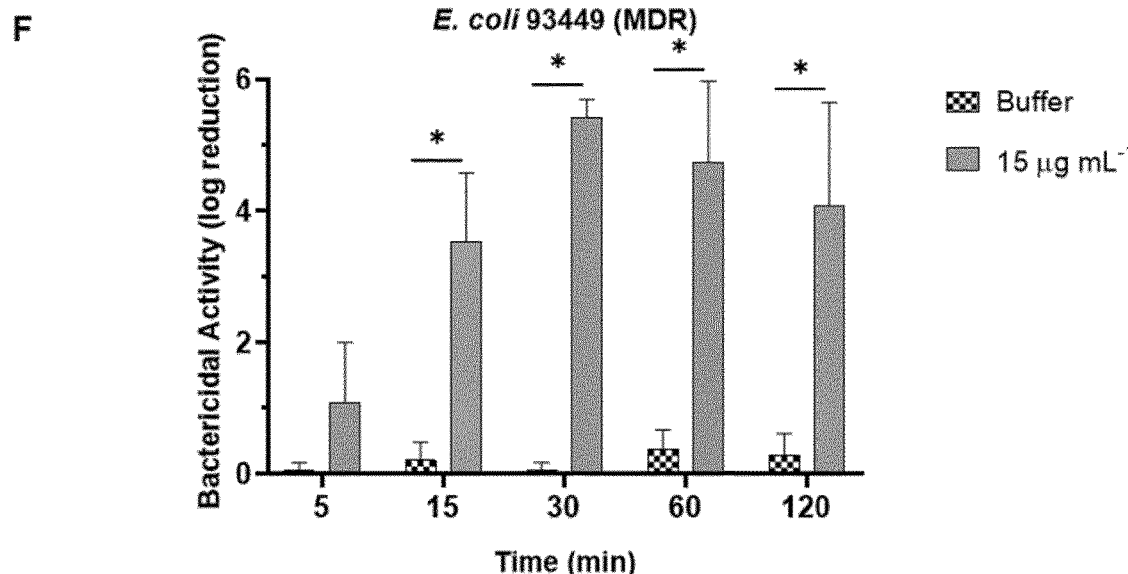

FIG. 6
A
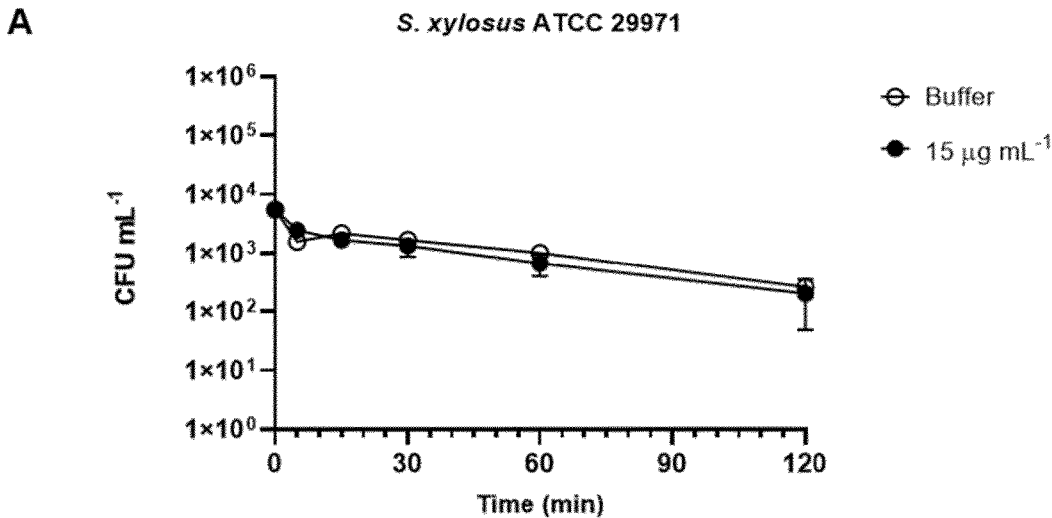
B
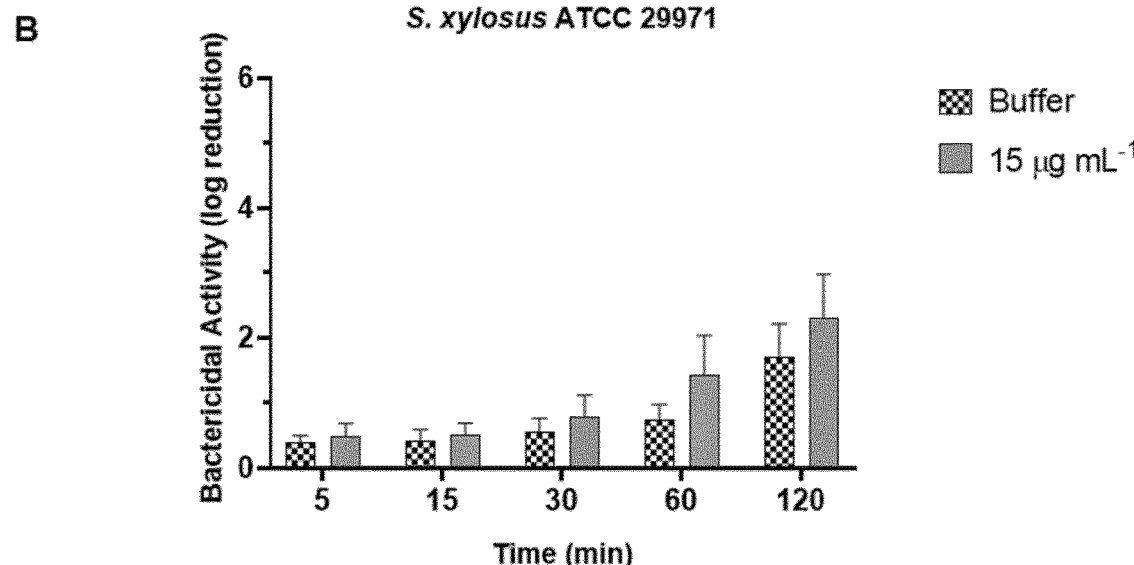

FIG. 6 (cont.)
C
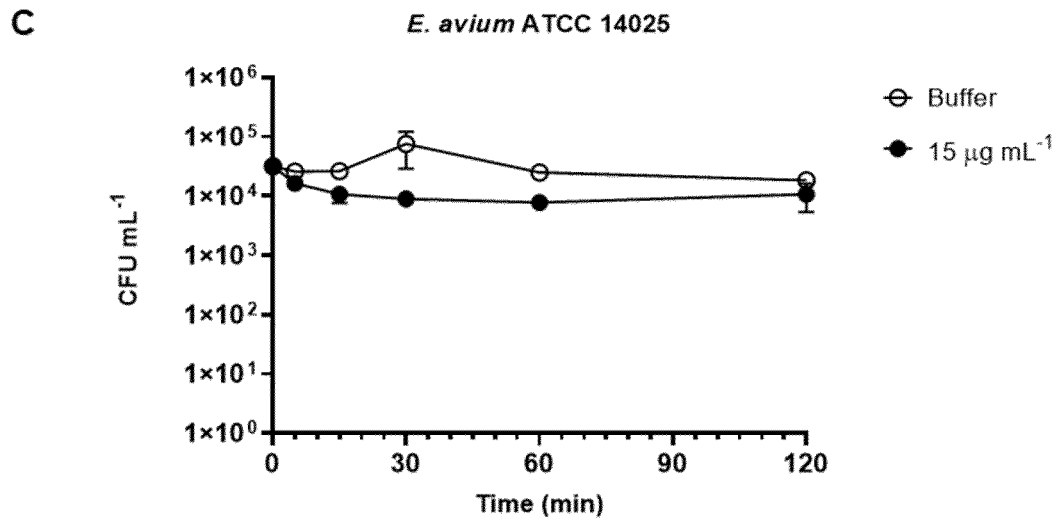
D
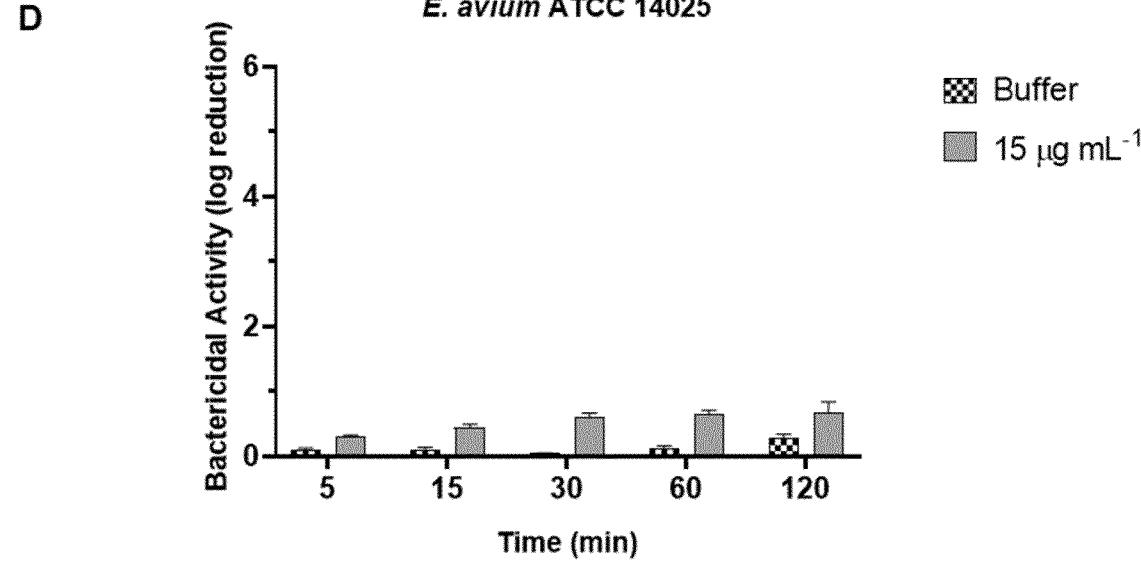

FIG. 6 (cont.)
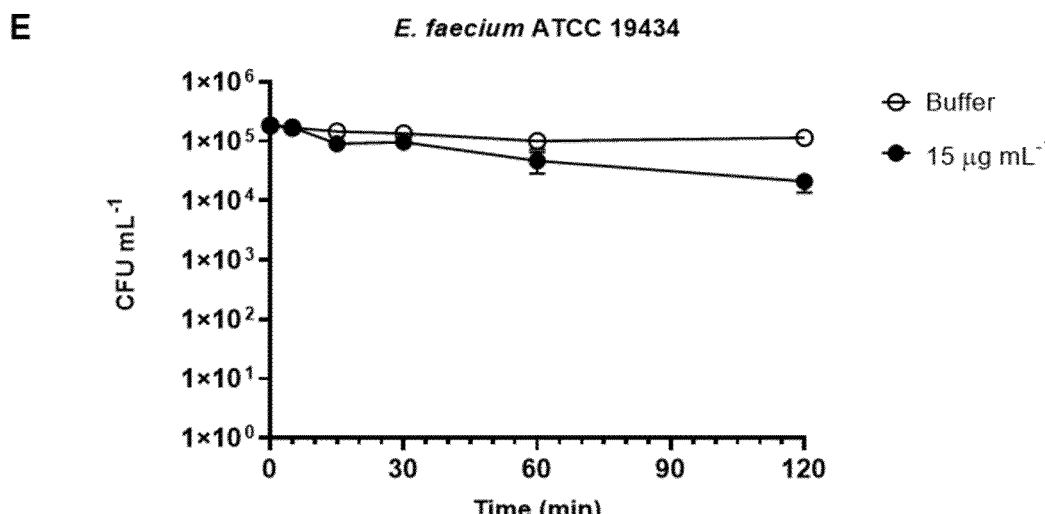
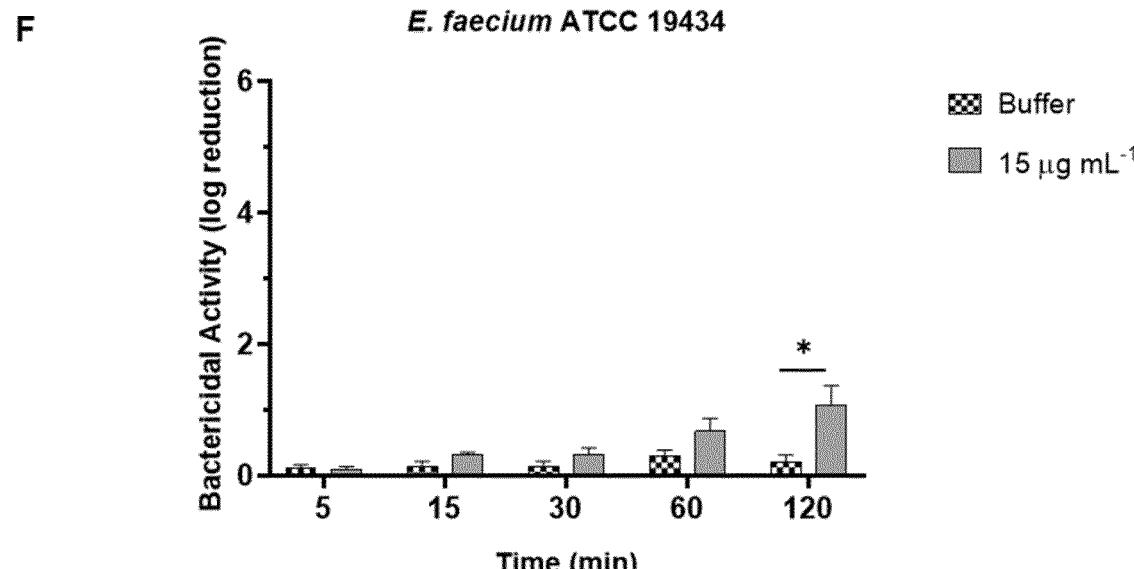

FIG. 6 (cont.)
G
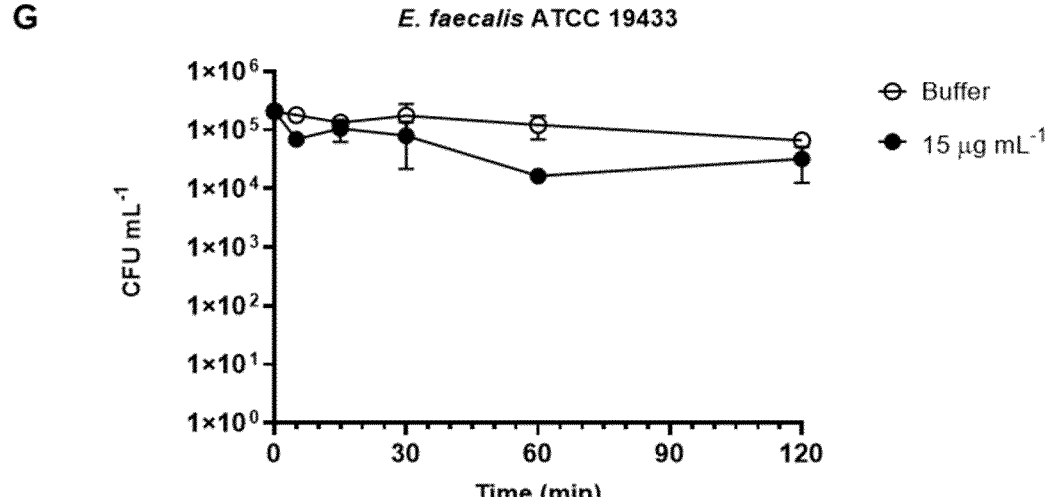
H
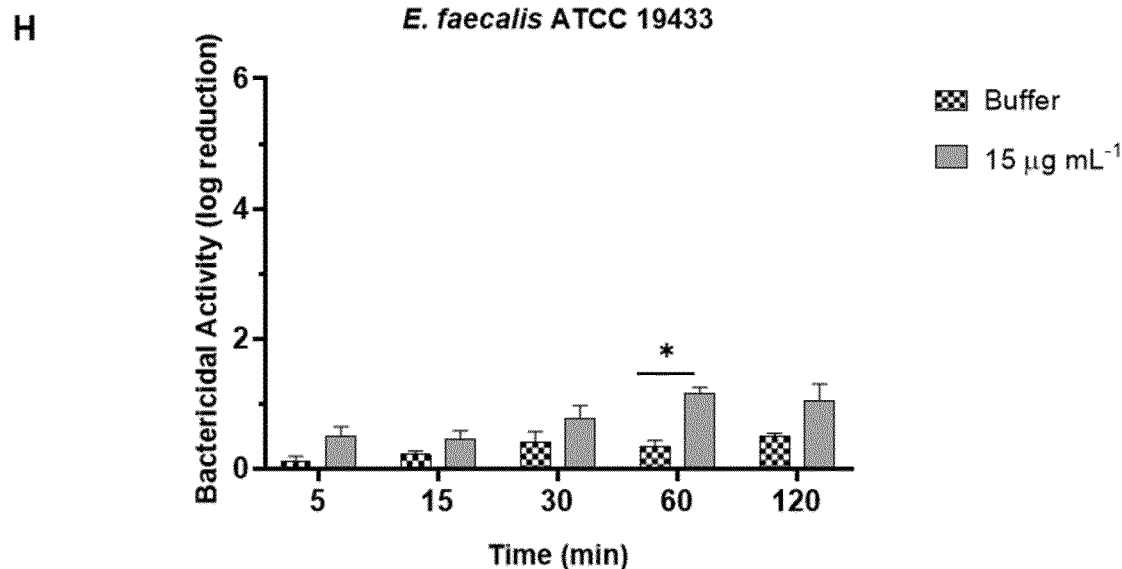

FIG. 7
A
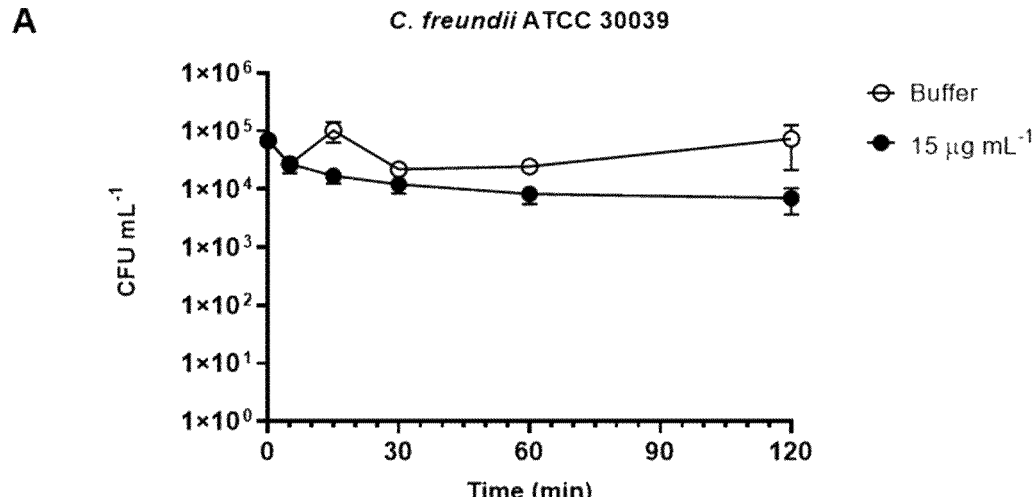
B
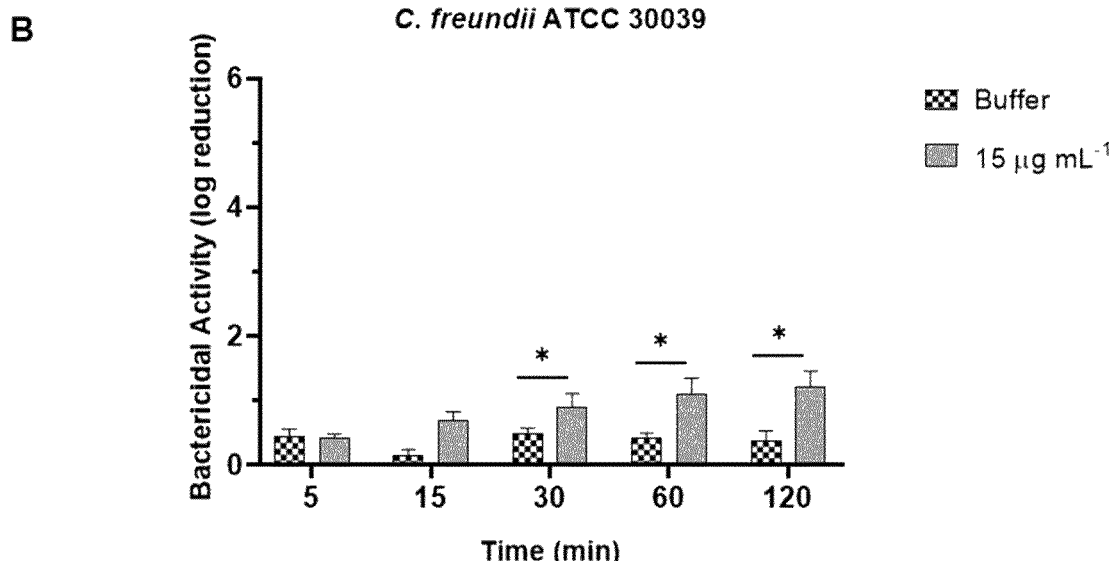

FIG. 7 (cont.)
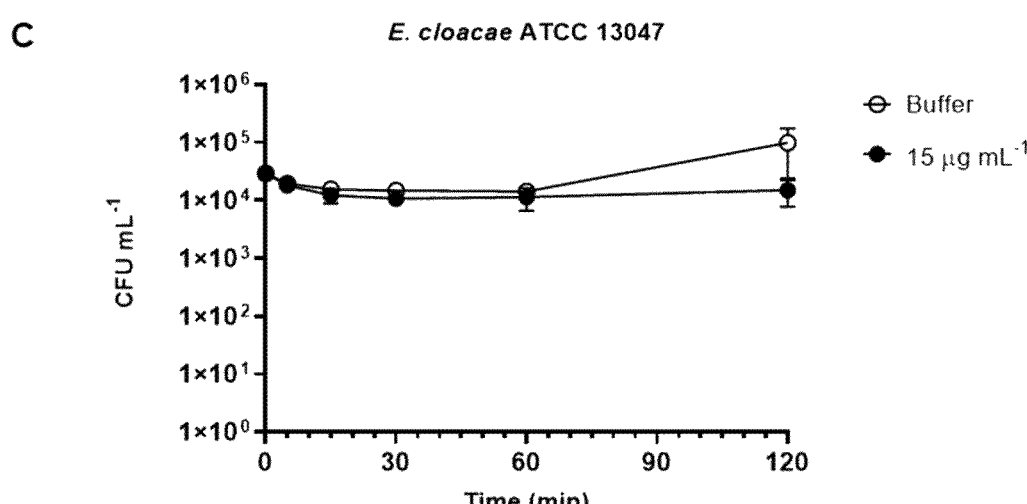
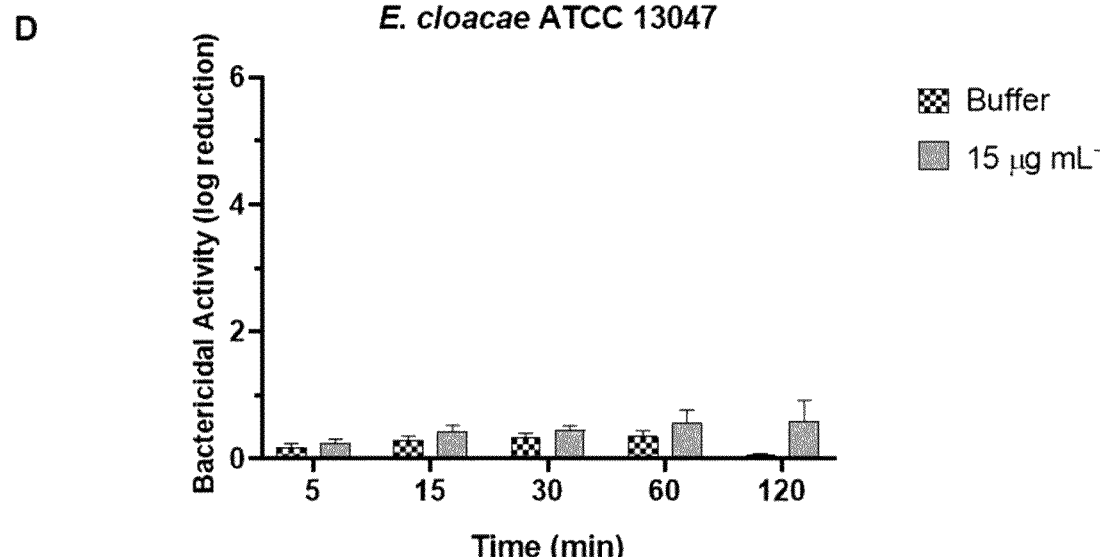

FIG. 7 (cont.)
E
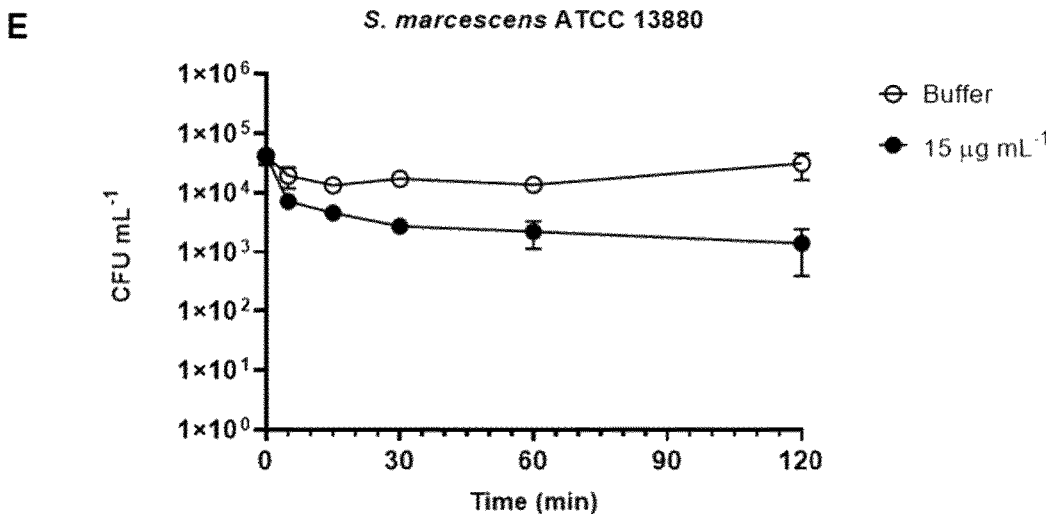
F
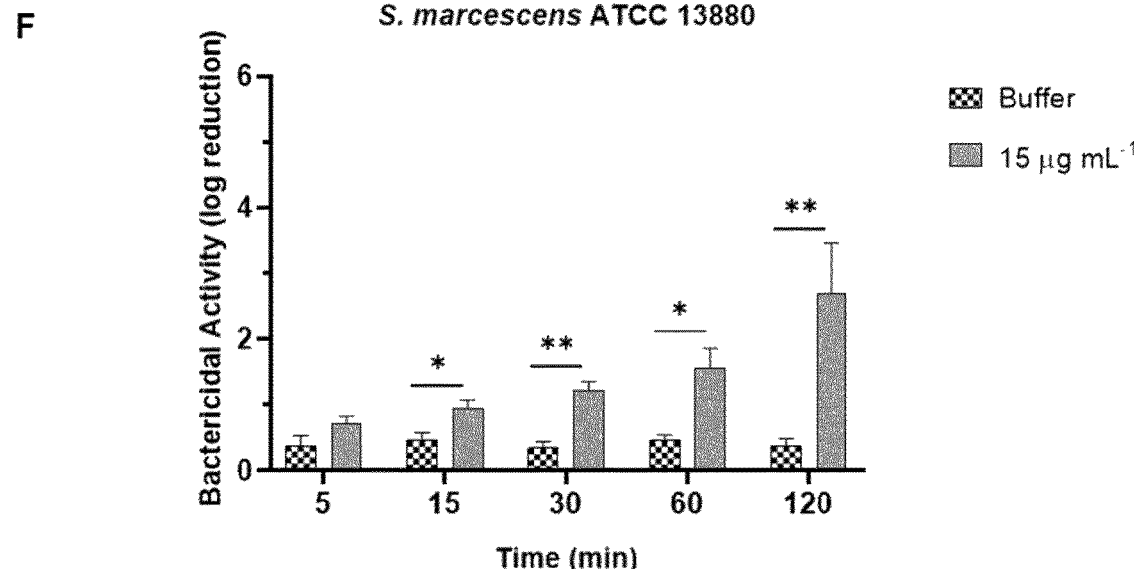

FIG. 7 (cont.)
G
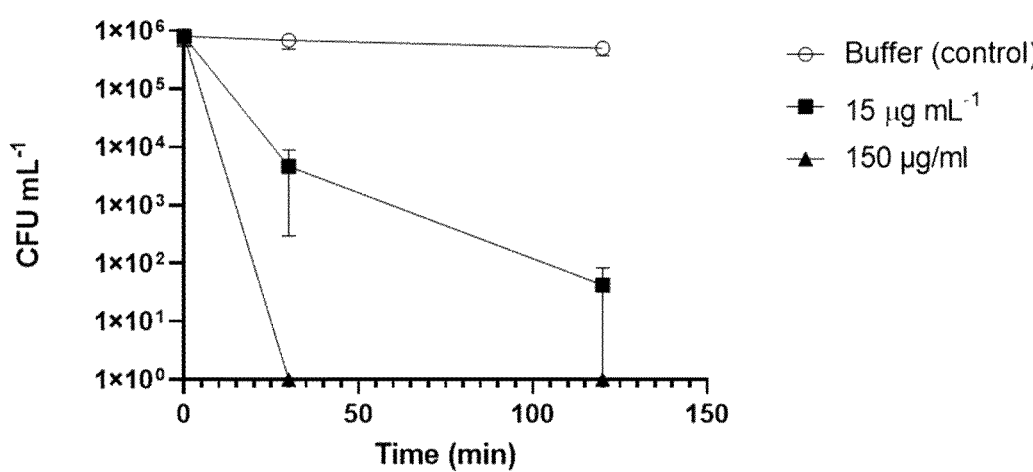
H
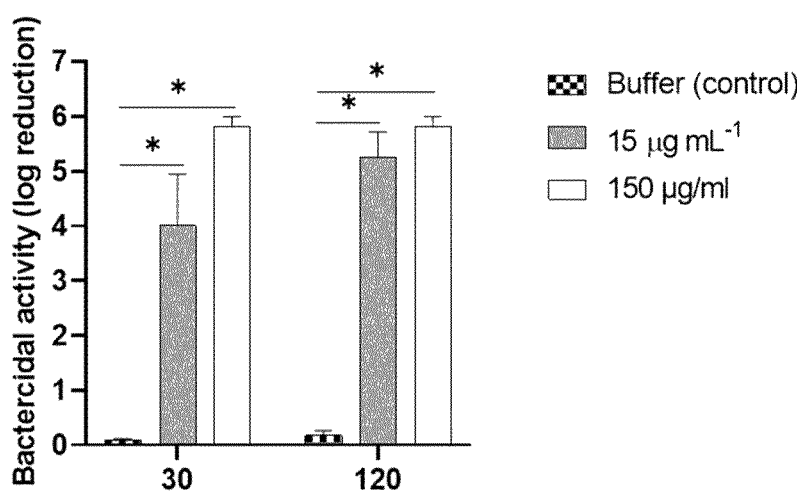

FIG. 7 (cont.)
I
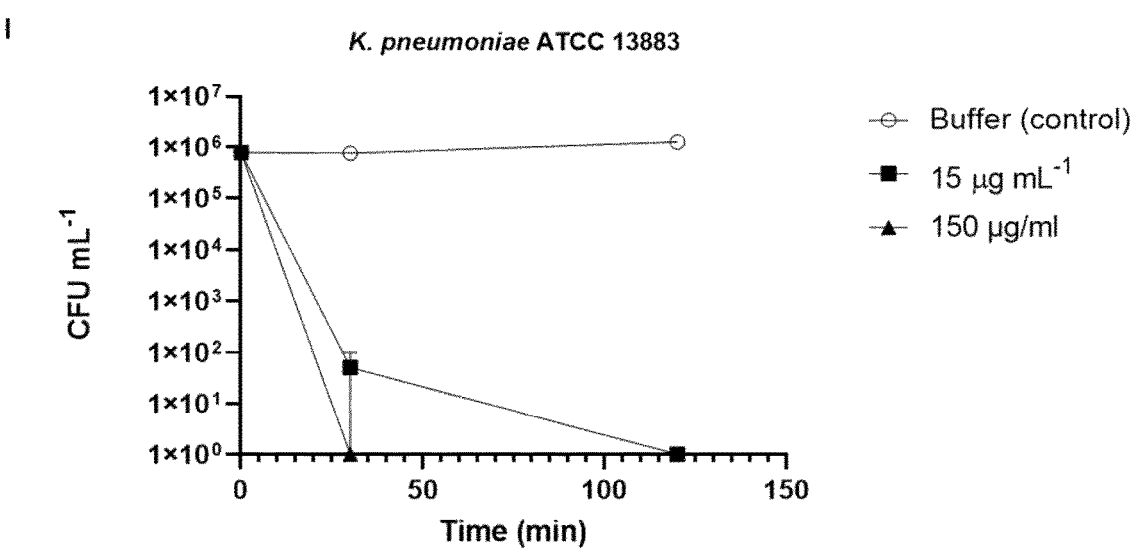
J
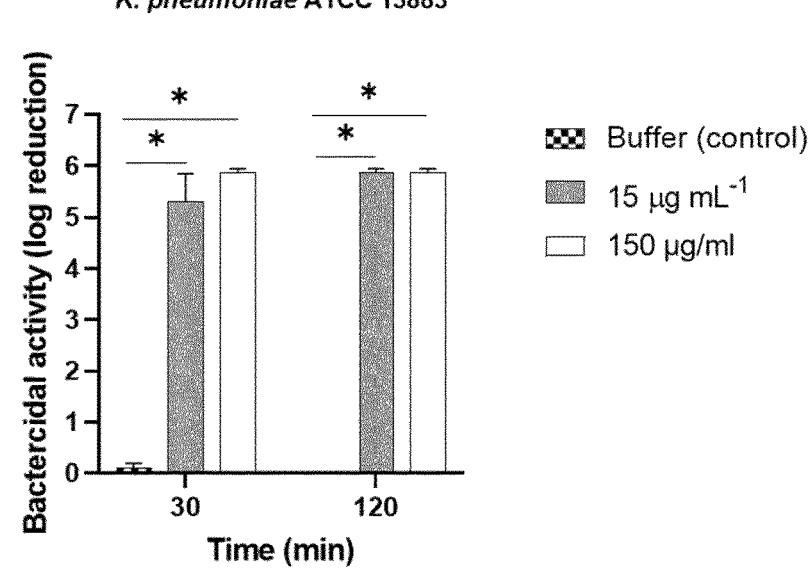

FIG. 8 (cont.)
C
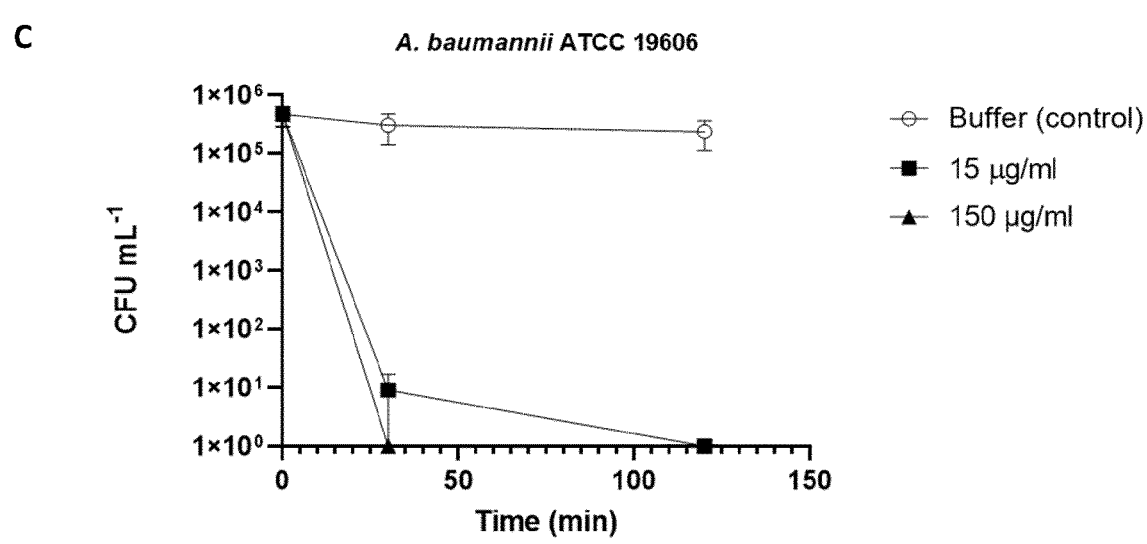
D
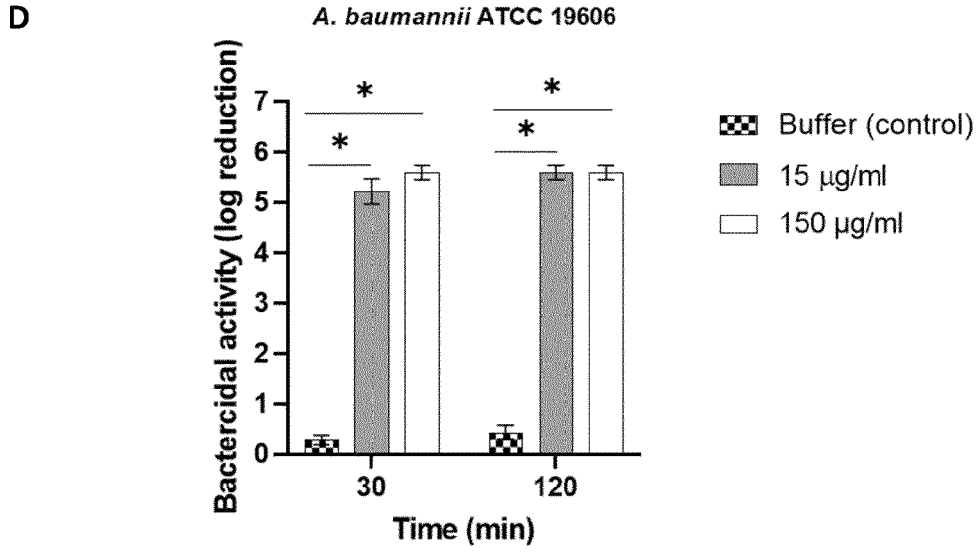

FIG. 9
A
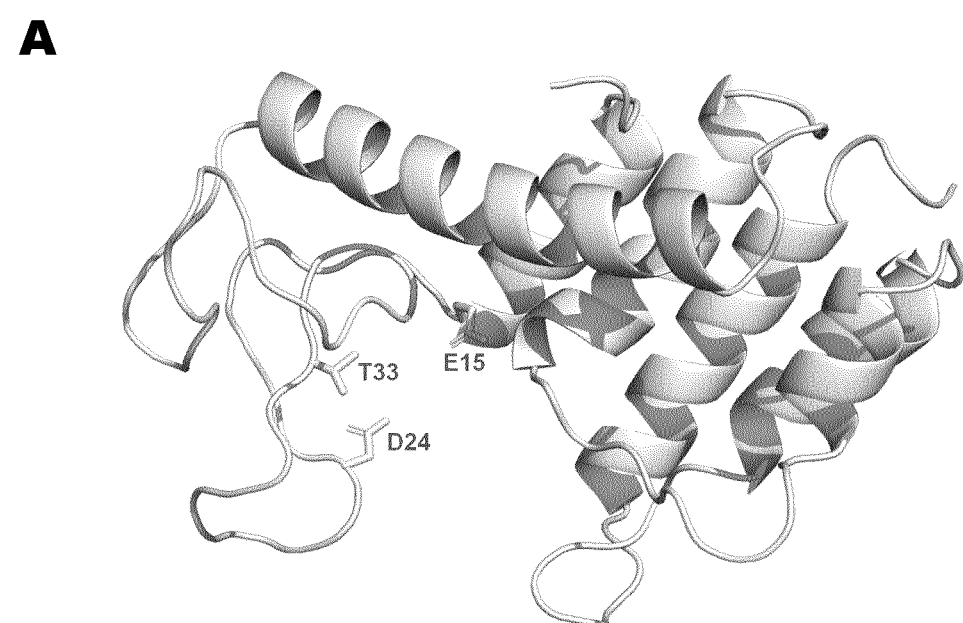
B

FIG. 9 (cont.)
C
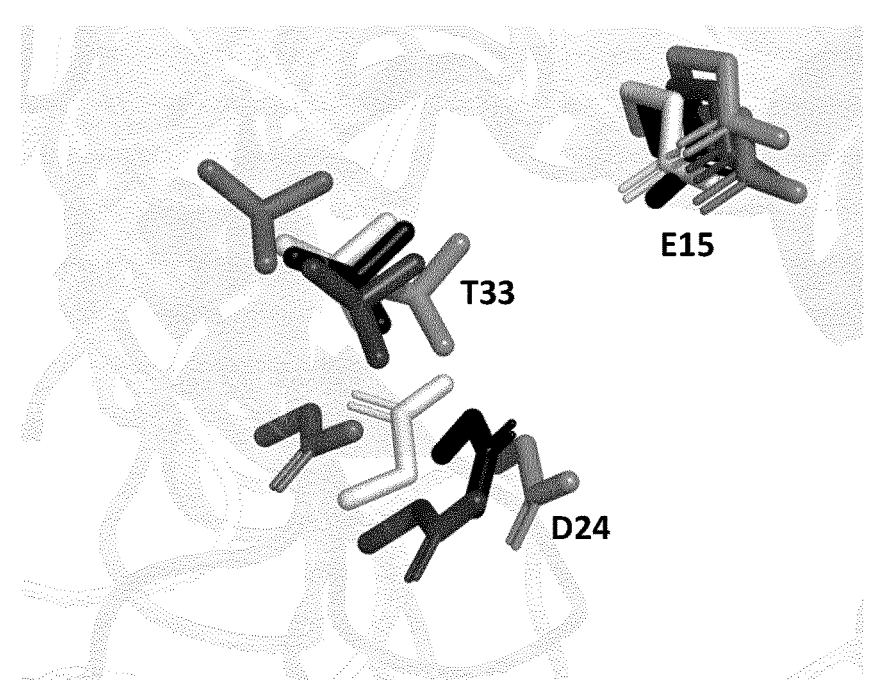
D
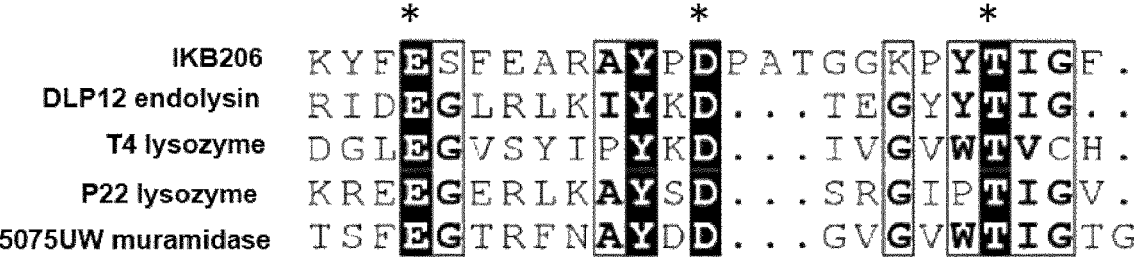

FIG. 10
A
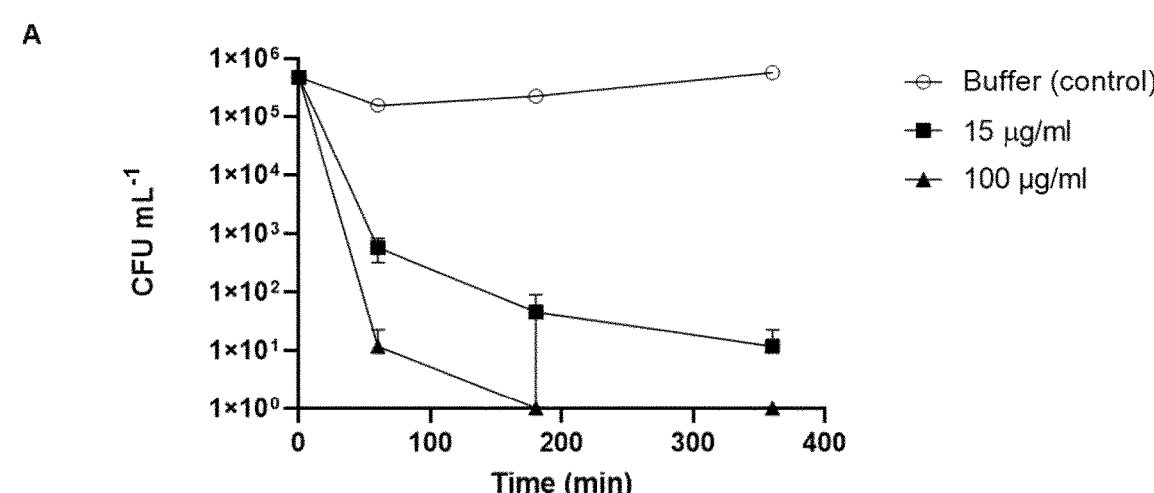
B
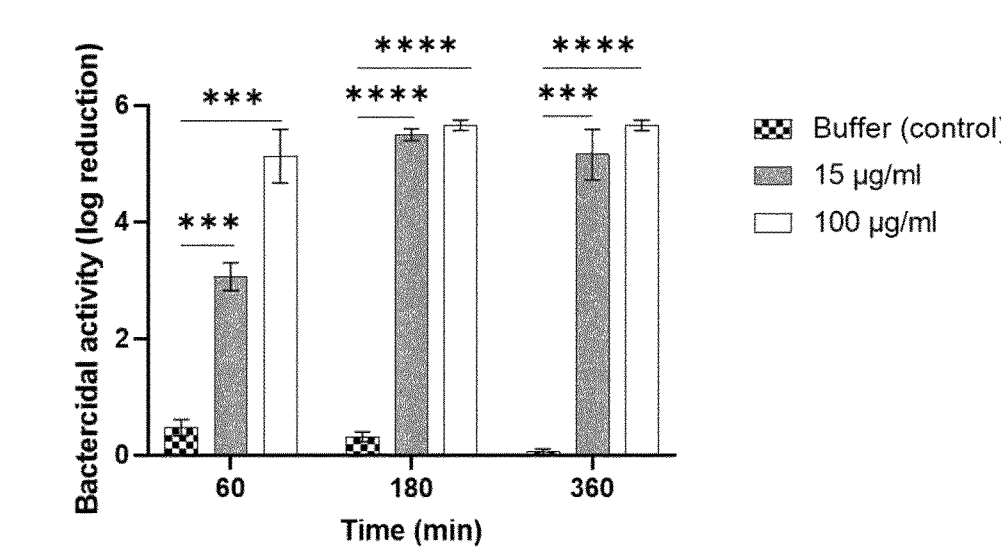

| | | Meropenem | | | | | | | | | |
|---|---|---|---|---|---|---|---|---|---|---|---|
| | | Control | 0.03× MIC | 0.06× MIC | 0.12× MIC | 0.25× MIC | 0.5× MIC | MIC | 2× MIC | | |
| IKB206 | 2× MIC | 0 | 0 | | | | | | 0 | 0 | |
| | MIC | 0 | 0 | | | | | | 0 | 0 | |
| | 0.5× MIC | 1.00E+06 | 0 | 0 | 0 | 0 | 0 | 0 | 0 | |
| | 0.25× MIC | 1.00E+06 | 2.00E+05 | 2.00E+05 | 2.00E+04 | 0 | 0 | 0 | 0 | |
| | 0.12× MIC | 1.00E+06 | 1.00E+06 | 1.00E+05 | 1.00E+05 | 0 | 0 | 0 | 0 | |
| | 0.06× MIC | 1.00E+06 | 1.00E+06 | 3.00E+05 | 2.00E+05 | 2.00E+05 | 0 | 0 | 0 | |
| | 0.03× MIC | 1.00E+06 | 1.00E+06 | 2.00E+05 | 2.00E+05 | 2.00E+05 | 2.00E+05 | 0 | 0 | |
| | Control | 1.00E+06 | 1.00E+06 | 1.00E+06 | 1.00E+06 | 1.00E+06 | 1.00E+06 | 0 | 0 | |

MIC
Control
Synergism

Imipenem

| IKB206 \ Imipenem | Control | 0.03× MIC | 0.06× MIC | 0.12× MIC | 0.25× MIC | 0.5× MIC | MIC | 2× MIC |
|---|---|---|---|---|---|---|---|---|
| 2× MIC | 0 | 0 | 0 | 0 | 0 | 0 | 0 | 0 |
| MIC | 0 | 0 | 0 | 0 | 0 | 0 | 0 | 0 |
| 0.5× MIC | 1.00E+06 | 0 | 0 | 0 | 0 | 0 | 0 | 0 |
| 0.25× MIC | 1.00E+06 | 3.00E+04 | 3.00E+04 | 0 | 0 | 0 | 0 | 0 |
| 0.12× MIC | 2.00E+05 | 2.00E+05 | 1.00E+05 | 3.00E+01 | 0 | 0 | 0 | 0 |
| 0.06× MIC | 5.00E+05 | 3.00E+05 | 3.00E+05 | 3.00E+02 | 2.00E+05 | 0 | 0 | 0 |
| 0.03× MIC | 1.00E+06 | 2.00E+05 | 2.00E+05 | 2.00E+05 | 2.00E+05 | 3.00E+05 | 0 | 0 |
| Control | 1.00E+06 | 1.00E+06 | 1.00E+06 | 1.00E+06 | 1.00E+06 | 3.00E+05 | 0 | 0 |

Legend:
- MIC
- Control
- Synergism
- Possible synergism

RECOMBINANT LYSIN AND ITS USE IN THE TREATMENT OF GRAM-NEGATIVE BACTERIAL INFECTIONS

REFERENCE TO AN ELECTRONIC SEQUENCE LISTING

The contents of the electronic sequence listing (900282.401USPC_Sequence_Listing_v3.txt; Size: 13,051 bytes; and Date of Creation: Jul. 7, 2025) is herein incorporated by reference in its entirety.

FIELD OF THE INVENTION

The present invention relates to the field of clinical and veterinary microbiology. Specifically, it relates to a new recombinant lysin and its use as antimicrobial agent in new treatment approaches for eliminating antibiotic resistant Gram-negative bacteria and minimizing the emergence of new resistances.

BACKGROUND OF THE INVENTION

Since the introduction of antibiotics in the 1940s, these powerful compounds have been used for curing infections in humans and animals, eliminating surface microorganisms, and even preserving foods (Farber, L. et al. 1959). However, bacteria quickly began to show signs of resistance to said antibiotics, with the first penicillin-resistant *staphylococcus* being detected in 1946 (Davies, J. & Davies, D. 2010; Frankel, R. B. et al. 2006). The abuse and misuse of antibiotics has contributed to the emergence and spread of antibiotic resistances in almost all pathogenic bacteria, some of which are even resistant to all available antibiotics. Antibiotic-resistant bacteria are capable of growing in the presence of an antibiotic which would normally kill them or limit their growth, whereas multidrug resistant (MDR) bacteria are capable of growing in the presence of two or more unrelated antibiotics. In a clinical setting, inappropriate use of antibiotics (in viral infections, use of broad-spectrum antibiotics, etc.) involves between 20 and 50% of all antibiotics consumed (Tenover, F. C. 2006, Starrels, J. L. et al. 2009). In the field of the food industry, antibiotics have been used in animal husbandry for the promotion of animal growth, as a prophylactic method, as well as in the treatment of infections in these animals (Lekshmi M. et al. 2017). The indiscriminate use of antibiotics for purposes other than treatment of infections in the food industry has resulted in the emergence of resistant pathogens in the industry's production environments. Various antimicrobial drugs for medical use are being employed today in livestock farming, poultry farming, and aquaculture. Some of said drugs, such as fluoroquinolones, are critical for the treatment of infections by Gram-negative bacteria in humans, thus the efficacy of said antibiotics may be put at risk due to the development of resistances in pathogens with zoonotic potential (Smith, K. E. et al. 1999). As a result of the emergence and spread of pathogenic MDR bacteria, there is an increasing consciousness of the risk of entering a post-antibiotic era in which it will be impossible to treat common bacterial infections in an efficient manner (WHO Report 2007). Several international studies anticipate a series of worldwide catastrophic scenarios in the event of failing to find a quick approach to antimicrobial resistance. Said studies predict 10 million deaths a year for 2050 (O'Neill, J. 2016; Adeyi, O. O. et al. 2017). This risk, along with the very limited new therapy development today, means that there is a need to search for alternative antimicrobial drugs, preferably with new mechanisms of action for minimizing the development of resistances.

These problems have led to the publication of numerous documents by various international organizations such as the Food and Agriculture Organization (FAO) of the United Nations, the World Organization for Animal Health (OIE), or the World Health Organization (WHO) on this topic. In this context, the European Commission has requested its member states to draw up an action plan on antimicrobial drug resistances, highlighting the need for a combined (human and veterinarian) perspective, such that the fight against the development and spread of antibiotic resistance is truly effective.

In Spain, the Ministry of Health, Consumption and Social Welfare (MSCBS) has launched the National Plan against Antibiotic Resistance (Plan Nacional frente a la Resistencia a los Antibióticos—PRAN) as a response to European Commission requirements. This plan includes a series of common programs and strategic lines for human and animal health, such as the voluntary reduction of the consumption of specific antibiotics in different animal species. Specifically, further to having completely eliminated the use of antibiotics in animal feed, the main chicken meat producer's organization in Spain (Organización Interprofesional de la Avicultura de Carne de Pollo—PROPOLLO) have set as a main objective achieving a 45% reduction in total antibiotic consumption in the Spanish Poultry industry within 2 years. In the specific case of colistin, the objective is to achieve an 80% reduction from the current 4.7 mg/kg to 1 mg/kg.

Accordingly, the development of new antimicrobial agents and new treatment approaches for eliminating resistant microorganisms and minimizing the emergence of new resistances to antibacterial drugs has become a matter of urgency today. Alternatives that are more promising or that complement conventional antibiotics include, among others, bacteriophages (phages) and their lytic enzymes (Hojckova, K. et al. 2013; Czaplewski, L. et al. 2016). Bacteriophages represent one of the most abundant biological entities in nature and have been widely known for their potential as therapeutic agents, even before the discovery of antibiotics (Hermoso J. A. et al. 2007). However, in the West, bacteriophages were sidelined following the emergence of antibiotics. The problems that resistant microorganisms pose today have awakened new interest in bacteriophages as possible candidates for the treatment of infections, particularly infections by multidrug resistant microorganisms (Hermoso J.A. et al. 2007). Different research groups are trying to develop strategies for using the intact phage as an alternative to antibiotics. Moreover, research is also being conducted for the isolation and optimization of phage components as antibacterial drugs, opening new doors for the treatment of multidrug resistant infections.

Specifically, phage lysins, are used by bacteriophages at the end of their replication cycle to degrade the peptidoglycan (PG) of the bacterial host from within, resulting in cell lysis and release of progeny virions. It has been reported that this bactericidal effect persists when lysins act exogenously ("from without") on the bacteria, particularly in the case of Gram-positive bacteria due to the cell wall is more exposed because it lacks an outer membrane to the contrary of Gram-negatives. This property has made this type of enzymes candidates to became antimicrobial agents (Nelson D., et al 2012; Schmelcher, M. et al. 2012), also called "enzybiotics". This has been widely described in the literature and it has been demonstrated that lysins can be used as therapeutic agents to prevent infections by group A streptococci (Pires, D. P. et al. 2016) or to control sepsis due to infections by *Enterococcus faecalis* and *Enterococcus faecium* (Nelson D., et al. 2001), *Clostridium perfringens* (Yoong P. et al. 2004), group B streptococci (Zimmer M. et al. 2002), as well as infections by *Streptococcus pneumoniae* (Cheng Q. et al. 2005).

An advantage of endolysins over traditional antibiotics is their high specificity for certain PG types, which generally limits their antimicrobial action to members of a certain bacterial genus, species or even serotype. This near-species specificity greatly reduces the risk of resistant (commensal) strain development that is often associated with the use of broad-range antibiotics, allowing for selective killing of given target pathogens, with commensal bacteria or desired organisms of the accompanying microflora being unaffected (Schmelcher, M. et al. 2012). Another advantage of PG hydrolases is that they are effective against growing cells but also target non-dividing or slowly growing cells, for example biofilms.

In recent years, large investments have been made for obtaining recombinant lysins with improved characteristics, leading to lysin derivatives being among the most promising alternatives in the fight against antibiotic-resistant bacteria. These improved characteristics include increased lytic activity (McCullers J. A. et al. 2007; Schmelcher M. et al. 2011), increased bactericidal spectrum (Díez-Martínez, R. et al. 2015; Becker S.C. et al. 2009; Yang H. et al. 2015; Yang H. et al. 2016), as well as the application of lysins against Gram-negative bacteria (Briers Y. & Lavigne 2015; Briers Y. et al. 2014; Wang, S. et al. 2017; Heselpoth, R. D. et al. 2019; WO2015/200783 and WO2017/049233).

Gram-negative bacteria are intrinsically resistant to many antibiotics due to the permeability barrier that is provided by their unique cell envelope. This envelope consists of an outer membrane (OM) and inner membrane (IM), which are separated by a periplasmic space. The OM is an asymmetric lipid bilayer in which phospholipids exclusively partition on the inner leaflet, while the lipid A moiety of lipopolysaccharide (LPS) forms the outer leaflet. The LPS layer of the OM is an important component in providing a protective layer against harmful compounds in the extracellular environment. The IM is a traditional phospholipid bilayer. Between the two membranes lies the periplasm, a viscous cellular compartment in which the peptidoglycan layer is situated (Masi et al. 2017).

The treatment of Gram-negative bacteria with lysins has been more challenging since the outer membrane (OM) prevents the lytic enzyme from accessing the PG from outside the bacteria. The OM is impermeable to macromolecules and allows only limited diffusion of hydrophobic substances through its LPS-covered surface (Vaara M., 1992) Endolysins are characterized by having a modular structure, often with multiple lytic and/or cell wall-binding domains (CBDs). In order to render lysins active against Gram-negative bacteria, genetically engineered constructs have recently been described to facilitate translocation of the OM (Nelson D., et al. 2012; Schmelcher, M. et al. 2012).

One approach comprises fusing PG hydrolases to various cationic, polycationic or other membrane-disrupting peptides, such as described in WO/2010149792 or WO/2011023702. An alternative approach comprises fusion with a peptide with OM permeabilizing properties. In particular, Wang, S. et al. 2017 describe an *E. coli* bacteriophage lysin (Lysep3) fused to the D8 domain of the Lys 1521 from *Bacillus amyloliquefaciens* phage, which comprises two cationic regions (Morita et al. 2001). The Lysep3/D8 fusion protein was reported in Wang, S. et al. 2017 to have lytic activity both on Gram-negative and Gram-positive bacteria. In particular, lytic effects are mentioned to be observed in 14 *E. coli* strains, 3 *Pseudomonas aeruginosa* strains, 1 *Acinetobacter baumannii* strain, and 1 *Streptococcus* strain. Thus, this chimeric endolysin is not selective for Gram-negative bacteria.

Nevertheless, despite recent advancements, there is a need to search for novel lysins with improved properties with the aim to eradicate MDR bacteria and successfully prevent further resistance development. In particular, there is an on-going need to identify new lysins with the ability to lyse Gram-negative bacteria upon external administration which are not toxic and which are specific for a narrow range of closely related pathogens. From Gram-negative bacteria, antibiotic resistance in *Escherichia coli* is of particular concern because it is the most common Gram-negative pathogen in humans. For example, in a 2017 European surveillance, the prevalence of *E. coli* MDR ranged from 12-50% (European Centre for Disease Prevention and Control. Surveillance of antimicrobial resistance in Europe—Annual report of the European Antimicrobial Resistance Surveillance Network (EARS-Net) 2017. Stockholm: ECDC; 2018).

In addition, there is the need to find new recombinant lysins with the desired safety, efficacy, and selectivity to replace and/or decrease the use of antibiotics (e.g. by using the lysins in combination with antibiotics) in the treatment of Gram-negative infections, such as caused by *E. coli, K. pneumoniae, P. aeruginosa* and/or *Acinetobacter* species.

SUMMARY OF THE INVENTION

In one aspect the invention provides a new recombinant endolysin which comprises a domain with PG-hydrolase activity and a cell permeability domain to increase the permeability of the OM.

The chimeric protein of the invention was shown to present great bactericidal efficacy against Gram-negative bacteria, in particular against *E. coli, K. pneumoniae, A. baumannii* and *P. aeruginosa*. This new enzybiotic was also shown by the inventors to be safe for mammalian cells and to have a substantial degree of selectivity for Gram-negative bacteria, especially against *E. coli K. pneumoniae, A. baumannii* and *P. aeruginosa*, not affecting Gram-positive bacteria from chicken microbiota.

In the in vitro assays performed with a chimeric protein of the invention (i.e., IKB206), it can be observed that at very low concentrations (5 µg mL$^{-1}$), the chimeric enzyme was capable of significantly reducing the number of *E. coli* ATCC 25922, a serotype 06 reference strain often used in quality control testing (Minogue et al, 2014) in 15 min (FIG. 3). Furthermore, when the concentration of IKB206 was increased to 15 µg mL$^{-1}$, it was capable of significantly reducing the number of cells in as little as 5 min and killing all the cells present in the suspension (5-log) when the cells were incubated for 30 min. These results were obtained at doses as low as 15 µg mL$^{-1}$ and without the use of membrane disruptors. Moreover, this enzyme was capable of killing the entire culture in an incubation time as low as 15 min at the concentration of 60 µg mL.

Surprisingly, the obtained efficacy is significantly higher than that described in Wang, S. et al. 2017 where an *E. coli* bacteriophage lysin (Lysep3) was fused to the D8 domain of the Lys 1521 from *Bacillus amyloliquefaciens* phage (Morita, M. et al. 2001; Orito Y. et al. 2004).

Indeed, in Wang, S. et al. 2017, the assays were performed at a protein concentration of 60 µg mL$^{-1}$, whereas in the case of the chimeric protein of the invention, a bactericidal effect (a reduction of more than 3-log), was observed at a concentration of 15 μg mL$^{-1}$ after only 15 minutes of incubation, i.e., an amount that is 4 times lower (see FIGS. 3A & B). Moreover, the chimeric protein of the invention was shown to be capable of killing all the cells in an incubation period of only 30 min, whereas the protein in Wang, S. et al. was only capable of achieving 1- or 2-log reduction in an incubation time of 2 hour. In addition, Wang, S. et al. failed to demonstrate bactericidal activity on O157: H7, the most clinically relevant *E. coli* serotype, whereas the chimeric lysin of the invention presented excellent activity on this serotype (FIGS. 4A & 4B).

Moreover, bactericidal activity of IKB206 was also determined on MDR *E. coli* strains isolated from chicken. It was observed that IKB206 was capable of achieving, in a significant manner, between 2- and 5-log (100- and 100000-fold) reductions in the number of bacteria present in the assays after 30 minutes of incubation with 15 μg mL$^{-1}$ (FIG. 5).

On the other hand, IKB206 showed great bactericidal activity against the *K. pneumoniae, A. baumannii* and *P. aeruginosa* strains tested, including antibiotic resistant strains. (FIGS. 7 and 8). IKB206 shows bactericidal activity against all strains tested at a concentration of 15 μg mL$^{-1}$ and an incubation time of 120 min. Furthermore, at a concentration of 150 μg mL-1 and 120 min of incubation, the chimeric protein is capable of killing all the cells present in the assay.

It is well known that the gut microbiota composition greatly influences both human and animal health by means of a wide range of mechanisms covering immune function control (Hooper, L. V. et al. 2012), metabolism homeostasis control (Ley, R. E. et al. 2006, Cani, P. D. & Delzenne, N. M. 2009), or medicinal product metabolism control (Claus, S. P. et al. 2011).

The use of antimicrobial drugs has been associated with a reduction in microbiota diversity, which is in turn associated with the subsequent weakening of metabolism (Schulfer A. F. et al. 2018, Le Roy, C. I. et al. 2019). Therefore, it is important to determine whether or not an antimicrobial drug has effect on the host microbiota.

To determine if the chimeric protein of the invention has a killing effect on other bacteria present in the gut microbiota of chickens, in vitro assays were performed with IKB206 to determine its bactericidal effect on different bacterial species that are part of the gut microbiota of chickens. It was observed in said assays that the species studied as part of the gut microbiota of farmed chickens were not affected by IKB206, resulting in a safe treatment in terms of gut microbiota (FIG. 6).

The structural modeling of the domains and a sequence alignment suggested that the catalytic domain of IKB206 belongs to the T4 lysozyme-like endolysins and residues E15, D24 and T33 form the catalytic triad of the enzyme (FIG. 9).

Surprisingly, the inventors found that the catalytic domain (SEQ ID NO:1) by itself had intrinsic bactericidal activity against Gram-negative bacteria. In particular, IKB206AD8 at a concentration of 15 μg mL$^{-1}$ was found to induce a reduction in CFU/mL of about 3-log on *E. coli* strain ATCC 25922 after 60 minutes, reaching about 5 log reduction at 180 minutes (FIG. 10).

In light of the obtained results, a series of in vivo assays were performed in a zebrafish animal model. As shown in FIG. 11, IKB206 exhibited a protective effect against death caused by infection with *E. coli* ATCC 25922, particularly at a dose of 1 μg g-1 (66.6% of survival).

Moreover, toxicity studies were performed in vitro on human cells (FIG. 12). It was observed that the protein IKB206 was not toxic at the tested concentrations/dosages. These results suggest that the recombinant lysin of the invention would be safe for use in the prophylactic and/or therapeutic treatment of infections by Gram negative bacteria, such as *E. coli* in humans or animals.

Finally, the inventors assessed the possible synergism between the chimeric protein of the invention and some of the most commonly used antibiotics against MDR *E. coli* strains, in particular the combination with antibiotics of the carbapenem group. Checkerboard experiments suggested a synergistic effect for meropenem and imipenem (Tables 3 and 4 and FIGS. 13A & B). These results were confirmed by the bacterial death assays with *E. coli* ATCC 25922 strain (FIGS. 14A & B).

Accordingly, in a first aspect, the invention relates to a protein comprising or consisting of:

a) amino acid sequence SEQ ID NO:1 or a variant sequence or fragment with at least 60% identity thereto, wherein said variant has conservative amino acid changes and said variant or fragment has at least 90% of the peptidoglycan hydrolase activity of SEQ ID NO:1; and wherein said protein does not consist of SEQ ID NO:1.

In a second aspect, the present invention relates to a chimeric protein comprising:

a) a polypeptide comprising or consisting of amino acid sequence SEQ ID NO:1, or a variant sequence with at least 60% identity thereto, or a fragment of any thereof, wherein said variant has conservative amino acid changes and wherein said variant or fragment is a biologically active polypeptide In particular, wherein said variant or fragment has at least 90%, preferably, at least 95%, more preferably at least 96%, 97%, 98%, 98%, 99% or 100% of the peptidoglycan hydrolase activity of SEQ ID NO: 1; and b) a polypeptide comprising or consisting of amino acid sequence SEQ ID NO:2 or a variant sequence with at least 60% identity thereto, or a fragment of any thereof, wherein said variant has conservative amino acid changes and wherein said variant or fragment is a biologically active polypeptide. In particular, wherein said variant or fragment has at least 90%, preferably, at least 95%, more preferably at least 96%, 97%, 98%, 98%, 99% or 100% of the cell permeating activity of SEQ ID NO: 2.

In a third aspect, the invention relates to a polynucleotide comprising a nucleic acid molecule encoding a protein (including a chimeric protein) as described herein.

In a fourth aspect, the present invention further relates to a vector comprising a polynucleotide as described herein.

In a fifth aspect, the present invention refers to a host cell comprising a vector as described herein.

In a sixth aspect, the invention relates to a method for producing a protein (including a chimeric protein) of the invention, wherein said method comprises:

i. introducing a vector comprising a polynucleotide as described herein into an appropriate host cell;

ii. culturing the host cell under conditions suitable for the expression of said protein, iii. optionally, isolating and/or purifying said protein.

In a seventh aspect, the present invention relates to a composition comprising a protein (including a chimeric protein), a polynucleotide, a vector or a host cell as described herein.

In a eight aspect, the present invention provides a protein (including a protein consisting of amino acid sequence SEQ ID NO:1, a protein and a chimeric protein as described herein), a polynucleotide, a vector or a host cell or a pharmaceutical composition as described herein (hereinafter generically referred as "an agent according to the invention) for use in the prophylactic and/or therapeutic treatment of a bacterial infection caused by Gram-negative bacteria.

In an ninth aspect, the present invention pertains to the use of a protein (including a protein consisting of amino acid sequence SEQ ID NO:1, a protein and a chimeric protein as described herein), a polynucleotide, a vector, a host cell or a pharmaceutical composition as described herein in the manufacturing a medicament for the prophylactic and/or therapeutic treatment of a bacterial infection caused by Gram-negative bacteria.

In a tenth aspect, the present invention refers to a method for the prophylactic and/or therapeutic treatment of a bacterial infection caused by Gram-negative bacteria comprising administering to a subject diagnosed with, at risk for, or exhibiting symptoms of a bacterial infection, a composition containing an effective amount of a protein (including a protein consisting of amino acid sequence SEQ ID NO:1, a protein and a chimeric protein as described herein), a polynucleotide, a vector or a host cell as described herein.

In a eleventh aspect the present invention relates to a process of preparation of a pharmaceutical composition, said process comprising admixing one or more of a protein (including a protein consisting of amino acid sequence SEQ ID NO:1, a protein and a chimeric protein as described herein), polynucleotide, vector or host cell according to the present invention with a pharmaceutically acceptable carrier, vehicle or excipient.

In an twelfth aspect, the present invention relates to a kit comprising a protein (including a protein consisting of amino acid sequence SEQ ID NO:1, a protein and a chimeric protein as described herein), a polynucleotide, a vector, a host cell or the composition as defined herein, alone or in combination.

In a thirteen aspect the invention pertains to an in vitro method of inhibiting the growth, or reducing the population, or killing of Gram-negative bacteria, the method comprising contacting the bacteria with a protein (including a protein consisting of amino acid sequence SEQ ID NO:1, a protein and a chimeric protein as described herein), a polynucleotide, a vector, a host cell or a composition as described herein.

In a fourteenth aspect, the invention provides a protein (including a protein consisting of amino acid sequence SEQ ID NO: 1, a protein and a chimeric protein as described herein), a polynucleotide or an expression vector or host cell as described herein, wherein the protein or encoded polypeptide has the property of inhibiting the growth, reducing the population, or killing Gram-negative bacteria.

In a fifteenth aspect, the invention also relates to an agent of the invention (e.g., a protein (including a protein consisting of amino acid sequence SEQ ID NO:1, a protein and a chimeric protein as described herein), polynucleotide, expression vector or host cell) as described herein, or the pharmaceutical composition comprising the same, for use in a method of treating and/or preventing Gram-negative bacterial infections as described herein, wherein said treatment comprises the administration of an agent of the invention as described herein in combination with another drug.

The invention is also directed to the use of an agent of the invention as described herein for the manufacture of a medicament for the treatment and/or prevention of Gram-negative bacterial infections as described herein by a combination therapy employing an agent of the invention as described herein with another drug, preferably an antibiotic, as described herein.

It is further directed to a method of treating and/or preventing Gram-negative bacterial infections as described herein, comprising administering to a patient in need of such treatment a therapeutically effective amount of an agent of the invention as described herein, in combination with a therapeutically effective amount of another drug, preferably an antibiotic, as described herein.

In a further aspect, the present invention also relates to the use of a protein (including a protein consisting of amino acid sequence SEQ ID NO:1, a protein and a chimeric protein as described herein) as described herein as disinfectant for materials and/or surfaces, in hospitals as well as in private households.

BRIEF DESCRIPTION OF THE DRAWINGS

FIG. 1: A) Above, schematic representation of IKB206 (SEQ ID NO. 3). The numbers indicate the position of amino acids. The white box corresponds with phage Arya endolysin; the black box corresponds with *B. amyloliquefaciens* phage lysin domain D8. Below, amino acid sequence of chimera IKB206. The letters within the white box correspond to the amino acids of the phage Arya endolysin and those of the black box with those of the *B. amyloliquefaciens* phage lysin domain D8. B) Above, schematic representation of IKB206$_{tags}$ (SEQ ID NO. 5). The numbers indicate the position of amino acids. The box with black and white squares corresponds with S-tag and the thrombin cleavage site; the white box corresponds with phage Arya endolysin; the black box corresponds with *B. amyloliquefaciens* phage lysin domain D8, and the box with diagonal lines corresponds with the thrombin cleavage site and His-tag. Below, amino acid sequence of chimera IKB206$_{tags}$. Bold letters correspond to the amino acids of the S-tag and His-tag; the underlined letters correspond to the amino acids of the thrombin cleavage site; the letters within the white box correspond to the amino acids of the phage Arya endolysin and those of the black box with those of the *B. amyloliquefaciens* phage lysin domain D8. C) Above, schematic representation of IKB206ΔD8 (SEQ ID NO:1). The numbers indicate the position of amino acids. The white box corresponds with phage Arya endolysin. Below, amino acid sequence of IKB206ΔD8.

FIG. 4: Bactericidal effect of IKB206$_{tags}$ on *E. coli* serotype O157: H7. *E. coli* cultures were resuspended in buffer, adjusting the bacterial suspension to $10^5$ CFU mL$^{-1}$, and the cultures were incubated in the absence or presence of the enzyme at 37° C. for 2 h. The data is representative of 5 independent experiments. Viable cells were determined by counting in LB agar plates. A) Bactericidal effect of expressed IKB206$_{tags}$ on the reduction of CFU mL$^{-1}$ over time in the presence of 15 µg mL$^{-1}$ of the enzyme. B) Bactericidal effect of expressed IKB206$_{tags}$ on the reduction of the number of logs over time in the presence of 15 µg mL$^{-1}$ of the enzyme. The error bars represent the standard error. The asterisks represent a significant difference (* P<0.05;  P<0.005; * P<0.0005) with respect to the control (buffer) according to: a T-test in the case of samples showing a normal distribution and homoscedasticity; and a U-Mann Whitney test in the case of samples not showing a normal distribution or showing heterogeneity of variances.

FIG. 5: Bactericidal effect of IKB206$_{tags}$ on *E. coli* multidrug resistant strains. *E. coli* cultures were resuspended in buffer, adjusting the bacterial suspension to $10^5$ CFU mL$^{-1}$, and the cultures were incubated in the absence or presence of the enzyme at 37° C. for 2 h. The data is representative of 3 to 5 independent experiments. Viable cells were determined by counting in LB agar plates. A, C, and E) Bactericidal effect of expressed IKB206$_{tags}$ on the reduction of CFU mL$^{-1}$ over time in the presence of 15 µg mL$^{-1}$ of the enzyme. B, D, and F) Bactericidal effect of expressed IKB206$_{tags}$ on the reduction of the number of logs over time in the presence of 15 µg mL$^{-1}$ of the enzyme. The error bars represent the standard error. The asterisks represent a significant difference (* P<0.05;  P<0.005; * P<0.0005) with respect to the control (buffer) according to: a T-test in the case of samples showing a normal distribution and homoscedasticity; and a U-Mann Whitney test in the case of samples not showing a normal distribution or showing heterogeneity of variances.

FIG. 6: Bactericidal effect of IKB206$_{tags}$ on different strains of chicken microbiota. The cultures were resuspended in buffer, adjusting the bacterial suspension between 103 and 105 CFU mL$^{-1}$, and the cultures were incubated in the absence or presence of the enzyme at 37° C. for 2 h. The data is representative of 4 to 5 independent experiments. Viable cells were determined by counting in LB agar plates. A, C, E, and G) Bactericidal effect of expressed IKB206$_{tags}$ on the reduction of CFU mL$^{-1}$ over time in the presence of 15 µg mL$^{-1}$ of the enzyme. B, D, F, and H) Bactericidal effect of expressedIKB206$_{tags}$ on the reduction of the number of logs over time in the presence of 15 µg mL$^{-1}$ of the enzyme. The error bars represent the standard error. The asterisks represent a significant difference (* P<0.05;  P<0.005; * P<0.0005) with respect to the control (buffer) according to: a T-test in the case of samples showing a normal distribution and homoscedasticity; and a U-Mann Whitney test in the case of samples not showing a normal distribution or showing heterogeneity of variances.

FIG. 9: Structural model of the catalytic domain of IKB206. (A) Structural model of the catalytic domain of IKB206. The model was built using the online available server Phyre2 (Kelley L A et al. 2015). Secondary structural elements are represented in light grey cartoon and the putative catalytic residues are represented in sticks. (B) Structural model of the D8 domain of IKB206. The model was built using the online available server Swissmodel (Waterhouse A et al. 2018). Secondary structural elements are represented in grey cartoon. (C) Structural and (D) sequence alignment of the catalytic residues of T4 lysozyme (Daopin S et al. 1991), DLP12 endolysin (Babu K et al. 2018), P22 lysozyme (Mooers B H et al. 2006) and AB 5075UW muramidase (Sykilinda N N et al. 2018) (PDB codes 1L48, 4ZPU, 2ANV and 6ET6 respectively). Catalytic residues superimposed to E15, D24 and T33 of IKB206 are represented in sticks (C) and marked with an asterisk (D).

FIG. 10: Bactericidal effect of IKB206AD8 on *E. coli* strain ATCC 25922. *E. coli* cultures were resuspended in buffer, adjusting the bacterial suspension to 105 colony forming units (CFU) mL$^{-1}$, and the cultures were incubated in the absence (buffer) or presence of the enzyme at 37° C. for 2 h. The data is representative of 3 independent experiments. Viable cells were determined by counting in LB agar plates. A) Bactericidal effect of expressed IKB206AD8 on the reduction of CFU mL$^{-1}$ over time in the presence of different enzyme concentrations. B) Bactericidal effect of expressed IKB206AD8 on the reduction of the number of logs over time in the presence of different enzyme concentrations. The error bars represent the standard error. The asterisks represent a significant difference (* P<0.05;  P<0.005; * P<0.0005) with respect to the control (buffer) according to: a one-way ANOVA test followed by a Tukey test in the case of samples showing a normal distribution and homoscedasticity; and a Kruskal Wallis test followed by the U-Mann Whitney test in the case of samples not showing a normal distribution or showing heterogeneity of variances.

FIG. 14: Synergy study using bacterial death studies. (A) Meropenem and IKB206$_{tags}$. (B) Imepenem and IKB206$_{tags}$.

DETAILED DESCRIPTION OF THE INVENTION

Definitions

Figure 2:
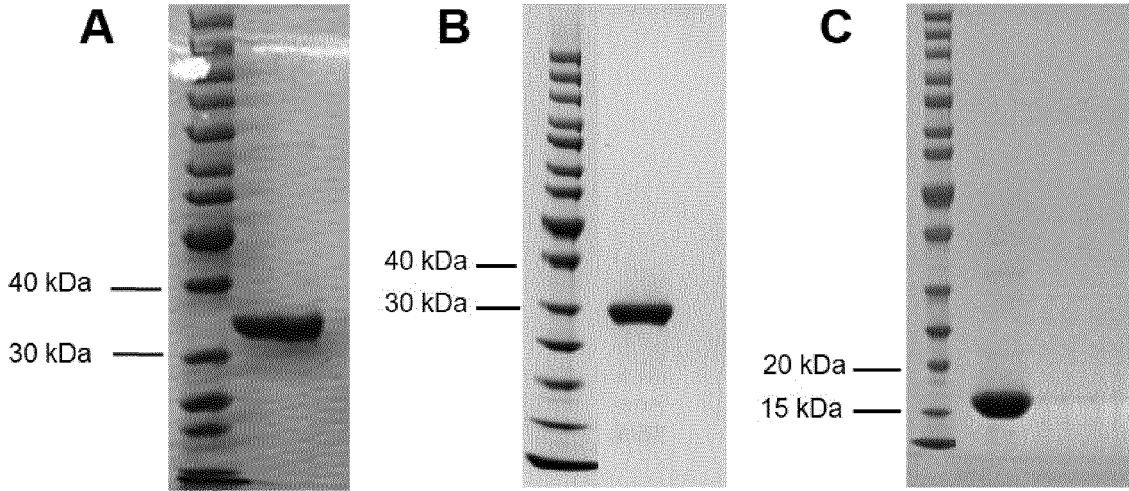
FIG. 2: A) 4-12% SDS-polyacrylamide gel electrophoresis of purified IKB206$_{tags}$, B) purified IKB206 and C) IKB206ΔD8.

A "polynucleotide" or "nucleic acid" sequence as used herein refers to a DNA or RNA sequence, preferably to a DNA sequence. The term captures sequences that include any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

A "coding sequence" or a sequence which "encodes" a gene product as used herein, refers to a nucleic acid sequence which is transcribed (in the case of DNA) and translated (in the case of mRNA), in vitro or in vivo when placed under the control of appropriate regulatory sequences.

The terms DNA "control sequences" and "control elements" as used herein, refer collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences/elements need always be present so long as the selected coding sequence is capable of being replicated, transcribed and translated in an appropriate host cell.

"Operably linked" as used herein refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "promoter" as used herein refers to a region of DNA that initiates transcription of a particular coding sequence. Promoters are located near the transcription start sites of genes, on the same strand and upstream on the DNA (towards the 5' region of the sense strand). Promoters can be about 100-1000 base pairs long. A "prokaryotic promoter" typically includes two short sequences at −10 and −35 positions upstream from the transcription start site. The sequence at −10 is called the Pribnow box, or the −10 element, and usually consists of the six nucleotides TATAAT. The Pribnow box is absolutely essential to start transcription in prokaryotes. The other sequence at −35 (the −35 element) usually consists of the six nucleotides TTGACA, and it controls the rate of transcription. Bacterial cells contain sigma factors which assist the RNA polymerase in binding to the promoter region. Common bacterial promoters are T7 (constitutive, promoter from T7 bacteriophage), Sp6 (constitutive, promoter from Sp6 bacteriophage), lac (constitutive in the absence of lac repressor, can be induced by IPTG or lactose), araBad (inducible by arabinose), trp (repressible by tryptophan) and Ptac (regulated like the lac promoter).

The term "amino acid" as used herein, includes the 20 common naturally occurring amino acids, seleno cysteine, pyrrolysine and "unnatural amino acids". The term "unnatural amino acid" as used herein refers to any other amino acid, modified amino acid, and/or amino acid analogue. Examples of unnatural amino acids include but are not limited to: a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl) alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,αdisubstituted amino acid; a β-amino acid; a cyclic amino acid other than proline or histidine, an aromatic amino acid other than phenylalanine, tyrosine or tryptophan, and/or the like.

The term "peptide linker", "linker" or "spacer" as used herein refers to a spacer acting as a hinge region between polypeptide domains, allowing them to move independently from one another while maintaining the three-dimensional form of the individual domains. In this sense, a preferred spacer would be a hinge region characterized by a structural ductility or flexibility allowing this movement. Typically, a peptide having structural flexibility (i.e., a flexible linking peptide or "flexible linker") comprises 2 or more amino acids selected from the group consisting of glycine, serine, alanine and threonine. Preferably, wherein at least 65%, preferably 70%, 75%, 80%, 85%, 90%, 95%, 96%, 97%, 98%, 99% or 100% of the amino acids in said flexible peptide linker are selected from the group consisting of glycine, serine, alanine and threonine. The spacer peptide may preferably contain repeats of amino acid residues, particularly Gly and Ser, or any other suitable repeats of amino acid residues. The length of the spacer can vary. Preferred ranges are from 2 to 30, preferably from 5 to 25, more preferably from 10 to 20 amino acids.

"Identity" as known in the art, is a relationship between two or more polypeptide sequences, as determined by comparing the sequences. "Identity" can be readily calculated by known algorithms well known in the art. Preferred methods to determine identity are designed to give the largest match between the sequences tested. Methods to determine identity are codified in publicly available computer programs. The percent identity between two sequences can be determined using analysis software {i.e. Sequence Analysis Software Package of the Genetics Computer Group, Madison Wis.) that incorporates the Needelman and Wunsch, (J. Mol. Biol., 48; 443-453, 1970) algorithm {e.g., NBLAST, and XBLAST).

Identity can be measured as "local identity" or "global identity". Local identity refers the degree of sequence relatedness between polypeptides/polynucleotides as determined by the match between strings of such sequences. Global identity refers to the degree of sequence relatedness of a polypeptide/polynucleotide compared to the full-length of a reference polypeptide/polynucleotide. Unless specified otherwise, as used herein identity means global identity.

The terms "subject", or "individual" are used herein interchangeably to refer to all the animals classified as mammals and includes but is not limited to domestic and farm animals, primates and humans, for example, human beings, non-human primates, cows, horses, pigs, poultry, sheep, goats, dogs, cats, or rodents. Preferably, the subject is a male or female human being of any age or race.

The term "treatment" encompasses both a prophylactic or therapeutic treatment. The term "therapeutic treatment" or "therapy" as used herein refers to bringing a body from a pathological state or disease back to its normal, healthy state. The term "prophylactic treatment" as used herein refers to preventing a pathological state. This treatment may be a combined treatment or therapy. Treatment also refers to reducing incidence, or alleviating symptoms, eliminating recurrence, preventing recurrence, preventing incidence, improving symptoms, improving prognosis or combinations thereof. "Treatment" further encompasses reducing the population, growth rate or virulence of the bacteria in the subject and thereby controlling or reducing a bacterial infection in a subject or bacterial contamination of an organ or tissue or environment. Thus "treatment" that reduces incidence is effective to inhibit growth of at least one Gram-negative bacterium in a particular milieu, whether it be a subject or an environment. On the other hand, "treatment" of an already established infection refers to reducing the population or killing, including even eradicating the Gram-negative bacteria responsible for an infection or contamination.

The term "combination therapy" as used throughout the specification, is meant to comprise the administration of the referred therapeutic agents to a subject, in the same or separate pharmaceutical formulations, and at the same time or at different times. If the therapeutic agents are administered at different times they should be administered sufficiently close in time to provide for the combined effect (e.g. potentiating or synergistic response) to occur.

The particular combination of therapies to employ in a combination regimen will take into account compatibility of the desired therapeutics and/or procedures and/or the desired therapeutic effect to be achieved. It will be appreciated that the therapies employed may achieve a desired effect for the same disorder, and/or they may achieve different effects (e.g., control of any adverse effects).

The term "single agent" as used herein relates to the use of an active ingredient sufficiently separate in time from another active ingredient to prevent for the potentiating or synergistic response to occur. More specifically, the use as "single agent" does not encompass the use as a "combination therapy".

The term "therapeutically effective amount" as used herein refers to an amount that is effective, upon single or multiple dose administration to a subject (such as a human patient) in the prophylactic or therapeutic treatment of a disease, disorder or pathological condition.

The term "bactericidal" in the context of an agent conventionally means having the property of causing the death of bacteria or capable of killing bacteria to an extent of at least a 3-log (99.9%) or better reduction among an initial population of bacteria.

The term "bacteriostatic" conventionally means having the property of inhibiting bacterial growth, including inhibiting growing bacterial cells, thus causing a 2-log (99%) or better and up to just under a 3-log reduction among an initial population of bacteria.

The term "antibacterial" in a context of an agent is used generically to include both bacteriostatic and bactericidal agents.

The term "drug resistant" in a context of a pathogen and more specifically a bacterium, generally refers to a bacterium that is resistant to the antimicrobial activity of a drug. When used in a more particular way, drug resistance specifically refers to antibiotic resistance. In some cases, a bacterium that is generally susceptible to a particular antibiotic can develop resistance to the antibiotic, thereby becoming a drug resistant microbe or strain. A "multi-drug resistant" pathogen is one that has developed resistance to at least two classes of antimicrobial drugs, each used as monotherapy. For example, certain strains of *E. coli* are capable of producing the so-called extended-spectrum beta-lactamases (ESBLs). ESBLs are enzymes that degrade certain antibiotics such as penicillins or cephalosporins, so the strains that produce these ESBLs are resistant to these antibiotics. In addition, strains of ESBLs-producing *E. coli* resistant to carbapenems have already been found, one of the few antibiotics effective against this to ESBLs-producing *E. coli*.

One skilled in the art can readily determine if a bacterium is drug resistant using routine laboratory techniques that determine the susceptibility or resistance of a bacterium to a drug or antibiotic.

The term "suitable" in the context of an antibiotic being suitable for use against certain bacteria refers to an antibiotic that was found to be effective against those bacteria even if resistance subsequently developed.

DETAILED DESCRIPTION

In a first aspect, the invention relates to a protein comprising:

a) amino acid sequence SEQ ID NO:1 or a variant sequence or fragment with at least 60% identity thereto, wherein said variant has conservative amino acid changes and said variant or fragment has at least 90% of the peptidoglycan hydrolase activity of SEQ ID NO:1; and wherein said protein does not consist of SEQ ID NO:1.

This includes for instance a chimeric protein including one or more cell wall binding domains (CBDs) known in the art. In a particular embodiment, said protein is a chimeric protein of the invention as described herein below.

Preferred features and embodiments relating to the protein, including SEQ ID NO: 1 variants and fragments thereof, are as described herein below for the chimeric protein of the invention.

In some embodiments, this protein comprises or consists of:

a) amino acid sequence SEQ ID NO:1 or a variant sequence or fragment with at least 80% identity thereto, wherein said variant has conservative amino acid changes and wherein said variant or fragment has residues corresponding to E15, D24, T33 and R139 of SEQ ID NO:1, and said variant or fragment has at least 90% of the peptidoglycan hydrolase activity of SEQ ID NO: 1; and wherein said protein does not consist of SEQ ID NO:1.

In other embodiments, this protein consists of a variant sequence or fragment with at least 60% identity to SEQ ID NO:1, wherein said variant has conservative amino acid changes and said variant or fragment has at least 90% of the peptidoglycan hydrolase activity of SEQ ID NO: 1.

In a second aspect, the present invention relates to a chimeric protein comprising:

a) a polypeptide comprising or consisting of amino acid sequence SEQ ID NO:1 or a variant sequence with at least 60% identity thereto, or a fragment of any thereof, wherein said variant has conservative amino acid changes and wherein said variant or fragment is a biologically active polypeptide. In particular, wherein said variant or fragment has at least 90%, preferably, at least 95%, more preferably at least 96%, 97%, 98%, 98%, 99% or 100% of the peptidoglycan hydrolase activity of SEQ ID NO: 1; and b) a polypeptide comprising or consisting of amino acid sequence SEQ ID NO:2 or a variant sequence with at least 60% identity thereto, or a fragment of any thereof, wherein said variant has conservative amino acid changes and wherein said variant or fragment is a biologically active polypeptide. In particular, wherein said variant or fragment has at least 90%, preferably, at least 95%, more preferably at least 96%, 97%, 98%, 98%, 99% or 100% of the cell permeating activity of SEQ ID NO: 2.

SEQ ID NO:1 corresponds to a putative endolysin (NCBI Reference Sequence: YP_009284326.1) of *Enterobacter* phage Arya (NCBI Reference Sequence NC_031048.1) and consists of the following amino acid sequence:

```
  1 mktspngiav tkyfesfear aypdpatggk pytigfgttv ypsgapvrlg dvctkeqaek 61 ylqndlakfe kivsdavrvp inqgqfdalv sftynlgpan lrsstllkkl nagdyagaak 121 efprwnrang kvmkgltrrr aaeqclfegm ggasaiergv aaa
```

SEQ ID NO:1 has peptidoglycan (PG) hydrolase activity, determined by turbidometric assays. More specifically, by sequence homology, it would correspond to a lysozyme.

A person skilled in the art, will know how to determine presence of PG hydrolase activity. For instance, PG hydrolase activity can be determined by zymography or by turbidometric assays which follow the activity of the enzyme in *Micrococcus* lysodeikticus cells (Santin and Cascales, 2017), for illustrative purposes see the turbidometric assay protocol described in the examples. In addition, there are fluorescence assays where the PG is labeled with fluorescence, which can only be detected once the enzyme has acted (Invitrogen EnzChek® lysozyme Assay kit). However, these assays only indicate a PG hydrolase activity. To determine the cutting sites, more precise approaches such as reverse-phase high-performance liquid chromatography coupled to mass spectrometry are needed (Santin and Cascales, 2017). In particular embodiments, said variant or fragment of SEQ ID NO:1 has at least 90%, preferably, at least 95%, more preferably at least 96%, 97%, 98%, 98%, 99% or 100% of the PG hydrolase activity of SEQ ID NO: 1.

SEQ ID NO:2 corresponds to a cell permeability domain (D8) of the lytic enzyme Lys1521 (D1) of *B. amylolique-faciens* phage (Morita, M. et al. 2001) (GenBank: AAK40280.1) and consists of the following amino acid sequence:

```
143                          nsgtpknv srgtsstktt pkykvkngdn itkiakkhnt 181 tvatllklnp gikdpnmirv gqtlnvtgsg gkthkvksgd tlskiavdnk ttvsklmnln 241 peitnpnhik vgqtirls
```

The polypeptide having amino acid sequence SEQ ID NO:2 was previously described to have cell permeating activity (Orito et al. 2004).

It has previously been reported that helix-forming amphipathic peptides containing basic amino acid residues seem to interact with negatively charged membrane elements, i.e. LPS in Gram-negative bacteria (Düring, K., et al. 1999). Morita et al. (Morita et al. 2001) reported that based on the predicted secondary structure, there are two helical peptides in the C-terminus of endolysin: one exists in the D9 region (aa 171-177 of D1, corresponding to aa 29-35 of SEQ ID NO:2) and the other in the D10 region (aa 212-216 of D1, corresponding to aa 70-74 of SEQ ID NO:2) and suggest that these peptides may bind to the LPS of *P. aeruginosa* PAO1 strain. Moreover, the structural model of the D8 cell permeability domain (SEQ ID NO:2) was found by the inventors to show a structural similarity with the LysM domain of a putative endopeptidase of *Termus thermofilus* (Wong J E et al. 2015), see Example 7. LysM domains in bacterial proteins are usually repetitive entities known to interact with substrates containing N-acetylglucosamine such as the peptidoglycan. Thus, without willing to be bound by theory, this data suggests that D8 may be involved in the binding to the enzyme substrate.

A person skilled in the art, will know how to determine presence of outer membrane permeating activity. For instance, the ability of an endolysin to permeabilize the outer membrane of a Gram-negative bacteria, can be assessed by examining the release of the periplasmic B-lactamase of *Pseudomonas aeruginosa* PAO1 after the treatment of the cells of said bacterium with the enzyme to be studied, as described in Orito et al., 2004 and reproduced herein below for illustrative purposes.

An overnight culture of *P. aeruginosa* PAO1 (500 µl) is diluted with 30 ml of pre-warmed (37° C.) LB medium and incubated with shaking (150 rpm) for 2 h at 37° C. Following the addition of 0.25 mg l$^{-1}$ imipenem to induce β-lactamase production, the cultures are incubated with shaking for an additional 3 h and harvested by centrifugation at 5,000 g for 10 min at room temperature. Cell pellets are washed once with PBS and resuspended PBS to a final volume of 10 ml. Endolysins are added to the cell suspensions (25 µl) at final concentrations of 40 µg ml$^{-1}$ and 200 µg ml$^{-1}$ (total volume, 50 µl). The mixture is incubated at 37° C. for 10 min and centrifuged in an Eppendorf tube at 15,000 g for 30 min at room temperature. The control experiment condition can be performed using the supernatant of sonicated *P. aeruginosa* PAO1 cells. The supernatants are collected and B-lactamase activity is assayed using 100 µM chromogenic cephalothin (CENTA) as substrate. The hydrolysis of CENTA can be monitored by continuously recording the absorbance at 405 nm. Release of β-lactamase (percent) is defined as the ratio of the β-lactamase activity under the control condition to that under the test condition.

In particular embodiments, said variant or fragment of SEQ ID NO:2 has at least 90%, preferably, at least 95%, more preferably at least 96%, 97%, 98%, 98%, 99% or 100% of the cell permeating activity of SEQ ID NO:2.

In some embodiments, said chimeric protein comprises or consists of:

a) a polypeptide comprising or consisting of amino acid sequence SEQ ID NO:1; and b) a polypeptide comprising or consisting of amino acid sequence SEQ ID NO:2.

The polypeptide in (b) may be fused directly in-line or through a peptide linker at the C-terminal end of the polypeptide in (a). Preferably, the polypeptide in (b) is fused directly at the C-terminal end of the polypeptide in (a).

In preferred embodiments, said chimeric protein has bacteriostatic or bactericidal activity against Gram-negative bacteria, as defined herein, preferably bactericidal activity against Gram-negative bacteria.

In some embodiments, said chimeric protein comprises or consists of amino acid sequence SEQ ID NO:3 (which corresponds to SEQ ID NO:2 fused directly at the C-terminal end of SEQ ID NO:1) or a variant sequence with at least 60% identity thereto, or a fragment of any thereof, wherein said variant has conservative amino acid changes, and wherein said variant or fragment is biologically active. In particular, wherein said variant or fragment has at least 90%, preferably, at least 95%, more preferably at least 96%, 97%, 98%, 98%, 99% or 100% of the bactericidal or bacteriostatic activity of SEQ ID NO:3 against Gram-negative bacteria.

A chimeric protein as described herein has been shown by the inventors to be highly effective in inhibiting the growth, reducing the population, or killing Gram-negative bacteria, in particular in bacteria of the genus *Acinetobacter* (e.g., *A. baumannii*), *Pseudomonas* (*P. aeruginosa*), *Escherichia* (e.g., *E. coli*) and *Klebsiella* (e.g., *K. pneumoniae*) (see Examples 4 and 6). Assays for analyzing bactericidal activity of a compound are well known in the art and described for instance by Loessner et al. (Loessner, M. J. et al. 2002) and Schmelcher et al. (Schmelcher, M. et al. 2010). For instance, to quantify the bactericidal effect of the antimicrobial agent, a bacterial suspension having for example an absorbance at 600 nm (A$_{600}$) of 0.3 is incubated at 37° C. in the presence of the agent at a range of doses to be tested. Samples are taken at different times, serial dilutions are performed, and these are seeded in plates containing culture medium to determine viable bacteria. The bactericidal effect is quantified as the number of logs reduced in the presence of treatment, after a given incubation time ($\log_{10}$ (N$_0$/N$_i$), where N$_0$=number of CFU mL$^{-1}$ before treatment, and N$_i$=number of CFU mL$^{-1}$ after the corresponding incubation time in the presence of each treatment. The bacterial suspension can be incubated with the antimicrobial agent in a culture medium or a buffer solution, such as PBS or another water-based salt solution. The specific assay used for determining IKB206 bactericidal activity is described in the Examples.

In preferred embodiments, said bacteriostatic or bactericidal effect is achieved in an in vitro assay after 120 minutes of incubation with the bacteria, preferably after 90 minutes, more preferably after 60 minutes, even more preferably after 30 minutes, after 15 minutes, such as after 10 minutes or less, including after 9, 8, 7, 6, 5,4, 3, 2, or 1 minutes; wherein the starting concentration of Gram-negative bacteria (e.g. *E. coli*) in the bacterial culture corresponds to an A$_{600}$ of 0.3. The absorbance levels may for instance be determined with a Spectrostar Nano spectrophotometer (BMG labtech).

Also in preferred embodiments, bacteriostatic or bactericidal effect is achieved in an in vitro assay at a concentration of the chimeric protein of the invention of less than 60 µg mL$^{-1}$, preferably of 55 µg mL$^{-1}$, 50 µg mL$^{-1}$, 45 µg mL$^{-1}$, 40 µg mL$^{-1}$, 35 µg mL$^{-1}$, 30 µg mL$^{-1}$, 25 µg mL$^{-1}$, 20 µg mL$^{-1}$, 15 µg mL$^{-1}$, 10 µg mL$^{-1}$, 9 µg mL$^{-1}$, 8 µg mL$^{-1}$, 7 µg mL$^{-1}$,6 µg mL$^{-1}$ or of 5 µg mL$^{-1}$; wherein the starting concentration of Gram-negative bacteria (e.g. *E. coli*) in the bacterial culture corresponds to an A$_{600}$ of 0.3. The absorbance levels may for instance be determined with a Spectrostar Nano spectrophotometer (BMG labtech).

This bacteriostatic or bactericidal effect is preferably a bactericidal effect. In preferred embodiments, the bactericidal effect is of at least a 4-log reduction among an initial population of bacteria, preferably of at least a 5-log reduction, of at least 6-log, of at least 7-log or better reduction.

In more preferred embodiments, a bactericidal effect is achieved in an in vitro assay at a concentration of 15 µg mL$^{-1}$ after 30 minutes of incubation with the bacteria, more preferably after 15 minutes of incubation; wherein the starting concentration of Gram-negative bacteria (e.g. *E. coli*) in the bacterial culture corresponds to an A$_{600}$ of 0.3. The absorbance levels may for instance be determined with a Spectrostar Nano spectrophotometer (BMG labtech).

In another preferred embodiment, a bacteriostatic effect is achieved in an in vitro assay at a concentration of 15 µg mL$^{-1}$ after 10 minutes of incubation with the bacteria, more preferably after 5 minutes, even more preferably after 4, 3, 2, or 1 minutes; wherein the starting concentration of Gram-negative bacteria (e.g. *E. coli*) in the bacterial culture corresponds to an A$_{600}$ of 0.3. The absorbance levels may for instance be determined with a Spectrostar Nano spectrophotometer (BMG labtech).

In some embodiments, said polypeptide with at least 60% identity, has preferably at least 65%, at least 70%, at least 75%, at least 80%, at least 85%, at least 87%, at least 90%, at least 91%, at least 92%, at least 93%, at least 94%, at least 95%, at least 96%, at least 97%, at least 98% or most preferably at least 99% identity to the corresponding sequence.

In obtaining variant biologically active polypeptides and the respective coding sequences, those of ordinary skill in the art will recognize that the polypeptides may be modified by certain amino acid substitutions, additions, deletions, and post-translational modifications, without loss or reduction of biological activity. In particular, it is well-known that conservative amino acid substitutions, that is substitution of one amino acid for another amino acid of similar size, charge, polarity and conformation, is unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

In general, preparation of the chimeric protein of the invention can be accomplished by procedures disclosed herein and by recognized recombinant DNA techniques involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, culturing of the host. Additionally, the fusion molecules can be isolated and purified using chaotropic agents and well known electrophoretic, centrifugation and chromatographic methods. See generally, Sambrook et al., Molecular Cloning: A Laboratory Manual (2nd ed. (1989); and Ausubel et al., Current Protocols in Molecular Biology, John Wiley & Sons, New York (1989) for disclosure relating to these methods.

The protein or polypeptides of the present invention can be prepared with one or more amino acid substitutions, deletions or additions as compared to SEQ ID NO:1, SEQ ID NO:2 or SEQ ID NO:3. These changes are preferably of a minor nature, that is, conservative amino acid substitutions and other changes that do not significantly affect the folding or activity of the protein or polypeptide, and include amino- or carboxyl-terminal extensions, such as an amino-terminal methionine residue, a small linker peptide of up to about 20-25 residues, or may include tags to facilitate modification, identification and/or purification of the fusion protein. Two or more tags (e.g., affinity tags to facilitate purification) may be used in combination. Polypeptides comprising affinity tags can further comprise a polypeptide linker and/or a proteolytic cleavage site between the polypeptide and the affinity tag.

As discussed in Example 7, the inventors have studied the mechanism of action of the chimeric protein of the invention. The structural model of the catalytic domain revealed an overall fold similar to the T4 lysozyme and other T4 lysozyme-like endolysins such us P22 phage lysozyme (Mooers B H et al. 2006) or the endolysin encoded by the *Escherichia coli* DLP12 prophage (Babu K et al. 2018). Based on sequence alignment (FIG. 9, D) and structural superimposition of the structural model of IKB206 against the crystal structures of these endolysins (FIG. 9, C) the inventors propose that the catalytic domain of IKB206 belongs to the T4 lysozyme-like endolysins and residues E15, D24 and T33 form the catalytic triad of the enzyme. Moreover, they suggest that R139 may form a salt bridge with E15.

In some embodiments, variants of SEQ ID NO:1 or SEQ ID NO:3 are characterized by having conservative amino acid changes and in variants or fragments residues corresponding to E15, D24, and T33 of SEQ ID NO:1 or SEQ ID NO:3, respectively are maintained. In some embodiments, amino acid changes are conservative and the residues corresponding to positions 12 to 35 or even 12 to 54 of SEQ ID NO:1 or SEQ ID NO:3, respectively, remain unamended. In addition, in some embodiments, in combination with any of the foregoing the amino acid corresponding to R139 of SEQ ID NO:1 or SEQ ID NO:3, respectively, remains unamended, e.g., residues corresponding to E15, D24, T33 and R139 remain unamended.

In some embodiments, variants of SEQ ID NO:2 are characterized by having conservative amino acid changes and in variants or fragments amino acids corresponding to positions 29- and 70-74 of SEQ ID NO: 2 are maintained.

In a particular embodiment, the present invention relates to a chimeric protein comprising:
a) a polypeptide comprising amino acid sequence SEQ ID NO:1 or a variant sequence or fragment with at least 80% identity thereto, wherein said variant is characterized by having conservative amino acid changes, and wherein said variant or fragment has residues corresponding to E15, D24, T33 and R139 of SEQ ID NO:1, and preferably has at least 90% of the peptidoglycan hydrolase activity of SEQ ID NO:1; and
b) a polypeptide comprising amino acid sequence SEQ ID NO:2 or a variant sequence or fragment with at least 80% identity thereto, wherein said variant is characterized by having conservative amino acid changes and wherein said variant or fragment has amino acids corresponding to positions 29-35 and 70-74 of SEQ ID NO: 2 and preferably has at least 90% of the cell permeating activity of SEQ ID NO:2;
wherein the polypeptide in (b) is fused directly or through a peptide linker at the C-terminal end of the polypeptide in (a).

In another embodiment, it relates to a chimeric protein comprising or consisting of amino acid sequence SEQ ID NO:3 or a variant sequence or fragment with at least 80% identity thereto, wherein said variant is characterized by having conservative amino acid changes, and wherein said variant or fragment has residues corresponding to E15, D24, T33 and R139 of SEQ ID NO:3, and preferably has at least 90% of the bacteriostatic or bactericidal activity of SEQ ID NO:3 against Gram-negative bacteria.

The protein or polypeptides may comprise a specific affinity purification tag. Illustrative, non-limiting examples of affinity tags include glutathione S-transferase (GST), maltose E binding protein, protein A, FLAG tag, hexa-histidine, myc tag or the influenza HA tag. Said affinity purification tag can be fused directly in-line or, alternatively, fused to the polypeptide via a cleavable linker, i.e., a peptide segment containing an amino acid sequence that is specifi-cally cleavable by enzymatic or chemical means (i.e., a recognition/cleavage site). When the affinity tag is directly fused, it joins the reading frame of the peptide of interest to the reading frame of the gene encoding the affinity tag such that a translational fusion is generated. In a particular embodiment, said cleavable linker comprises an amino acid sequence which is cleavable by a protease such as an enterokinase, Arg-C endoprotease, Glu-C endoprotease, Lys-C endoprotease, factor Xa, furin-like proprotein con-vertase, thrombin, etc.; alternatively, in another particular embodiment, said cleavable linker comprises an amino acid sequence which is cleavable by a chemical reagent, such as, for example, cyanogen bromide which cleaves methionine residues, or any other suitable chemical reagent. The cleav-able linker is useful if subsequent removal of the affinity purification tags is desirable.

In some embodiments, the chimeric protein of the inven-tion further comprises a recognition/cleavage site down-stream from peptide (b). In a particular embodiment, said cleavage site is thrombin cleavage site (e.g. amino acid sequence SEQ ID NO: 4).

In some preferred embodiments, the chimeric protein of the invention comprises or consists of a polypeptide of amino acid sequence SEQ ID NO: 5. A chimeric protein which consists of amino acid sequence SEQ ID NO:5 is the result of the fusion of SEQ ID NO:1 and SEQ ID NO: 2, wherein SEQ ID NO:2 is directly fused at the C-terminal end of SEQ ID NO: 1 (SEQ ID NO: 3) further to its cloning and expression in the pET29b+vector. This protein is character-ized by further presenting an S-tag at the N-terminal end and a 6-His tag at the C-terminal end; and further comprising at both ends a cleavage site for thrombin (SEQ ID NO: 4) and 3 extra amino acids (to improve thrombin cleavage effi-ciency) between the tags and SEQ ID NO:3, resulting in a chimeric protein with 329 amino acids referred as IKB206$_{tags}$. For illustrative non-limiting purposes, a sche-matic representation of IKB206 and IKB206$_{tags}$ is provided in FIG. 1 (A and B).

In further embodiments, optionally in combination with one or more of the embodiments and features described herein, the chimeric protein of the invention may comprise a further peptide with OM permeabilizing or destabilizing properties (such as a polycationic peptide). In a preferred embodiment it does not comprise another peptide with OM permeabilizing or destabilizing properties (such as a poly-cationic peptide).

In still a further embodiments, optionally in combination with one or more of the embodiments and features described herein, the chimeric protein of the invention may comprise a further domain with antimicrobial activity. In preferred embodiments, it does not comprise a further domain with antimicrobial activity.

In some embodiments, the chimeric protein of the inven-tion may be chemically modified. A chemical modification includes but is not limited to, adding chemical moieties, creating new bonds, and removing chemical moieties. Chemical modifications can occur anywhere in the polypep-tide, including the amino acid side chains, as well as the amino or carboxyl termini. Such modification can be present at more than one site in the polypeptide. Furthermore, one or more side groups, or terminal groups of the polypeptide may be protected by protective groups known to the person ordinarily-skilled in the art.

Also, in some embodiments, the chimeric protein of the invention may contain an attachment of duration enhancing moieties. A non-limiting example of duration enhancing moiety is polyethylene glycol. Polyethylene glycol ("PEG") has been used in the art to obtain therapeutic polypeptides of enhanced duration (Zalipsky, S., *Bioconjugate Chemistry*, 6:150-165 (1995); Mehvar, R., *J. Pharm. Pharmaceut. Set*, 3:125-136 (2000)). The PEG backbone [(CH2CH2—O—)$_n$; n: number of repeating monomers] is flexible and amphi-philic. When attached to another chemical entity, such as the chimeric protein of the invention, PEG polymer chains can protect such polypeptide from immune response and other clearance mechanisms. As a result, pegylation can lead to improved efficacy and safety by optimizing pharmacokinet-ics, increasing bioavailability, and decreasing immunoge-nicity and dosing amount and/or frequency.

The protein (including the chimeric protein) of the inven-tion can be used alone or in combination with permeabiliz-ing or disrupting agents of the outer membrane of the Gram-negative bacteria, including, but not limited to metal chelators as e.g. EDTA, TRIS, lactic acid, lactoferrin, poly-myxins, citric acid (Vaara M. *Microbiol Rev.* 56 (3): 395-441 (1992)). These permeabilizing agents can be part of the same or different compositions. In preferred embodiments, the protein (including the chimeric protein) is used without permeabilizing agents.

In a third aspect, the invention relates to a polynucleotide comprising a nucleic acid molecule encoding a protein (including a chimeric protein) as described herein.

In some embodiments, said polynucleotide comprises:
a) a nucleic acid sequence comprising or consisting of SEQ ID NO: 6 or a variant sequence with at least 70% identity thereto, or a fragment of any thereof, wherein said variant sequence or fragment encodes a biologi-cally active polypeptide.

```
                                      SEQ ID NO: 6
atgaaaacctctccaaatggtatcgccgttaccaa gtacttcgaatcatttgaagcccgcgcataccctg accccgccactggcggtaaaccatacacgattggc ttcggaaccactgtctacccgtctggcgcacccgt ccgtttaggggatgtgtgtacgaaagaacaggccg agaaatatttacaaaatgacttggcgaaattcgag aagattgtatctgacgcagtgcgcgttccccttaa tcaaggtcagtttgacgcgttagtgtcatttacgt ataacttaggacccgccaatttgcgcagcagtacc
```

-continued

```
ctgttaaaaaagttgaacgctggggactatgcggg ggccgctaaagagtttccgcgttggaaccgtgcaa acggtaaagtgatgaaaggtttgacacgtcgccgc gcggcagaacaatgtttgtttgaagggatgggagg cgcgagcgcgattgaacgtggtgtagccgctgca
```

In other embodiments, said polynucleotide comprises:

a) a nucleic acid sequence comprising or consisting of SEQ ID NO: 6 or a variant sequence with at least 70% identity thereto, or a fragment of any thereof, wherein said variant sequence or fragment encodes a biologically active polypeptide; and b) a nucleic acid sequence comprising or consisting of SEQ ID NO: 7 or a variant sequence with at least 70% identity thereto, or a fragment of any thereof, wherein said variant sequence or fragment encodes a biologically active polypeptide.

```
                                   SEQ ID NO: 7
aacagtgggacaccaaagaatgtttcccgcggaac ctcgtccacgaagacaacacctaagtataaggtaa aaaatggtgacaacttaactaaaatcgcgaagaaa cataatactacagtagcgacattgctgaaacttaa tccagggatcaaagaccccaacatgattcgtgtag ggcagactttaaatgttacagggtccggtgggaaa actcataaagtcaagtcgggtgacacactgagtaa aatcgcagttgataataagacgactgttagcaagt tgatgaatcttaacccggaaatcactaatcctaac catatcaaagtcggccagacaatccgtttgagc.
```

In preferred embodiments, said polynucleotide comprises:

a) a nucleic acid sequence comprising or consisting of SEQ ID NO: 6 or a variant sequence with at least 70% identity thereto, or a fragment of any thereof, wherein said nucleic acid sequence encodes SEQ ID NO:1, or a variant or fragment thereto as defined herein; and b) a nucleic acid sequence comprising or consisting of SEQ ID NO: 7 or a variant sequence with at least 70% identity thereto, or a fragment of any thereof, wherein said nucleic acid sequence encodes SEQ ID NO:2, or a variant or fragment thereto as defined herein.

In further embodiments, said polynucleotide comprises or consists of SEQ ID NO: 8 or a variant sequence with at least 70% identity thereto, or a fragment of any thereof, wherein said variant sequence or fragment encodes a biologically active polypeptide.

```
                                   SEQ ID NO: 8
atgaaaacctctccaaatggtatcgccgttaccaa gtacttcgaatcatttgaagcccgcgcatacccctg accccgccactggcggtaaaccatacacgattggc ttcggaaccactgtctacccgtctggcgcacccgt
```

-continued

```
ccgtttaggggatgtgtgtacgaaagaacaggccg agaaatatttacaaaatgacttggcgaaattcgag aagattgtatctgacgcagtgcgcgttccccttaa tcaaggtcagtttgacgcgttagtgtcatttacgt ataacttaggacccgccaatttgcgcagcagtacc ctgttaaaaaagttgaacgctggggactatgcggg ggccgctaaagagtttccgcgttggaaccgtgcaa acggtaaagtgatgaaaggtttgacacgtcgccgc gcggcagaacaatgtttgtttgaagggatgggagg cgcgagcgcgattgaacgtggtgtagccgctgcaa acagtgggacaccaaagaatgtttcccgcggaacc tcgtccacgaagacaacacctaagtataaggtaaa aaatggtgacaacttaactaaaatcgcgaagaaac ataatactacagtagcgacattgctgaaacttaat ccagggatcaaagaccccaacatgattcgtgtagg gcagactttaaatgttacagggtccggtgggaaaa ctcataaagtcaagtcgggtgacacactgagtaaa atcgcagttgataataagacgactgttagcaagtt gatgaatcttaacccggaaatcactaatcctaacc atatcaaagtcggccagacaatccgtttgagc
```

In preferred embodiments, said polynucleotide comprises a nucleic acid sequence comprising or consisting of SEQ ID NO: 8 or a variant sequence with at least 70% identity thereto, or a fragment of any thereof, wherein said nucleic acid sequence encodes SEQ ID NO: 3, or a variant or fragment thereto as defined herein.

In still further embodiments, said polynucleotide comprises or consists of SEQ ID NO: 9 or a variant sequence with at least 70% identity thereto, or a fragment of any thereof, wherein said sequence encodes a biologically active polypeptide.

```
                                   SEQ ID NO: 9
atgaaagaaaccgctgctgctaaattcgaacgcca gcacatggacagcccagatctgggtaccctggtgc cacgcggttccatggcgatatcggatccgatgaaa acctctccaaatggtatcgccgttaccaagtactt cgaatcatttgaagcccgcgcataccctgaccccg ccactggcggtaaaccatacacgattggcttcgga accactgtctacccgtctggcgcacccgtccgttt aggggatgtgtgtacgaaagaacaggccgagaaat atttacaaaatgacttggcgaaattcgagaagatt gtatctgacgcagtgcgcgttcccttaatcaagg tcagtttgacgcgttagtgtcatttacgtataact taggacccgccaatttgcgcagcagtaccctgtta
```

-continued

```
aaaaagttgaacgctggggactatgcgggggccgc taaagagtttccgcgttggaaccgtgcaaacggta aagtgatgaaaggtttgacacgtcgccgcgcggca gaacaatgtttgtttgaagggatgggaggcgcgag cgcgattgaacgtggtgtagccgctgcaaacagtg ggacaccaaagaatgtttcccgcggaacctcgtcc acgaagacaacacctaagtataaggtaaaaaatgg tgacaacttaactaaaatcgcgaagaaacataata ctacagtagcgacattgctgaaacttaatccaggg atcaaagaccccaacatgattcgtgtagggcagac tttaaatgttacagggtccggtgggaaaactcata aagtcaagtcgggtgacacactgagtaaaatcgca gttgataataagacgactgttagcaagttgatgaa tcttaacccggaaatcactaatcctaaccatatca aagtcggccagacaatccgtttgagcctgggtacc ctggtgccacgcggttccctcgagcaccaccacca ccaccac
```

In preferred embodiments, said polynucleotide comprises a nucleic acid sequence comprising or consisting of SEQ ID NO: 9 or a variant sequence with at least 70% identity thereto, or a fragment of any thereof, wherein said nucleic acid sequence encodes SEQ ID NO: 5 or a variant or fragment thereto as defined herein.

Preferably, said nucleic acid sequence with at least 70% identity has at 75%, at least 80%, at least 85%, at least 87%, at least 90%, at least 91%, at least 92%, at least 93%, at least 94%, at least 95%, at least 96%, at least 97%, at least 98% or most preferably at least 99% identity to SEQ ID NO:6, SEQ ID NO:7, SEQ ID NO:8 or SEQ ID NO:9, respectively.

In some embodiments, said polynucleotide comprises nucleic acid sequences (a) and (b) above, preferably said polynucleotide is selected from SEQ ID NO: 8 and SEQ ID NO:9; or a sequence with at least 70% identity thereto, wherein said sequence encodes a biologically active polypeptide, and said polynucleotide is operably linked to control sequences. Preferably, said polynucleotide is operably linked to at least one promoter, preferably to a prokaryotic promoter, i.e., which enables the expression of the inserted coding sequence in prokaryotic cells, for instance, in bacterial cells. In a particular embodiment, said polynucleotide is a vector.

In a fourth aspect, the present invention further relates to a vector comprising a polynucleotide as described herein. By "vector" is meant any genetic element, such as a plasmid, phage, hybrid vector, transposon, cosmid, chromosome, virus, virion, etc., which is capable of replication when associated with the proper control elements and which can transfer gene sequences between cells. The sequence encoding a peptide described herein can be inserted into a vector capable of delivering and maintaining the nucleic acid molecule in a bacterial cell. The polynucleotide may be inserted into an autonomously replicating vector. The vector may be a bacterial vector such as pET29b+, pGEM3Z and pcDNA3, and derivatives thereof; or bacteriophage DNA vector such as bacteriophage lambda or M13 and derivatives thereof. Preferably, said vector is a bacterial plasmid. The plasmids may be extrachromosomal plasmids or integrative plasmids, preferably extrachromosomal plasmids.

Said vector also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence). The vector can be capable of autonomous replication or it can integrate into host DNA to ensure stability during peptide production.

Expression vectors comprising inducible promoters commonly comprise an operator sequence. Operator sequences which may be employed are well known in the art and include lac, gal, deo, gin, raf, rha, araC, fru and mel. One or more perfect palindrome operator sequences may be employed. In certain embodiments, an operator sequence overlaps with the transcriptional start point. It will be recognised that the operator system is commonly employed with an appropriate repressor sequence. Repressor sequences produce repressor protein, for example lacl gene sequence when using the lac operators. Other lac repressor sequences may also be used, for example the laclq sequence can be used to increase the level of lac repressor protein. The repressor sequence may also be provided by the host cell genome or by using an additional compatible plasmid.

Expression may be induced by the addition of an inducer such as isopropyl-β-D-1-thiogalactopyranoside (IPTG), analogues of IPTG such as isobutyl-C-galactoside (IBCG), lactose or melibiose. Other inducers may be used and are described more fully elsewhere (e.g. see The Operon, eds Miller and Renznikoff (1978)). Inducers may be used individually or in combination. The construction of appropriate plasmids or expression vectors will be apparent to the scientist of ordinary skill.

Construction of a vector containing a nucleic acid described herein can be followed by transformation of a host cell. The introduction may employ any available technique. For bacterial cells, suitable techniques may include thermic shock, calcium chloride transformation, electroporation and transfection using bacteriophage.

In a fifth aspect, the present invention refers to a host cell comprising a vector as described herein. Preferably, said host cell is a prokaryotic host cell. Examples of prokaryotic cells include bacterial cells, for example Gram-negative bacterial cells, including *E. coli, Salmonella typhimurium, Serratia marsescens, Pseudomonas putida* and *Pseudomonas aeruginosa*, and Gram-positive bacterial cells including *Bacillus subtilis*. Preferred host cells are bacteria, particularly enterobacteriacae, preferably *E coli*, including B or K12 strains thereof. Most preferably, said host cell is *Escherichia coli* BL21 (DE3).

The introduction of the nucleic acid into the cells may be followed by causing or allowing expression from the nucleic acid, e.g., by entering host cells under conditions for expression of the polynucleotide. Typically, cells are cultured in a cell culture medium under appropriate temperature and atmosphere conditions (e.g. at 37° C.). Depending on the host cell, this culture media may be a "microbiological media" which refers to any suitable substrate for the growth and reproduction of microorganisms, such as bacteria or fungi. The most common growth media for microorganisms are nutrient broths (liquid nutrient medium) or LB medium (lysogeny broth). Liquid media are often mixed with agar and poured via a sterile media dispenser into Petri dishes to solidify. A person skilled in the art will understand that the term "microbiological media" encompasses solid plated media, as well as semi-solid and liquid microbial growth systems.

In a sixth aspect, the invention relates to a method for producing a protein (including a chimeric protein) of the invention, wherein said method comprises:

i. introducing a vector comprising a polynucleotide as described herein into an appropriate host cell;

ii. culturing the host cell under conditions suitable for the expression of said protein, iii. optionally, isolating and/or purifying said protein.

A person skilled in the art will know the most appropriate culture conditions according to the host cell. Examples of host cells and methods of culturing thereof have been provided above.

Methods for polypeptide isolation and/or purification are well known in the art (see for instance, Isolation and Purification of Proteins, Feb. 5, 2003 by CRC Press, ISBN 9780824707262). Procedures for purification of polypeptides initially depend on the site of expression of the protein. Some proteins are secreted into the cell culture media; others are intracellular proteins. In the second instance, the first step of a purification process involves lysis of the cell, which can be done by a variety of methods, including mechanical shear, osmotic shock, or enzymatic treatments. Optionally, cell debris is removed by differential centrifugation or by filtration.

Once a clarified solution containing the polypeptide of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. Affinity chromatography, which exploits a specific interaction between the protein to be purified and an immobilized capture agent, may also be an option for some polypeptides. For instance, when the protein as described herein contains tags, affinity chromatography may be used for its purification. In other embodiments, when the protein does not contain tags, cation exchange preferably followed by size exclusion chromatography may be used.

The protein (including a chimeric protein) of the invention can also be produced in protein expression systems other than bacteria, including baculovirus expression systems using *Drosophila* Sf9 cells, yeast or filamentous fungal expression systems, mammalian cell expression systems.

In addition, the protein (including a chimeric protein) and polypeptides described herein can be synthesized by the solid-phase method using an automated peptide synthesizer. For example, the peptide can be synthesized on Cyc (4-CH2 Bxl)-OCH2-4-(oxymethyl)-phenylacetamidomethyl resin using a double coupling program. Peptides can also be synthesized by many other methods including solid phase synthesis using traditional FMOC protection (i.e., coupling with DCC-HOBt and deprotection with piperidine in DMF).

In a seventh aspect, the present invention relates to a composition comprising a protein (including a chimeric protein), a polynucleotide, a vector or a host cell as described herein.

Appropriate amounts of a protein (including a chimeric protein), a polynucleotide, a vector or a host cell as described herein can be formulated with pharmaceutically acceptable excipients, vehicles and/or carriers to obtain a pharmaceutical composition. Preferably, said pharmaceutical composition comprises a protein (including a chimeric protein), polynucleotide or expression vector as described herein.

The phrases "pharmaceutically acceptable" refers to molecular entities and compositions that do not produce adverse, allergic, or other untoward reactions when administered to an animal or a human. As used herein, "pharmaceutically acceptable excipients, vehicles and/or carriers" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the agents according to the invention, e.g., chimeric protein of the invention.

In a eight aspect, the present invention provides a protein (including a protein consisting of amino acid sequence SEQ ID NO:1, a protein and a chimeric protein as described herein), a polynucleotide, a vector or a host cell or a pharmaceutical composition as described herein (hereinafter generically referred as "an agent according to the invention) for use in the prophylactic and/or therapeutic treatment of a bacterial infection caused by Gram-negative bacteria.

In an ninth aspect, the present invention pertains to the use of a protein (including a protein consisting of amino acid sequence SEQ ID NO:1, a protein and a chimeric protein as described herein), a polynucleotide, a vector, a host cell or a pharmaceutical composition as described herein in the manufacturing a medicament for the prophylactic and/or therapeutic treatment of a bacterial infection caused by Gram-negative bacteria.

In a tenth aspect, the present invention refers to a method for the prophylactic and/or therapeutic treatment of a bacterial infection caused by Gram-negative bacteria comprising administering to a subject diagnosed with, at risk for, or exhibiting symptoms of a bacterial infection, a composition containing an effective amount of a protein (including a protein consisting of amino acid sequence SEQ ID NO:1, a protein and a chimeric protein as described herein), a polynucleotide, a vector or a host cell as described herein. Preferably, an effective amount of a protein (including a protein consisting of amino acid sequence SEQ ID NO: 1, a protein and a chimeric protein) as described herein.

In preferred embodiments, said infection is caused by enteric Gram-negative bacteria, preferably selected from the group consisting of bacteria of the genus *Acinetobacter, Bacteroides, Campylobacter, Fusobacterium, Haemophilus, Helicobacter, Mobiluncus, Porphyromonas, Prevotella, Pseudomonas* and *Veillonella*, and the Enterobacteriaceae family (also referred herein as Enterobacteria). Some illustrative but not limiting examples of Enterobacteria include bacteria of the genus *Citrobacter, Enterobacter, Escherichia, Klebsiella, Proteus, Salmonella, Serratia, Shigella* and *Yersinia.*

In particular embodiments, said Gram-negative bacteria is selected from the group consisting of the genus *Acinetobacter, Pseudomonas, Escherichia, Klebsiella, Serratia* and *Citrobacter*, preferably from the group consisting of *Acine-*

*tobacter, Pseudomonas, Escherichia* and *Klebsiella*. In preferred embodiments, said Gram-negative bacteria is selected from the group consisting of *E. coli, K. pneumoniae, A. baumannii, P. aeruginosa, S. marcescens* and *C. freundii*, preferably from the group consisting of *E. coli, K. pneumoniae, A. baumannii* and *P. aeruginosa*. In certain embodiments, said Gram-negative bacteria is a drug resistant strain, including multi-drug resistant (MDR) strains.

In a 2019 European surveillance by EARS-Net, the most commonly reported bacterial species was *E. coli* (44.2%), followed by *Staphylococcus aureus* (20.6%), *Klebsiella pneumoniae* (11.3%), *E. faecalis* (6.8%), *P. aeruginosa* (5.6%), *S. pneumoniae* (5.3%), *E. faecium* (4.5%) and *Acinetobacter* species (1.7%) (European Centre for Disease Prevention and Control. Antimicrobial resistance in the EU/EEA (EARS-Net)-Annual Epidemiological Report 2019. Stockholm: ECDC; 2020). In this surveillance work it was observed that in 2019, more than half of the *E. coli* isolates reported and more than a third of the *K. pneumoniae* isolates were resistant to at least, one antimicrobial group under surveillance, and combined resistance to several antimicrobial groups was frequent. In the case of *P. aeruginosa* and *Acinetobacter* species, carbapenem resistance was common and at higher percentages than in *K. pneumoniae*.

In some embodiments, said Gram-negative bacteria is of the Enterobacteriaceae family. In preferred embodiments, said infection is caused by *Escherichia. coli*. The *E. coli* strain is not particularly limited to any serotype and illustrative examples include *E. coli* bacteria from serotypes O1 (e.g., O1A), O2, O6, (e.g., O6A), O25 (e.g. O25B) or O157 serotypes, which are serotypes frequently involved in urinary tract infections (Huttner and Gambillara 2018). In preferred embodiments, these belong to serotype O6 strains, such as *E. coli* ATCC 25922, or serotype O157 strains, such as *E. coli* O157: H7. In certain embodiments, said *E. coli* strain is a drug resistant strain, including multi-drug resistant (MDR) strains.

These MDR strains can be resistant to one, two, three, four, five, six, seven or more antibiotics, such as for example sulphonamides (e.g., sulfamethoxaxole and trimethoprim-sulfamethoxaxole), penicillins (e.g. ticarcillin, ticarcillin-clavulanate, piperacillin, piperacillin-tazobactam, amoxicillin, amoxicillin-clavulanate), cephalosporins (e.g., ceftazidime, cefepime, cefoperazone), monobactams (e.g., aztreonam), lincosamides (e.g., lincomycin), fluoroquinolones (e.g., ciprofloxacin, levofloxacin, norfloxacin), carbapenems (e.g., imipenem, meropenem, ertapenem, doripenem), aminoglycosides (e.g., gentamicin, tobramycin, amikacin), and polymixins (e.g., colistin, polymyxin B). For instance, said MDR strain is resistant to one or more, including all, of the antibiotics selected from the list consisting of sulphonamides, penicillins, lincosamides, fluoroquinolones, aminoglycosides and tetracyclines, preferably said MDR strain is resistant to one or more, including all, of the antibiotics selected from the list consisting of sulfonamide, amoxicillin, lincomycin, linco-spectin® (lincomycin+spectinomycin), enrofloxacin, neomycin and doxycycline (see MDR *E. coli* strains in Table 1 and Example 4).

In a particular embodiment, said Gram-negative bacteria is *Escherichia coli* and is resistant to one or more of sulfamide, amoxicillin, lincomycin, lincospectin, enrofloxacin, neomycin, and doxycycline. In another embodiment, said Gram-negative bacteria is *Klebsiella pneumoniae* and is resistant to one or more of beta lactams (e.g., carbapenems), fluoroquinolones and trimethoprim/sulfamethoxazole.

In a further embodiment, said Gram-negative bacteria is *Acinetobacter baumannii* and is resistant to one or more of aminoglycosides and trimethoprim/sulfamethoxazole.

In still a further embodiment, said Gram-negative bacteria is *Pseudomonas aeruginosa* and is resistant to beta lactams.

The infection caused by Gram-negative bacteria may occur in any organ or tissue of the subject. In a particular embodiment, the infection caused by Gram-negative bacteria occurs in blood, gastrointestinal tract, heart, cardiovascular system, liver, lung, respiratory tract, kidney, urinary tract, nervous central system, skin, subcutaneous tissues or surgical wounds. In a preferred embodiment, the infection caused by Gram-negative bacteria, for instance by one or more of the genus or species described herein above, preferably *E. coli* strains, occurs in the urinary tract. In another preferred embodiment, said infection occurs in blood.

The Gram-negative bacteria causing the infection to be treated can be human or veterinary pathogenic bacteria or strains. In some embodiments, Gram-negative bacteria are human pathogenic bacteria or strains. In other embodiments, Gram-negative bacteria are veterinary pathogenic bacteria or strains, such as avian or non-human mammals pathogenic bacteria or strains.

A composition that includes a protein (including a protein consisting of amino acid sequence SEQ ID NO:1, a protein and a chimeric protein as described herein), a polynucleotide, a vector or a host cell as described herein, preferably a protein (including a protein consisting of amino acid sequence SEQ ID NO:1, a protein and a chimeric protein as described herein) can be delivered to a subject by a variety of routes including, without limitation, by local (e.g. topical, rectal, ocular, etc.) or systemic administration. Systemic delivery, may include oral or parental (e.g., intravenous, subcutaneous, intramuscular and intraperitoneal) administration. Additionally, it is also possible to administer the composition comprising the agent of the invention intranasally or sublingually which allows systemic administration by a non-aggressive mode of administration. Also, intraventricular administration may be adequate. A preferred route of delivery is intravascular (e.g. intraarterial or intravenous) or subcutaneous injection. In a particular embodiment, the agent for use according to the invention is administered to the subject subcutaneously or intravenously. Those skilled in the art are familiar with the principles and procedures discussed in widely known and available sources as Remington's Pharmaceutical Science (17th Ed., Mack Publishing Co., Easton, Pa., 1985) and Goodman and Gilman's The Pharmaceutical Basis of Therapeutics (8th Ed., Pergamon Press, Elmsford, N.Y., 1990) both of which are incorporated herein by reference.

The agents of the invention can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, thriethylamine, 2-ethylamino ethanol, histidine, procaine or similar.

Solid dosage forms for oral administration may include conventional capsules, sustained release capsules, conventional tablets, sustained-release tablets, chewable tablets, sublingual tablets, effervescent tablets, pills, suspensions, powders, granules and gels. Formulations can include standard carriers such as pharmaceutical grades of mannitol, lactose, starch, magnesium stearate, sodium saccharide, cellulose, magnesium carbonate, etc. Such dosage forms can also comprise, as in normal practice, additional substances other than inert diluents, such as dispersing and/or granulating agents, surface active agents and/or emulsifiers, disintegrating agents, binding agents, preservatives, buffering agents, lubricating agents, and/or oils. In the case of capsules, tablets, effervescent tablets and pills, the dosage forms may also comprise buffering agents. Tablets and pills can be prepared with enteric coatings.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters {e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Various delivery systems are known in the art, including encapsulation in liposomes, microbubbles, emulsions, microparticles, microcapsules and the like.

Injectable preparations, for example, aqueous or oleaginous suspensions, may be formulated according with the known technique using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

Typically, compositions for intravenous, intramuscular, subcutaneous, intraperitoneal or intraventricular administration are solutions in sterile isotonic aqueous buffer. In some embodiments, the composition can contain minor amounts of wetting or emulsifying agents, or pH buffering agents. Illustrative non-limiting examples of pH buffering agents include Tris-HCl buffer, acetate buffer, citrate and phosphate buffer or combinations thereof. The term "acetate buffer", "citrate buffer" and "phosphate buffer" as used herein can refer to a buffer system comprising an organic acid (acetic acid, citric acid and phosphoric acid, respectively) and a salt thereof. Each of them can be added in a sufficient amount. The pH of the composition according to the present invention may be in the range from about 4 to about 8, preferably from about 5 to about 7, including pH 5, pH 5.5, pH 6, pH 6.5 and pH 7.

Where necessary, the agent of the invention is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

The effective quantity of the agent of the invention can vary within a wide range and, in general, will vary depending on the particular circumstances of application, duration of the exposure and other considerations. In a particular embodiment, the dose ranges from 0.01 mg/kg to 20 mg/kg, preferably from 0.05 mg/kg to 10 mg/kg, such as from 0.1 mg/kg to 5 mg/kg, or from 1 mg/kg to 2 mg/kg.

In a eleventh aspect the present invention relates to a process of preparation of a pharmaceutical composition, said process comprising admixing one or more of a protein (including a protein consisting of amino acid sequence SEQ ID NO:1, a protein and a chimeric protein as described herein)), polynucleotide, vector or host cell according to the present invention with a pharmaceutically acceptable carrier, vehicle or excipient.

In an twelfth aspect, the present invention relates to a kit comprising a protein (including a protein consisting of amino acid sequence SEQ ID NO: 1, a protein and a chimeric protein as described herein), a polynucleotide, a vector, a host cell or the composition as defined herein, alone or in combination. Reagents, tools, and/or instructions for performing the methods described herein can be provided in a kit. For example, the kit can contain reagents, tools, and instructions for use in the prophylactic and/or therapeutic treatment of an infection caused by Gram-negative bacteria or for conducting an in vitro method of inhibiting the growth, or reducing the population, or killing of Gram-negative bacteria. For instance, said Gram-negative bacteria are of one or more of the genus or species described herein above.

In a thirteenth aspect the invention pertains to an in vitro method of inhibiting the growth, or reducing the population, or killing of Gram-negative bacteria, the method comprising contacting the bacteria with a protein (including a protein consisting of amino acid sequence SEQ ID NO:1, a protein and a chimeric protein as described herein), a polynucleotide, a vector, a host cell or a composition as described herein. Preferably, a protein (including a protein consisting of amino acid sequence SEQ ID NO:1, a protein and a chimeric protein) as described herein. For instance, said Gram-negative bacteria are of one or more of the genus or species described herein above. In preferred embodiments said Gram-negative bacteria are Enterobacteria as described herein above, preferably, said Gram-negative bacteria is *K. pneumoniae* or *E. coli*. In other preferred embodiments, said Gram-negative bacteria is one or more selected from the group consisting of the genus *Acinetobacter, Pseudomonas, Escherichia* and *Klebsiella*, preferably from the group consisting of *E. coli, K. pneumoniae, A. baumannii* and *P. aeruginosa*.

In a fourteenth aspect, the invention provides a protein (including a protein consisting of amino acid sequence SEQ ID NO:1, a protein and a chimeric protein), a polynucleotide, an expression vector or host cell as described herein, wherein the a protein (including a protein consisting of amino acid sequence SEQ ID NO:1, a protein and a chimeric protein as described herein) or the encoded polypeptide has the property of inhibiting the growth, reducing the population, or killing Gram-negative bacteria. For instance, said Gram-negative bacteria are of one or more of the genus or species described herein above. In preferred embodiments said Gram-negative bacteria are Enterobacteria as described herein above, preferably *K. pneumoniae* or *E. coli*. In other preferred embodiments, said Gram-negative bacteria is one or more selected from the group consisting of the genus *Acinetobacter, Pseudomonas, Escherichia* and *Klebsiella,* preferably from the group consisting of *E. coli, K. pneumoniae, A. baumannii* and *P. aeruginosa.*

The agents of the present invention (e.g., a protein (including a protein consisting of amino acid sequence SEQ ID NO:1, a protein and a chimeric protein as described herein), polynucleotide, expression vector or host cell) can be used alone or in combination with permeabilizing agents of the outer membrane of the Gram-negative bacteria, including, but not limited to metal chelators as e.g. EDTA, TRIS, lactic acid, lactoferrin, polymyxins, citric acid (Vaara M. 1992). This may be part of the same or separate compositions. In preferred embodiments, the agents of the present invention are not used in combination with permeabilizing agents.

The protein (including a protein consisting of amino acid sequence SEQ ID NO:1, a protein and a chimeric protein as described herein), polynucleotide, vector, host cell or pharmaceutical composition for use in a method of treatment as described herein can be used alone (i.e., as a single agent) or in combination with one or more therapeutic agents, including antiseptic reagents, lantibiotics, bacteriocins, other endolysins or antibiotics.

Antiseptic reagents include, but are not limited to Daquin's solution, sodium or potassium hypochlorite solution, solution of sodium benzenesulfochloramide, certain iodine preparations, such as iodopovidone, peroxides as urea perhydrate solutions and pH-buffered peracetic acid solutions, alcohols with or without antiseptic additives, weak organic acids such as sorbic acid, benzoic acid, lactic acid and salicylic acid, some phenolic compounds, such as hexachlorophene, triclosan and Dibromol, and cation-active compounds, such as benzalkonium, Chlorhexidine, methylisothiazolone, a-terpineol, thymol, chloroxylenol octenidine solutions.

In a fifteenth aspect, the invention also relates to an agent of the invention (e.g., a protein (including a protein consisting of amino acid sequence SEQ ID NO:1, a protein and a chimeric protein as described herein), polynucleotide, expression vector or host cell) as described herein, or the pharmaceutical composition comprising the same, for use in a method of treating and/or preventing Gram-negative bacterial infections as described herein, wherein said treatment comprises the administration of an agent of the invention as described herein in combination with another drug. Each agent may be administered at a dose and/or on a time schedule generally used for that agent as single agent or in combination therapies. Dosage and administration regimens for the chimeric protein of the invention have been described herein.

In a particular embodiment, administration of an agent of the invention as described herein is simultaneous to the administration of said other drug, as part of the same or separate compositions. In another particular embodiment, administration of an agent of the invention as described herein is sequential (prior to or subsequent) to the administration of said other drug.

In preferred embodiments, said other drug is an antibiotic. Traditional antibiotics used against Gram-negative bacteria which may be used in the present invention include, but are not limited to, sulphonamides (e.g., sulfamethoxazole and trimethoprim-sulfamethoxazole), penicillins (e.g., ticarcillin, piperacillin, amoxicillin, including ureidopenicillins [e.g. azlocillin, piperacillin, mezlocillin]), cefalosporines (e.g., ceftazidime, cefepime, cefoperazone)), monobactams (e.g., aztreonam), lincosamides (e.g., lincomycin), fluoroquinolones (e.g., ciprofloxacin, levofloxacin, norfloxacin), carbapenems (e.g., imipenem, meropenem, ertapenem, doripenem), aminoglycosides (e.g., genatmicin, tobramycin, amikacin), and polymixins (e.g., colistin, polymyxin B) . . .

The invention is also directed to the use of an agent of the invention as described herein for the manufacture of a medicament for the treatment and/or prevention of Gram-negative bacterial infections as described herein by a combination therapy employing an agent of the invention as described herein with another drug, preferably an antibiotic, as described herein.

It is further directed to a method of treating and/or preventing Gram-negative bacterial infections as described herein, comprising administering to a patient in need of such treatment a therapeutically effective amount of an agent of the invention as described herein, in combination with a therapeutically effective amount of another drug, preferably an antibiotic, as described herein.

In preferred embodiments, said combination is a synergistic combination. As described in Example 10 synergism has been found between the protein (including a protein consisting of amino acid sequence SEQ ID NO:1, a protein and a chimeric protein as described herein) of the invention and antibiotics of the carbapenem group, preferably selected from the group consisting of imipenem and meropenem. Thus, in particularly preferred embodiments, the chimeric protein of the invention is used as a combination therapy with a carbapenem antibiotic.

In a further aspect, the present invention also relates to the use of a protein (including a protein consisting of amino acid sequence SEQ ID NO: 1, a protein and a chimeric protein as described herein) as described herein or a composition comprising thereof as disinfectant for materials and/or surfaces, in hospitals as well as in private households. These materials and/or surfaces include but are not limited to medical devices such as joint replacements and other types of orthopaedic instrumentation, prosthetic heart valves, pacemakers, implantable defibrillators, urinary catheters and stents, peritoneal dialysis catheters, intravascular catheters, cerebrospinal fluid shunts, breast implants, and vascular grafts and stents. Said composition may comprise the protein (including a protein consisting of amino acid sequence SEQ ID NO:1, a protein and a chimeric protein as described herein) of the invention, and optionally further comprise other disinfectants and/or surfactants.

It is contemplated that any features described herein can optionally be combined with any of the embodiments of the protein (including a protein consisting of amino acid sequence SEQ ID NO: 1, a protein and a chimeric protein as described herein), polynucleotide, vector, host cell, composition, kit, any use, medical use, method of treatment, method of manufacturing a medicament and combination therapies of the invention; and any embodiment discussed in this specification can be implemented with respect to any of these. It will be understood that particular embodiments described herein are shown by way of illustration and not as limitations of the invention.

All publications and patent applications are herein incorporated by reference to the same extent as if each individual publication or patent application was specifically and individually indicated to be incorporated by reference.

The use of the word "a" or "an" may mean "one," but it is also consistent with the meaning of "one or more," "at least one," and "one or more than one". The use of the term "another" may also refer to one or more. The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "comprises" also encompasses and expressly discloses the terms "consists of" and "consists essentially of". As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "around", "approximately" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by ±1, 2, 3, 4, 5, 6, 7, 8, 9, or 10%. Accordingly, the term "about" may mean the indicated value ±5% of its value, preferably the indicated value ±2% of its value, most preferably the term "about" means exactly the indicated value (±0%). The following examples serve to illustrate the present invention and should not be construed as limiting the scope thereof.

Examples

The assays disclosed in the Examples below were carried out using the following materials and methodologies.
Bacterial Strains and Culture Media
The bacterial strains and culture media used are described in detail in Table 1.

All the solutions and culture media used were sterilized by means of moist heat in an autoclave at 120° C. and a pressure of 1 atmosphere, or by means of filtration using sterile Millipore filters 0.2 μm in diameter.

Antibiotics were prepared in concentrated solutions in water. These solutions were sterilized by means of filtration and stored at –20° C.

TABLE 1

| Bacteria and culture media | | | |
|---|---|---|---|
| Bacterium (serotype) | Reference | Temperature (° C.) | Culture media |
| *Escherichia coli* (O6) | ATCC 25922 | 37 | Luria-Bertani (LB) broth |
| *Escherichia coli* (O157:H7) | DSM 17076 | 37 | Luria-Bertani (LB) broth |
| *Escherichia coli* MDR | 93658[a] | 37 | Luria-Bertani (LB) broth |
| *Escherichia coli* MDR | 93729[a] | 37 | Luria-Bertani (LB) broth |
| *Escherichia coli* MDR | 93449[a] | 37 | Luria-Bertani (LB) broth |
| *Escherichia coli* MDR | 94657[a] | 37 | Luria-Bertani (LB) broth |
| *Staphylococcus xylosus* | ATCC 29971 | 37 | Trypticase soy yeast extract medium (TSY) |
| *Enterococcus faecium* | ATCC 19434 | 37 | Trypticase soy yeast extract medium (TSY) |
| *Enterococcus faecalis* | ATCC 19433 | 37 | Trypticase soy yeast extract medium (TSY) |
| *Enterococcus avium* | ATCC 14025 | 37 | Trypticase soy yeast extract medium (TSY) |
| *Citrobacter freundii* | ATCC 30039 | 30 | Trypticase soy yeast extract medium (TSY) |
| *Enterobacter cloacae* | ATCC 13047 | 30 | Tryptic soy broth (TSB) |
| *Serratia marcescens* | ATCC 13880 | 30 | Tryptic soy broth (TSB) |
| *Klebsiella pneumoniae* | ATCC 13883 | 37 | Trypticase soy yeast extract medium (TSY) |
| *Klebsiella pneumoniae* | ATCC 700603[b] | 37 | Trypticase soy yeast extract medium (TSY) |
| *Klebsiella pneumoniae* | ATCC BAA-1705[c] | 37 | Trypticase soy yeast extract medium (TSY) |
| *Klebsiella pneumoniae* | ATCC BAA-1706[d] | 37 | Trypticase soy yeast extract medium (TSY) |
| *Acinetobacter baumannii* | ATCC 19606 | 30 | Trypticase soy yeast extract medium (TSY) |
| *Acinetobacter baumannii* | NCTC 13304[e] | 30 | Trypticase soy yeast extract medium (TSY) |

TABLE 1-continued

| Bacteria and culture media | | | |
| --- | --- | --- | --- |
| Bacterium (serotype) | Reference | Temperature (° C.) | Culture media |
| Pseudomonas aeruginosa | ATCC 10145 | 37 | Trypticase soy yeast extract medium (TSY) |
| Pseudomonas aeruginosa | ATCC 27853[f] | 37 | Trypticase soy yeast extract medium (TSY) |

[a]multidrug resistant isolate obtained from sick chicken in a poultry farm. 93568 is resistant to sulfamide, amoxicillin, lincomycin, lincospectin, enrofloxacin, neomycin, and doxycycline; 93729 is resistant to sulfamide, amoxicillin, lincomycin, enrofloxacin, neomycin, and doxycycline; 93449 is resistant to amoxicillin, lincomycin, lincospectin, enrofloxacin, neomycin, and doxycycline; 94657 is resistant to sulfamide, amoxicillin, lincomycin, lincospectin, neomycin, and doxycycline.
[b]resistant to beta lactams.
[c]resistant to beta lactams, fluoroquinolones and trimethoprim/sulfamethoxazole.
[d]resistant to carbapenems.
[e]resistant to aminoglycosides and trimethoprim/sulfamethoxazole.
[f]resistant to beta lactams.

Construction, Expression, and Purification of IKB206 and IKB206 Variant

IKB206 is the result of the fusion of *Enterobacter* phage Arya (NCBI accession number NC_031048.1) putative endolysin (SEQ ID NO:1) (Protein ID: YP_009284326.1) and the putative cell wall binding domain (D8) of *Bacillus amyloliquefaciens* (Morita 2001) (accession number AAK40280.1) phage endolysin (SEQ ID NO:2). Two IKB206 constructions were designed and cloned into expression plasmid pET29b (+) using GenScript®. In the first, the DNA fragment encoding the IKB206 chimera was cloned into the plasmid in such a way that the sequences encoding two tags (S-tag and His-tag) were removed from the plasmid. In the second, the sequences corresponding to the tags were not be removed and a cleavage site for thrombin and 3 amino acids were added to the resulting fusion to improve thrombin cleavage efficiency. For illustrative non-limiting purposes, schematic representations of the chimeric lysins are provided in FIG. 1.

In addition, the putative endolysin from phage Arya alone was cloned into the plasmid pET29b (+) following the same strategy as for IKB206 without tags. This construction was named IKB206ΔD8.

IKB206These three recombinant plasmids were transformed into competent *Escherichia coli* BL21 (DE3) (Invitrogen, Carlsbad, CA, USA).

For the overexpression with tags (IKB206$_{tags}$), the transformed BL21 (DE3) cells were cultured at 37° C. in LB medium supplemented with 30 μg mL$^{-1}$ of kanamycin sulfate. When the culture reached an absorbance at 600 nm (A$_{600}$) of 1.5, 1 mM of isopropyl-β-d-thiogalactopyranoside (IPTG) were added and it was incubated for 4-5 hours at 37° C. The cells were collected by means of centrifugation (10000×g, 30 min), resuspended in 20 mM Na$_2$HPO$_4$/NaH$_2$PO$_4$, 0.5 M NaCl, 20 mM imidazole, pH 7, and ruptured using the Branson Sonifier SFX150 (Branson Sonic Power, Danbury). The soluble protein fraction (supernatant) was separated by centrifugation (15000×g, 30 min) and filtered (0.45 μm) before purification. IKB206$_{tags}$ was purified using 5 mL HisTrap FF columns pre-packed with Ni Sepharose preloaded in the ÄKTAStar chromatography system (GE Healthcare, USA). IKB206$_{tags}$ was eluted with 20 mM Na$_2$HPO$_4$/NaH$_2$PO$_4$, 0.25 M NaCl, 0.4 M imidazole, pH 8. Subsequently, IKB206$_{tags}$ was desalinized using 5 mL HiTrap™ Desalting in the ÄKTAStar chromatography system (GE Healthcare, USA) and 20 mM Na$_2$HPO$_4$/NaH$_2$PO$_4$, PH 6. IKB206$_{tags}$ was stored at −20° C.

For the overexpression of IKB206 without tags, the transformed BL21 (DE3) cells were cultured at 37° C. in autoinducible LB broth medium (Studier FW, 2005) supplemented with μg mL$^{-1}$ of kanamycin sulfate. After 3 h at 37° C., temperature was changed to 25° C. and cells were cultured 4 h before harvesting. Cells were collected by means of centrifugation (10000×g, 30 min), resuspended into a lysis buffer containing 50 mM Tris pH 9, protease inhibitors (Thermo Fisher Scientific Massachusetts USA) and DNAse I (Roche), and lysed by sonication in a Branson Sonifier SFX150 (Branson Sonic Power, Danbury). The soluble protein fraction (supernatant) was separated by centrifugation (23666×g, 1 h 30 min) and filtered (0.22 μm) before purification. Protein solution was subjected to cation exchange chromatography using a 5 mL HiTrap SP HP columns connected to an ÄKTA go chromatography system (Cytiva life sciences, USA). IKB206 was eluted over a gradient with 50 mM Tris, 1M NaCl, pH 9. Protein presence was confirmed by SDS-PAGE, and fractions containing the protein were pooled and concentrated until a final volume of 2-5 ml approximately. Solution was 0.22 μm filtered and loaded into a HiLoad 16/600 Superdex 75 size exclusion column, preequilibrated with 20 mM Tris, 500 mM NaCl, pH 8. Protein presence was confirmed by SDS-PAGE. Subsequently, IKB206 was desalinized using a 5 mL HiTrap Desalting column connected to the ÄKTA go chromatography system (Cytiva, USA) and 10 mM Na$_2$HPO$_4$/NaH$_2$PO$_4$, PH 6. IKB206 was stored at −80° C.

For the overexpression of IKB206AD8, the transformed BL21 (DE3) cells were cultured at 37° C. in LB broth medium supplemented with 30 μg mL$^{-1}$ of kanamycin sulfate. When the culture reached an absorbance at 600 nm (A$_{600}$) of 0.8, 1 mM of isopropyl-β-d-thiogalactopyranoside (IPTG) was added and cells were incubated overnight at 25° C. before harvesting. The cells were collected by means of centrifugation (10000×g, 30 min), resuspended into a lysis buffer containing 50 mM Tris pH 8.5, protease inhibitors (Thermo Fisher Scientific Massachusetts USA) and DNAse I (Roche), and lysed by sonication in a Branson Sonifier SFX150 (Branson Sonic Power, Danbury). The soluble protein fraction (supernatant) was separated by centrifugation (23666×g, 1 h 30 min) and filtered (0.22 μm) before purification. Protein solution was subjected to cation exchange chromatography using 5 mL HiTrap SP HP columns connected to an ÄKTA go chromatography system (Cytiva life sciences, USA). The endolysin was eluted over a gradient with 50 mM Tris, 1 M NaCl, pH 8,5. Protein presence was confirmed by SDS-PAGE, and fractions containing the protein were pooled and 0.22 μm filtered. The protein was desalinized using a 5 mL HiTrap desalting column connected to the ÄKTA go chromatography system (Cytiva, USA) and 10 mM $Na_2HPO_4/NaH_2PO_4$, PH 6. IKB206AD8 was stored at $-80°$ C.

The quantification of purified proteins was performed by the Bradford method using Coomasie blue (Thermo Fisher Scientific) and the $A_{595}$ in a Spectrostar Nano spectrophotometer (BMG labtech). The purity of the isolated protein was verified by SDS-PAGE. SDS-PAGE analysis was carried out with 4-12% SurePage™ gels (GenScript, Nanjing) at a constant voltage (200 V) in Tris-MOPS-SDS electrophoresis buffer (GenScript, Nanjing).

Enzyme Bactericidal Activity Assays

The experiments carried out for analyzing the bactericidal activity of the enzyme IKB206 (without tags, with tags or without D8 domain) were performed using a modified version of a protocol previously described by Loessner et al. (Loessner, M. J. et al. 2002) and Schmelcher et al. (Schmelcher, M. et al. 2010). Briefly, the different bacterial cultures were incubated in the specific media (Table 1) at 37° C. or 30° C., according to the strain, until reaching an $A_{600}$ of 0.3. The cells were then deposited by centrifugation (4500×g, 10 min) and washed twice with the corresponding buffer, with the $A_{600}$ being adjusted to ≈0.3. A volume of 160 μl of the bacterial suspension was transferred to sterile 96-well plates to which there were added 40 μl of the enzyme under study in a range of doses comprised between 1 and 60 μg $mL^{-1}$. The control wells were treated with the same volume of buffer containing the enzyme. The plates were incubated at 37° C. Samples were taken at different times, serial dilutions performed, and they were seeded in plates containing the specific medium to determine viable bacteria. The experiments were repeated at least 3 times. The bactericidal effect of IKB206 (and its variants) was quantified as the number of logs reduced in the presence of treatment, after a given incubation time ($log_{10}$ ($N_0/N_i$), where $N_0$=number of CFU $mL^{-1}$ before treatment, and $N_i$=number of CFU $mL^{-1}$ after the corresponding incubation time in the presence of each treatment). A compound is considered to have bactericidal activity when after incubation with said compound the number of initial bacteria is reduced ≥99.9% (≥3-log reduction).

Enzyme Specific Activity Assays

The specific activity (U mG-1) was determined using a suspension of 0.6 mg $mL^{-1}$ of *M. lysodeikticus* lyophilized cells as substrate resuspended in cold buffer of the enzyme (10 mM $Na_2HPO_4/NaH_2PO_4$, PH 6 for IKB206$_{tags}$ and 50 mM $K_2HPO_4/KH_2PO_4$, pH 6.2 for egg white lysozyme) and incubating this suspension at different concentrations of the enzyme. Egg white lysozyme (Fisher BioReagents™ Lysozyme) was used as a control. Specifically, 100 μL of the M. lysodeikticus suspension were plated, in triplicate, into a multi-well plate and 100 μL of the different enzyme concentrations were added to the corresponding well. The plate was incubated at the appropriate temperature into a thermostated spectrophotometer (37° C. for IKB206$_{tags}$ and 25° C. for egg white lysozyme) and the $A_{450}$ decrease was monitored over 10 min.

Unit definition: 1 unit is that amount of enzyme needed to catalyze a decrease in absorbance at 450 nm of 0.001/min at the appropriate temperature and pH of each lysozyme in a 1 cm cuvette due to lysis using a ~0.4-0.6 mg/mL suspension of M. lysodeikticus.

Physicochemical Characterization Assays

The experiments for studying conditions that are optimal for the enzymatic activity of IKB206$_{tags}$ were performed by means of *E. coli* bactericidal activity assay. To that end, *E. coli* strain ATCC 25922 and protein concentrations between 1 and 60 μg $mL^{-1}$ were used. The assays were performed in a range of pH between 6 and 8 and a range of sodium phosphate buffer ($Na_2HPO_4/NaH_2PO_4$) concentrations between 10 and 50 mM.

Stability Studies

The experiments for determining the stability of IKB206 were performed by means of *E. coli* bactericidal activity assay at 60 min of incubation time. To that end, *E. coli* strain ATCC 25922 and 15 μg $mL^{-1}$ of IKB206 dissolved in different concentrations of glycerol (0, 0.2, 2, 5 and 10%) were used. The assays were carried out at different storage temperatures ($-80°$ C., $-20°$ C., 4° C., 25° C.) and storage times (1, 5, 7, 14, 21 and 29 days).

Cytotoxicity Assays by Means of Sulforhodamine B

A seeding test was performed with human HEK293 cells before performing the experiment. To that end, three different cell concentrations were seeded in a 96-well plate in 100 μl of DMEM medium+10% Fetal Bovine Serum (FBS). These cells were incubated at 37° C. and 5% $CO_2$ for 72 h, monitoring growth. The initial cell concentration showing 80% confluence at 72 h was selected for the further assays, which in this case was 7000 cells/well. Twenty-four hours after seeding the cells, another 100 μl of medium with the concentrations of purified protein IKB206$_{tags}$ to be tested was added. In this case, 400 μg $mL^{-1}$, 200 μg $mL^{-1}$, 100 μg $mL^{-1}$, and 50 μg $mL^{-1}$. The assays were performed in quadruplicate. As controls, the cells were incubated only with culture media and with the buffer in which the protein is dissolved (vehicle control). Buffer volume added as a vehicle control was the same volume of the highest protein concentration. The plate was left to incubate for another 48 h. The results were obtained by means of fixing the cells by adding 50 μl of 50% cold trichloroacetic acid (TCA) per well and leaving the plate to incubate for 1 h at room temperature. After discarding the TCA, the plate was washed with distilled water and 40 μl of 0.4% sulforhodamine B (SRB) were added. The plate was incubated for 15 minutes at room temperature, three washes were performed with 1% of acetic acid, and the plate was left to dry. Finally, 200 μl of 10 mM Tris Base were added per well and it was incubated for 20 min under stirring at room temperature to resuspend the SRB. The results were read in Cytation (Bioteck, USA) at an absorbance of 510 nm.

Efficacy Assay Using a Sepsis Model in Zebrafish

Experiments with adult zebrafish were performed at the Ikan Biotech facilities in Noáin (Navarre). All the scientific methods for said assays were performed according to Royal Decree 53/2013 of 8 Feb. 2013 and according to the laws of National Institutes of Health Guide for the Care and Use of Laboratory approved by the Institutional Committee for the Care and Use of Animal of the University of Navarre (Pamplona, Spain). The Committee belonging to said institution approved all the experiments performed with animals in this study (protocol 034-17 and revision e035-17).

To calculate the minimum lethal dose which caused 100% mortality in a period of 7 days, groups of five (5) six-month old wild-type female zebrafish were inoculated intraperitoneally (IP) with different bacterial dilutions of *E. coli* strain in LB medium.

Once the minimum lethal dose is determined, the six-month old wild-type zebrafish (1.2 grams) were inoculated intraperitoneally (IP) with a total of 10 μl containing $5.5×10^7$ CFU $mL^{-1}$ of the bacterium *E. coli* grown in LB medium. All the experiments were repeated at least three times.

To study the protection mediated by the chimera IKB206$_{tags}$, groups of five (5) six-month old wild-type female zebrafish were infected intraperitoneally (IP) with a lethal dose of the bacterium *E. coli* ($5.5×10^7$ CFU). After 1 h, the animals were treated by administering 10 µl of IKB206$_{tags}$ subcutaneously with a dose of 1, 0.5, and 0.25 mg kg-1 of body weight. The fish included in the control group were treated with the buffer in which the protein is dissolved. The animals were observed several times a day and the number of deaths was recorded daily 72 hours post infection (hpi).

Bacterial Strains, Antibiotics & Endolysin Used in the Synergism Studies

The *E. coli* strain used in this work and their MICs are shown in Table 2. The IKB206$_{tags}$ endolysin was purified from the *Escherichia coli* BL21 (DE3) strain, as previously described.

TABLE 2

| MICs (mg L$^{-1}$) of each of the antibiotics and IKB206$_{tags}$ in TP-Na 10 mM pH 6.15 | |
| --- | --- |
| Antibiotic | *E. coli* ATCC 25922 |
| Meropenem (Sigma-Aldrich) | 0.59 |
| Imepenem (Sigma-Aldrich) | 2.34 |
| IKB206 | 9.375 |

Checkerboard & Isobologram Analysis

Checkerboard tests were assessed by the microdilution method, as previously described (Moody JA 1992, Moellering E G., Jr.1996). All compounds were tested at six concentrations, at two-fold serial dilutions, which usually ranged from 0.03× to 2×MIC. Each microtiter well contained 100 µl of a *E. coli* inoculum of 1×10$^5$ CFUs mL$^{-1}$, with or without the corresponding compounds, in a final volume of 200 µl of Sodium phosphate (TP-Na) buffer 10 mM pH 6.15 per well and the plates were incubated at 37° C. for 17 h.

The fractional inhibitory concentration index (FICI) was calculated as the MIC of IKB206$_{tags}$ or each antibiotic in the combination, divided by the MIC of the IKB206 or each antibiotic alone (Moody J A 1992, Moellering E G., Jr.1996). The FICI was obtained by the sum of FICIs, as follows:

FICI$_x$=FICI$_A$+FICI$_B$=MIC$_A$ in combination/MIC$_A$+MIC$_B$ in combination/MIC$_B$ The MIC of drug A is marked on the x-axis of an isobologram and the MIC of drug B on the y-axis. The line connecting these two data is the indifference line (no interaction). The different FICI values of the combination indicate synergistic (FICI≤0.5), partial synergism (0.5<FICI<1), additive (FICI=1), indifferent (1<FICI<2), or antagonistic (FICI>2) interactions.

In Vitro Time-Killing Curve Tests of Single Drugs & Combinations

Time-killing assays were assessed according to the Clinical & Laboratory Standards Institute (CLSI) guidelines (National Committee for Clinical Laboratory Standard (NC-CLS) *Methods for determining bactericidal activity of antimicrobial agents*. Wayne, PA: CLSI; 1999. Document M26-A). The studied combinations in time-killing assays were carried out with each antibiotic and enzyme alone or in combination, at proven concentrations of synergistic effect. In these assays, 1×10$^6$ CFU/mL of the tested strains were incubated in TP-Na 10 mM pH 6.15 with the individual compounds or the combinations in separate tubes. At 17 h, aliquots were removed from each tube and diluted serially (1:10) using sterile saline to determine cell viability. From each dilution, 10 µl were added in LB Agar plates and were incubated at 37° C. for 24 h (detection limit, 10$^2$ CFU mL$^{-1}$). According to Clinical & Laboratory Standards Institute, a combination of two antimicrobial agents is considered synergistic when it causes a ≥2 log unit reduction in CFU mL$^{-1}$, compared with the sum of the reductions observed with the individual compounds at the end of the experiment, in this case at 17 h (CLSI guidelines).

Bioinformatics Analysis

Programs that can be accessed over the Internet, such as BLAST, GenomeNet, Expasy, and PFAM, were used for bioinformatics analysis.

Structural model of the catalytic cavity of IKB206 and the D8 domain were built using the online available softwares Phyre 2 (Kelley L A et al. 2015) and Swissmodel (Waterhouse, A et al. 2018). Sequence alignments were prepared using Clustal omega and Espript.

Structural analysis and figures were prepared using Pymol and Chimera softwares (Pettersen E F et al. 2004).

Statistical Analysis

The data shown throughout this study is representative of the results obtained from the repetition of 3 to 5 independent experiments, according to the type of assay. Furthermore, each datum shows the means and standard error. The programs GraphPad InStat version 3.0 (GraphPad Software, San Diego, CA) and the software Stata 15.0 (StataCorp LLC, Texas, TX) were used for statistical analysis.

Depending on the characteristics of the data (normality and homoscedasticity), Kruskal Wallis test was used together with the U-Mann Whitney test, analysis of variance (ANOVA) was used together with the Tukey test or t-test, for in vitro bactericidal activity assays.

Kruskal Wallis test was used for data relating to human cell toxicity.

In the survival experiments in which the protective effect of enzyme IKB206 in the different animal models was determined, an ANOVA was used together with a Dunnett's test as well as the ordinal log-rank (Mantel-Cox) test to verify the significant value of the surviving animals in the different experimental groups.

Example 1.—IKB206 and IKB206$_{tags}$ Expression and Purification

The chimera was cloned into pET-29b (+) plasmid in two different ways: With a S- and 6×His tag in the N and C terminal ends (IKB206$_{tags}$, FIG. 1*b*), and without any tag (IKB206, FIG. 1*a*). The first assays were carried out with IKB206$_{tags}$ to facilitate the purification process. After observing that the chimera showed bactericidal activity against *E. coli*, the following bactericidal assays were carried out with the chimera without tags, IKB206.

IKB206$_{tags}$ was overexpressed by the induction with 1 mM IPTG, of a culture with an A$_{600}$ of ≈1.5 for 4-5 hours at 37° C. and 200 rpm. This is because better results were obtained with said conditions in the purification step. Protein purification was performed by means of affinity chromatography using the 6×His tag. FIG. 2 shows the obtained protein purity of IKB206$_{tags}$. As can be seen in the figure, the estimated size in silico corresponds with the size obtained in electrophoresis (35.4 kDa).

IKB206 was overexpressed using an autoinducible LB broth (Studier FW. 2005) 4 h at 25° C. and 200 rpm. Protein purification was performed by means of cation exchange chromatography at pH 9 (IKB206 pl is ≈10) followed by size exclusion chromatography. FIG. 2*b* shows the obtained protein purity of IKB206. The molecular weight of the band corresponds with the in silico molecular weight of IKB206 which is 29.9 kDa.

Example 2.—Physicochemical Characterization

To determine the optimal conditions for IKB206$_{tags}$ in the in vitro assays for the purpose of obtaining its maximum activity, the effect of different sodium phosphate buffer concentrations and pH on the bactericidal activity of IKB206$_{tags}$ was investigated. To that end, *E. coli* ATCC 25922 resuspended in phosphate buffer at different concentrations and adjusted to the different pH was used as a substrate. The difference in CFU mL$^{-1}$ between the control and treatments with protein under different conditions was measured and it was found that the highest bactericidal activity was observed in the phosphate buffer with a concentration of 10 mM and pH 6 (data not shown).

Moreover, both the net charge of the protein and the net charge of the modules were estimated based on the respective sequences by means of the bioinformatics portal Expasy ProtParam. The net charge of the complete protein is +21, the net charge of the module corresponding to phage Arya endolysin is +7, and the net charge of module D8 is +15.

Example 3.—Stability Studies

To determine the optimal storage conditions for the chimera IKB206, bactericidal activity assays were performed with the chimera stored at different temperatures for different periods of time. Furthermore, it was studied whether glycerol helped to increase the stability of the protein in the different storage conditions studied. The chimeric protein was found to be still fully active at all temperatures and glycerol concentrations tested at 29 days of storage (data not shown).

Example 4.—Functional Characterization of IKB206$_{tags}$

Once the optimal conditions for IKB206$_{tags}$ activity have been determined, a functional characterization of the enzyme was then performed. For this purpose, the specific activity (U mg$^{-1}$) and the bactericidal activity of this enzyme was determined.

The standard test to determine the enzymatic activity of a lysozyme consists in measuring the reduction of the A$_{450}$ of a suspension of intact *M. lysodeikticus* cells after incubation with the enzyme. After performing two independent assays of this type and following the protocol described above, it was determined that the specific activity of IKB206$_{tags}$ is around 8100 U mg$^{-1}$.

Figure 3:
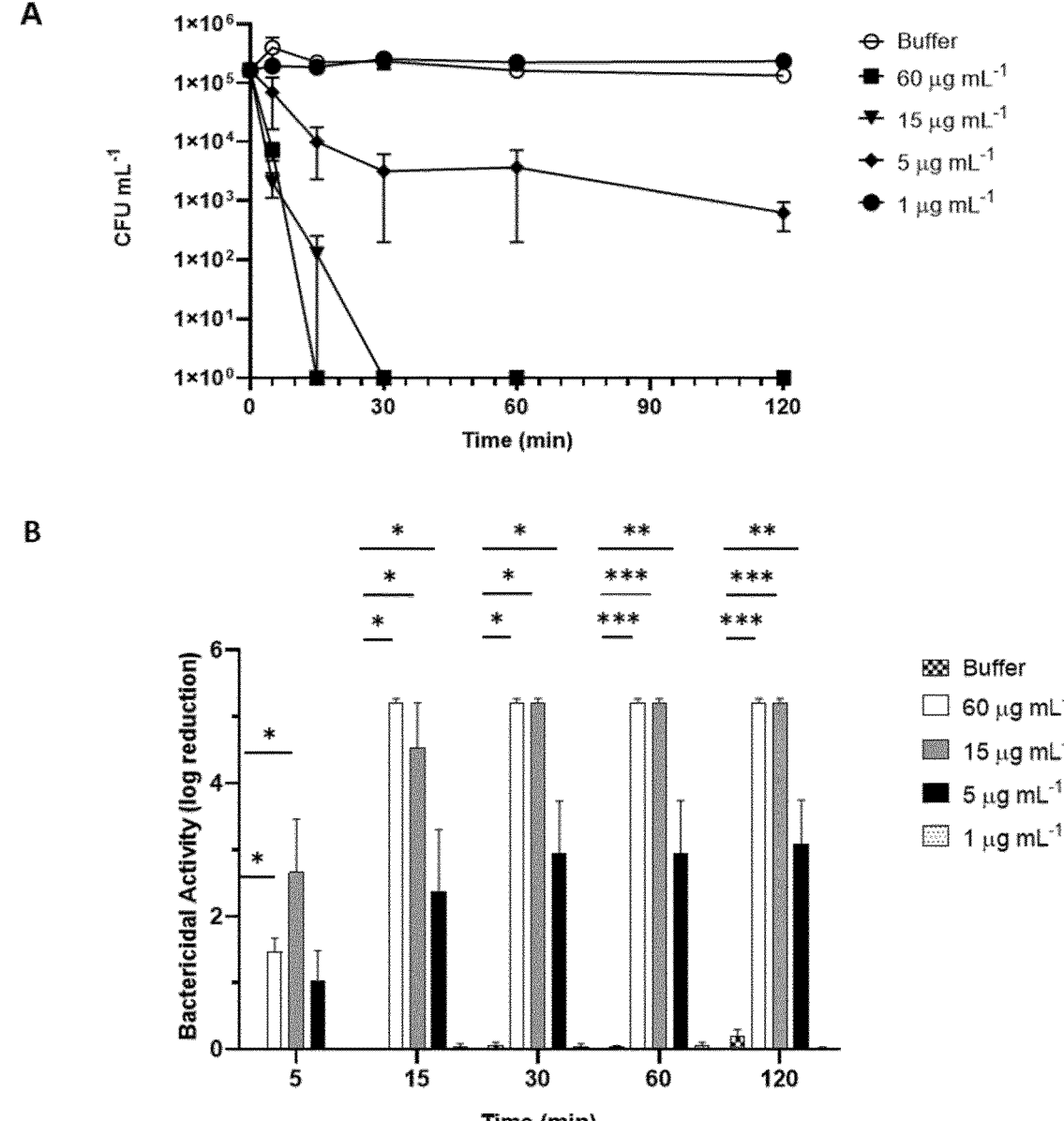
FIG. 3: Bactericidal effect of IKB206tags on *E. coli* strain ATCC 25922. *E. coli* cultures were resuspended in buffer, adjusting the bacterial suspension to $10^5$ colony forming units (CFU) mL$^{-1}$, and the cultures were incubated in the absence (buffer) or presence of the enzyme at 37° C. for 2 h. The data is representative of 4 independent experiments. Viable cells were determined by counting in LB agar plates. A) Bactericidal effect of expressed IKB206$_{tags}$ on the reduction of CFU mL$^{-1}$ over time in the presence of different enzyme concentrations. B) Bactericidal effect of expressed IKB206$_{tags}$ on the reduction of the number of logs over time in the presence of different enzyme concentrations. The error bars represent the standard error. The asterisks represent a significant difference (* P<0.05;  P<0.005; * P<0.0005) with respect to the control (buffer) according to: a one-way ANOVA test followed by a Tukey test in the case of samples showing a normal distribution and homoscedasticity; and a Kruskal Wallis test followed by the U-Mann Whitney test in the case of samples not showing a normal distribution or showing heterogeneity of variances.

After determining the specific activity, the bactericidal activity of this enzyme on *E. coli* ATCC 25922 at different concentrations was determined. Following the protocol described above, it was observed that IKB206$_{tags}$ was capable of significantly reducing (P<0.05) the number of CFU mL$^{-1}$ (more than 2 logs or 100 times) after only 5 minutes of incubation with respect to control and at a concentration of 15 μg mL$^{-1}$ (FIG. 3). Furthermore, if the incubation time was increased to 15 min, the reduction in CFU mL$^{-1}$ in the presence of IKB206$_{tags}$ Was significant (P<0.05) at a concentration of only 5 μg mL$^{-1}$. Assays of this type were performed starting from bacterial suspensions consisting of 105 CFU mL$^{-1}$ and it was observed that this enzyme was capable of killing the entire culture in an incubation time of 15 min at the concentration of 60 μg mL$^{-1}$ and in 30 minutes at the concentration of 15 μg mL$^{-1}$ (FIG. 3). In other words, IKB206 was capable of achieving a 5-log (100000-fold) reduction of the bacterial suspension within 30 minutes of incubation.

To determine if IKB206$_{tags}$ activity could be extended to serotypes other than that of *E. coli* strain ATCC 25922 (06 serotype), the study was expanded to cover *E. coli* strain DSM 17076 with serotype O157: H7. Based on the preceding results, 15 μg mL$^{-1}$ was chosen as the concentration suitable for these assays. FIG. 4 shows the obtained results. The recombinant lysin significantly reduced the number of *E. coli* strain DSM 17076 cells, although it was not capable of killing the entire culture.

Due to the clinical importance that *E. coli* multidrug resistant (MDR) *E. coli* strains have on human and veterinary health, a series of assays was performed to determine the bactericidal activity of IKB206$_{tags}$ on MDR strains isolated from chicken (see Table 1). In general, it was observed that IKB206$_{tags}$ was capable of achieving, in a significant manner, between 2- and 5-log (100- and 100000-fold) reductions in the number of bacteria present in the assays after 30 minutes of incubation with 15 μg mL$^{-1}$ (FIG. 5).

Example 5.—Study of the Effect of IKB206 Tags on Chicken Microbiota

The objective of this paper is to obtain a molecule with a bactericidal effect on *E. coli* for application in both human and animal health. To that end, in order to demonstrate the specificity of this enzyme against *E. coli* and dismiss any possible interaction with bacterial microbiota present in chickens, and therefore the existence of any possible effects derived from said microbiota, the bactericidal activity of IKB206 on a battery of bacteria present in chickens more than 40 days old was analyzed (Proietti, P. C. et al. 2006), namely strains from S. xylosus, *E. avium, E. faecium* and *E. faecalis*. The results of FIG. 6 indicated that IKB206 has virtually no effect on the analyzed strains of chicken microbiota.

Example 6.—Study of Action Spectrum of IKB206

Figure 7:
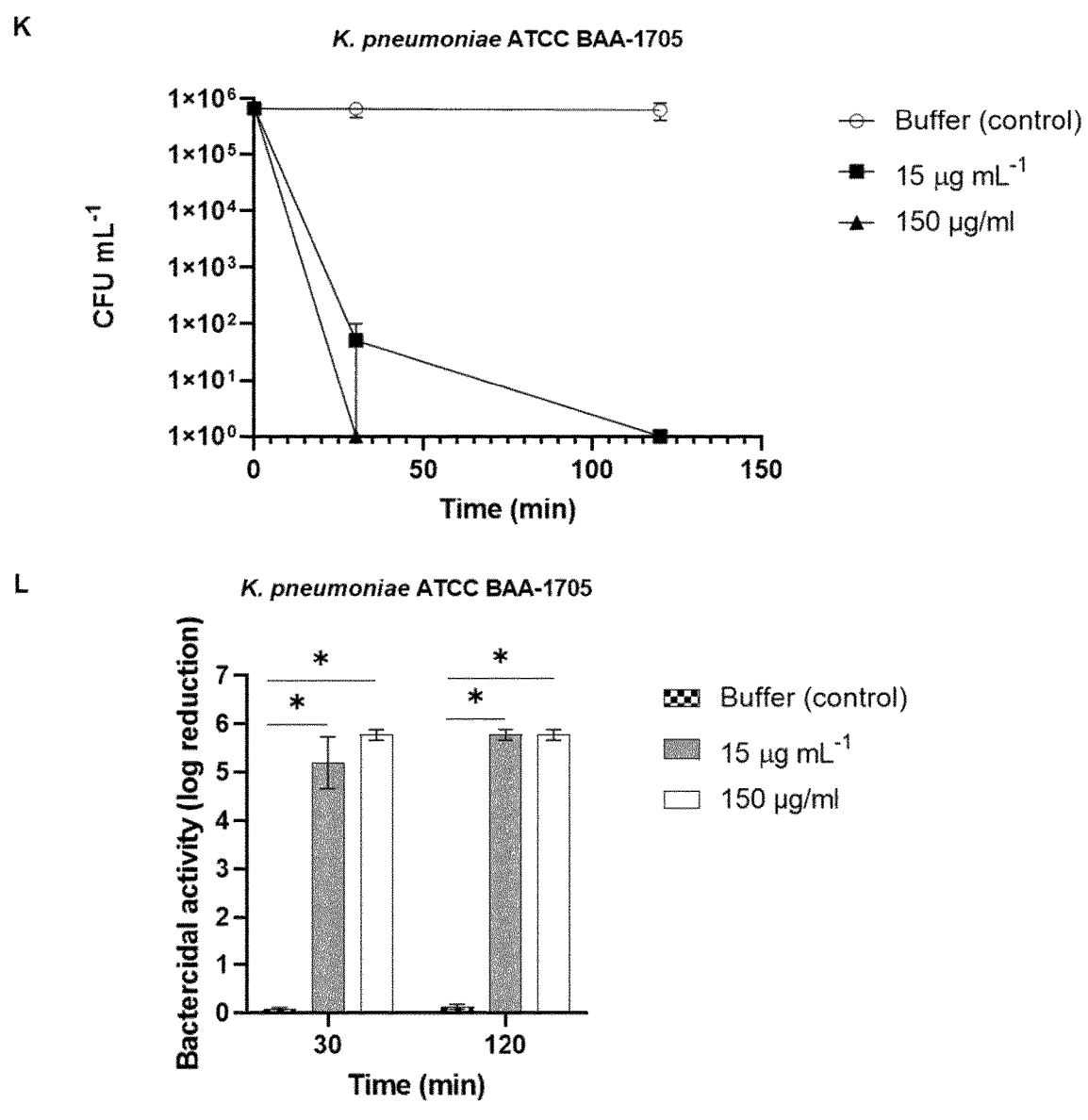
FIG. 7: Bactericidal effect of IKB206 on species of enterobacteria other than *E. coli*. The cultures were resuspended in buffer, adjusting the bacterial suspension to about 104-106 CFU mL$^{-1}$, and the cultures were incubated in the absence or presence of the enzyme at 30° C. (*E. cloacae* and *S. marcescens*) or 37° C. (*C. freundii* and *K. pneumoniae*) for 2 h. The data is representative of 2 to 4 independent experiments. Viable cells were determined by counting in LB agar plates. A, C, E, G, I, K and M) Bactericidal effect of expressed IKB206 on the reduction of CFU mL$^{-1}$ over time in the presence of 15 or 150 µg mL$^{-1}$ of the enzyme. B, D, F, H, J, L and N) Bactericidal effect of expressed IKB206 on the reduction of the number of logs over time in the presence of 15 or 150 µg mL$^{-1}$ of the enzyme. The error bars represent the standard error. The asterisks represent a significant difference (* P<0.05;  P<0.005; * P<0.0005) with respect to the control (buffer) according to: a T-test in the case of samples showing a normal distribution and homoscedasticity; and a U-Mann Whitney test in the case of samples not showing a normal distribution or showing heterogeneity of variances.
Figure 7:
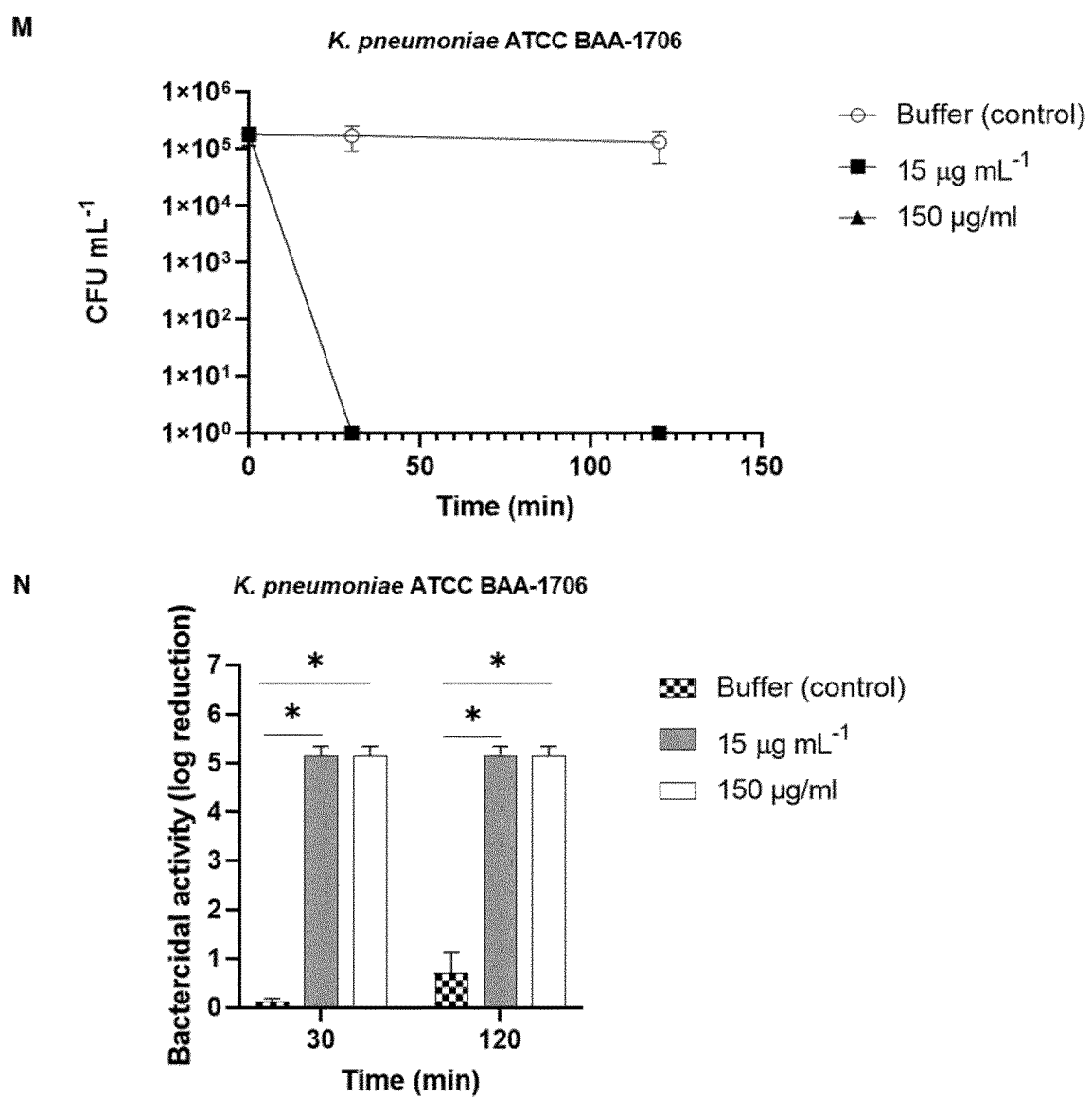
Figure 8:
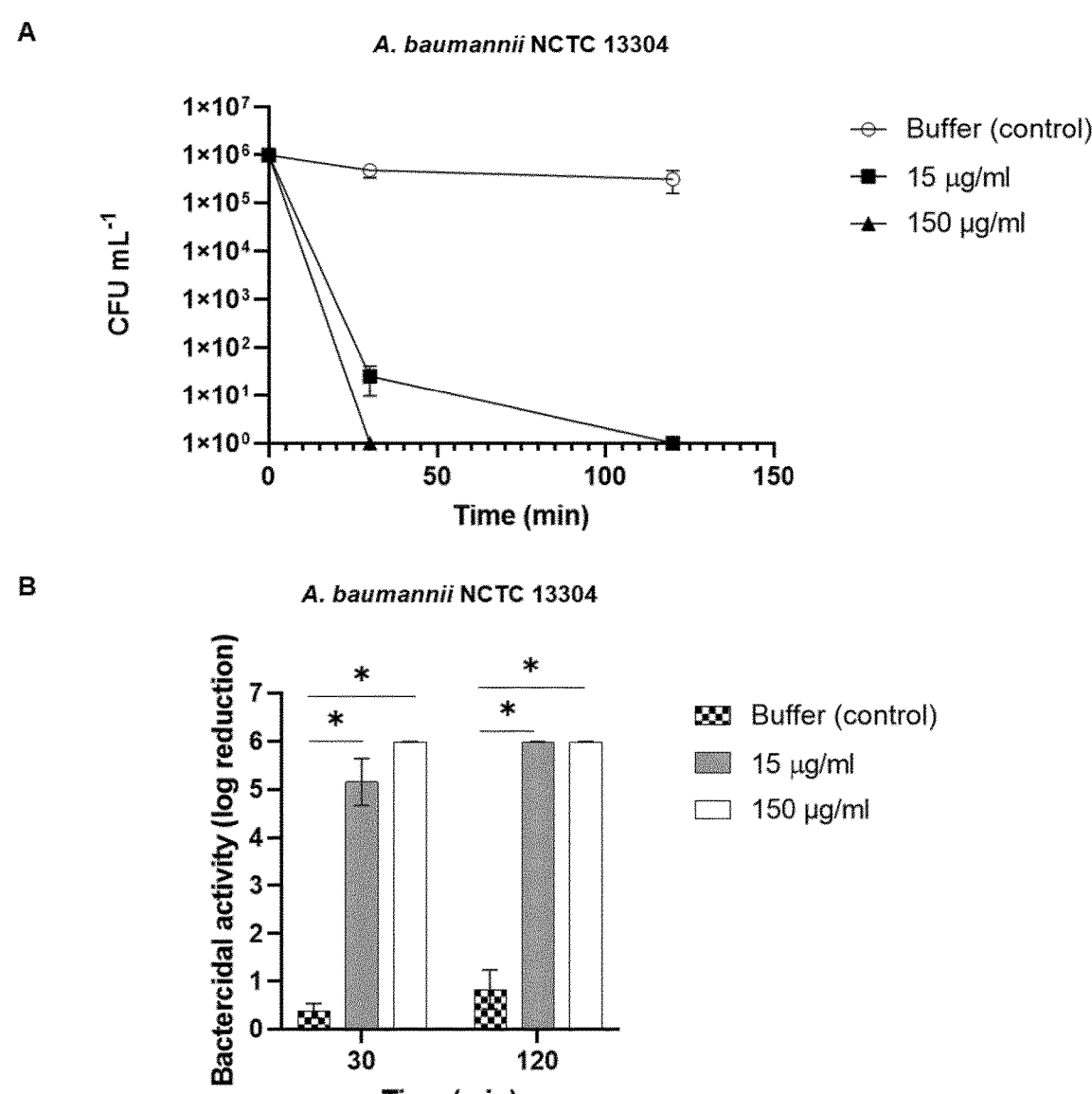
FIG. 8: Bactericidal effect of IKB206 on species of other non-enterobacteria Gram-negative bacteria. The cultures were resuspended in buffer, adjusting the bacterial suspension to about 105-$10^6$ CFU mL$^{-1}$, and the cultures were incubated in the absence or presence of the enzyme at 37° C. for 2 h. The data is representative of 4 independent experiments. Viable cells were determined by counting in LB agar plates. A, C, E and G) Bactericidal effect of expressed IKB206 on the reduction of CFU mL$^{-1}$ over time in the presence of 15 or 150 µg mL$^{-1}$ of the enzyme. B, D, F and H) Bactericidal effect of expressed IKB206 on the reduction of the number of logs over time in the presence of 15 or 150 µg mL$^{-1}$ of the enzyme. The error bars represent the standard error. The asterisks represent a significant difference (* P<0.05;  P<0.005; * P<0.0005) with respect to the control (buffer) according to: a T-test in the case of samples showing a normal distribution and homoscedasticity; and a U-Mann Whitney test in the case of samples not showing a normal distribution or showing heterogeneity of variances.
Figure 8:
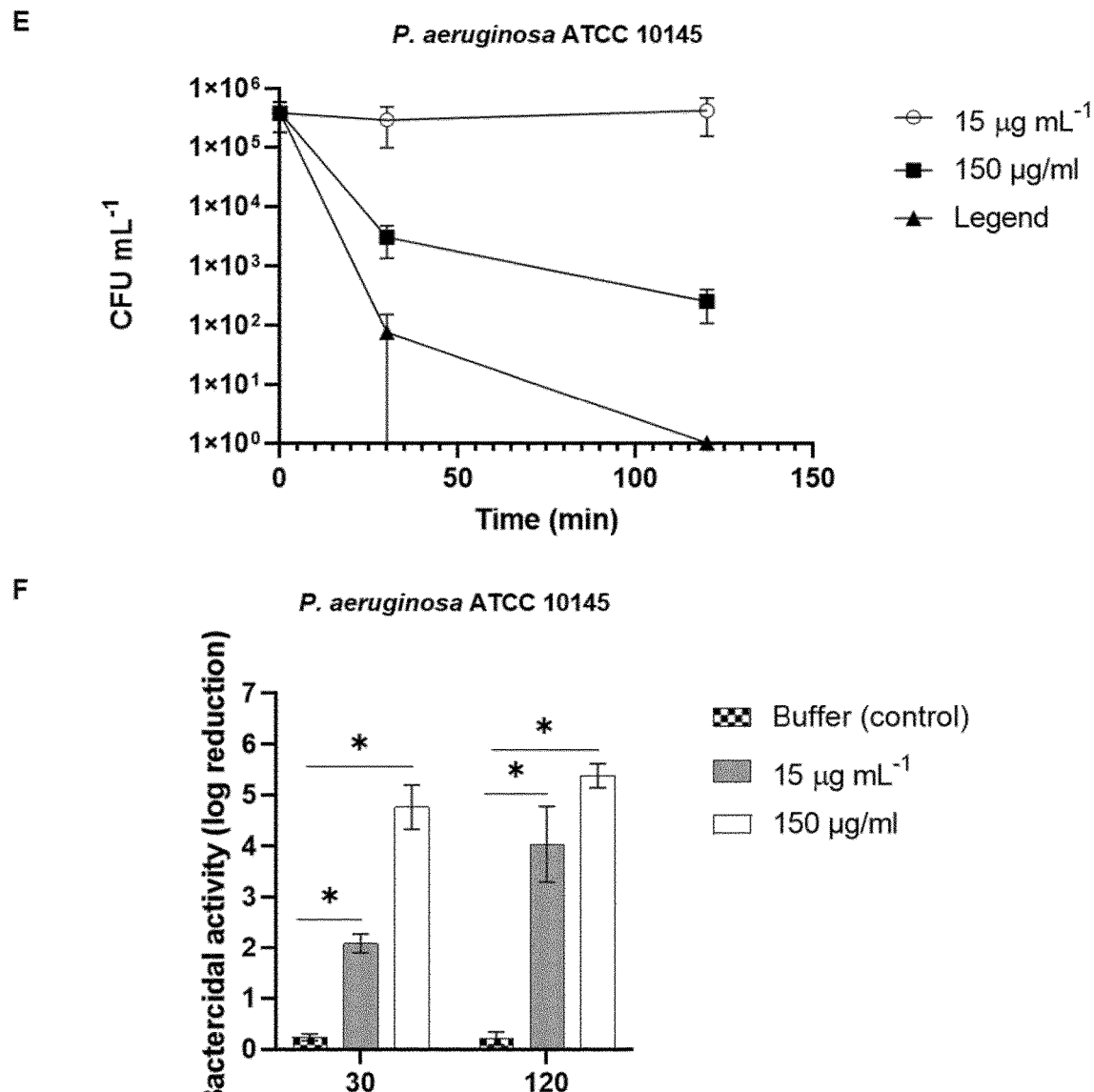
Figure 8:
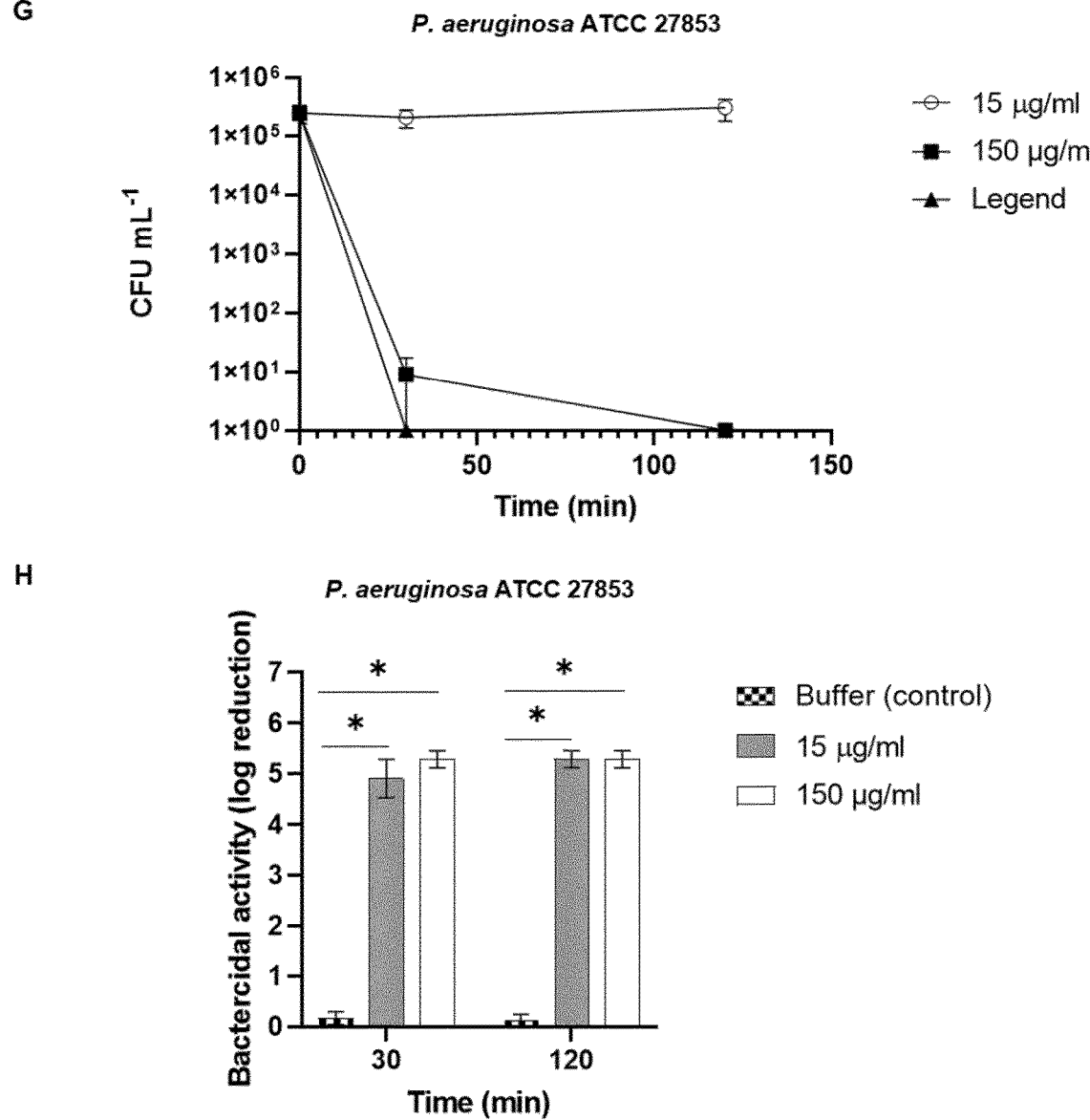

In addition, to determine the action spectrum of IKB206, we studied the bactericidal activity of this enzyme on other enterobacteria (*Citrobacter freundii, Enterobacter cloacae, Serratia marcescens* and *Klebsiella pneumoniae*) and other non-enterobacterial Gram-negative bacteria (*Acinetobacter baumannii* and *Pseudomonas aeruginosa*). Regarding the effect on enterobacteria, it can be observed in FIG. 7 that IKB206 exhibited a great bactericidal activity on *K. pneumoniae*, that is, a reduction of 4 or more logarithms was observed under the tested conditions. However, it did not show the same effect in *C. freundii* in which the bactericidal activity was significantly lower than that observed in *E. coli* or *K. pneumoniae*, although it was observed that this effect increased with incubation time. In the case of *S. marcescens*, IKB206 exerts a greater effect compared to *C. freundii*. Although the lethality observed in *E. coli* was not reached on *S. marcescens* in the incubation times tested, a much greater upward trend was observed with incubation time, reaching a bactericidal effect of almost 3 logarithms with an incubation time of 120 min. When expanding the study of the bactericidal activity on other non-enterobacterial Gram-negative bacteria, it was observed that IKB206 also presents a great bactericidal activity against *A. baumannii* and *P. aeruginosa*, obtaining reductions in CFU/mL of more than 4-logs (FIG. 8).

Example 7.—Study of the Mechanism of Action of IKB206

To study the mechanism of action of IKB206, the secondary structure of the enzyme was modelled and the importance of the domain D8 in the activity of IKB206 was determined.

To determine the putative protein structure of IKB206, a structural model of the catalytic and the D8 domain were built separately using the online available softwares Phyre2 (Kelley L A et al. 2015) and Swissmodel (Waterhouse A et al. 2018) (FIG. 9A and B).

The D8 domain was built using as template the N-terminal LysM domain of a putative endopeptidase of Termus thermofilus (Wong J E et al. 2015). The output model of the catalytic domain was built using as template the crystal structure of the *Acinetobacter baumanii* AB 5075UW2 prophage muramidase (Sykilinda N N et al. 2018). The structural model of the catalytic domain revealed an overall fold similar to the T4 lysozyme and other T4 lysozyme-like endolysins such us P22 phage lysozyme (Mooers B H et al. 2006) or the endolysin encoded by the *Escherichia coli* DLP12 prophage (Babu K et al. 2018). The catalytic mechanism of the T4 lysozyme is well described and so are the residues involved in the catalytic reaction (Rennel D et al, 1991; Kuroki R et al, 1995; Kuroki R et al, 1999). It has been also shown that other endolysins such us P21 and P22 have similar amino acids in the catalytic cleft (Xu M, et al. 2005; Mooers B H et al. 2006, Maciejewska B et al. 2017) constituting what it is known as the catalytic triad, usually formed by the E-8aa-D/C-5aa-T motif (Babu K et al. 2018). The presence of this motif has been described as a hallmark of the T4 lysozyme-like endolysins (Sun Q et al. 2009, Maciejewska B et al. 2017, Babu K et al. 2018). The sequence of IKB206 reveals that residues E15, D24 and T33 are well aligned (FIG. 9, D) with the catalytic residues of DLP12 endolysin, T4 lysozyme, P22 lysozyme and BA 5075UW muramidase (Babu K et al. 2018, Daopin S et al. 1991, Mooers B H et al. 2006, Sykilinda N N et al. 2018 respectively), all of them identified as T4 lysozyme-like endolysins. Moreover, the structural superimposition of the structural model of IKB206 against the crystal structures of these endolysins (FIG. 9, C) (PDB codes 1L48, 4ZPU, 2ANV and 6ET6 respectively), together with the sequence alignment show that E15, D24 and T33 could constitute the catalytic triad of IKB206. Another structural feature of T4 lysozyme is the presence of a salt bridge between R145 and the catalytic E11 (Rennel D et al, 1991, Babu K et al. 2018). The presence of a salt bridge between the catalytic glutamic acid and an arginine located near the C-terminal region is conserved among other T4 lysozyme-like endolysins (Babu K et al. 2018). It has been proposed that the role of this salt bridge is to orientate the position of the glutamate side chain inside the catalytic cleft (Rennel D et al, 1991; Babu K et al. 2018). In the structural model of IKB206, R139 may form a salt bridge with E15 which supports the hypothesis that E15 is one of the catalytic residues of IKB206.

These findings support the idea that the catalytic domain of IKB206 belongs to the T4 lysozyme-like endolysins and residues E15, D24 and T33 form the catalytic triad of the enzyme.

To determine the importance of the domain D8, the protein corresponding only to the catalytic domain was obtained, IKB206AD8. The overexpression of this construct was carried out in LB broth. Protein overexpression was inducted with 1 mM IPTG when the $A_{600}$ reached ≈0.8 for 16 h at 25° C. and 200 rpm. IKB206AD8 was purified by means of cation exchange chromatography at pH 8.5 (pI≈9.5). FIG. 2C shows the obtained protein purity. The molecular weight of the band corresponds with the in silico molecular weight of the protein, which is 17.54 kDa. The assays for the determination of the bactericidal activity of IKB206AD8 in *E. coli* strain ATCC 25922 showed that in the absence of the D8 domain, the polypeptide presented bactericidal activity. However, longer incubation times were needed to obtain the same levels of bactericidal activity as IKB206 (FIG. 10).

Example 8.—Study of the Efficacy of IKB206 Tags in In Vivo Sepsis Model

To enable determining if IKB206 tags is effective in the treatment of infections by *E. coli* in living beings, a series of assays were performed in which the efficacy of this molecule was evaluated on an *E. coli*-induced sepsis model in zebrafish.

Figure 11:
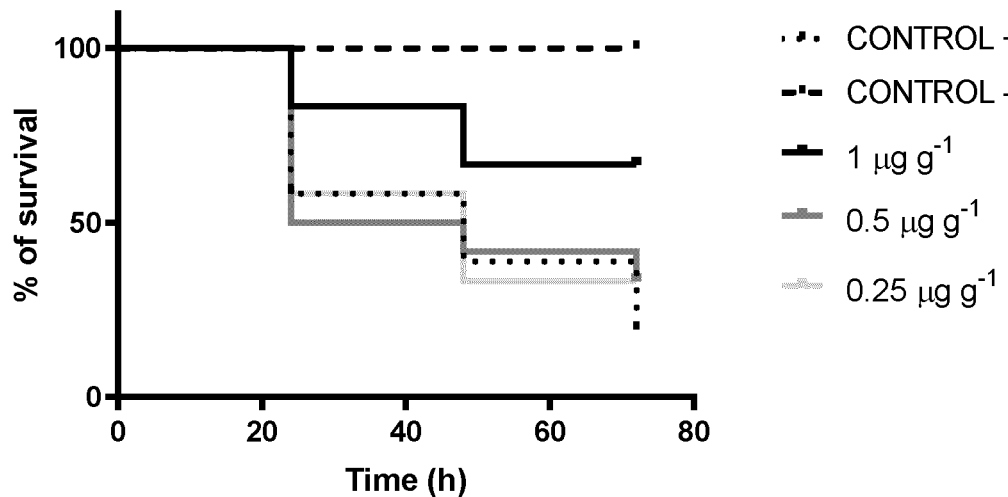
FIG. 11: Zebrafish survival curves in an infection experiment. The lines represent the survival of zebrafish treated or not treated with different concentrations of IKB206$_{tags}$. The black line corresponds with zebrafish treated with 1 μg g-1, the dark grey line to those treated with 0.5 μg g-1, the light grey line to those treated with 0.25 μg g-1, and the dotted line corresponds with zebrafish that have not been treated. Twelve zebrafish per condition were infected with 5.5×10$^7$ CFU mL$^{-1}$ of *E. coli* ATCC 25922. The results were statistically significant (P=0.001) when treated zebrafish were compared to the untreated control (Mantel-Cox test).

The intraperitoneal (IP) route is chosen for an infection model as it is easy and quick to implement, turning this technique into one that is particularly indicated for use in different groups of experimentation animals. One hour after infection with *E. coli* ATCC 25922, different doses of IKB206 were administered to each of the groups. A high protective capacity was observed 72 hpi, protecting 66.6%, 33.3%, and 16.6% in a decreasing order of concentration used (FIG. 11). Furthermore, to determine the toxicity of IKB206 in adult fish, assays in which uninfected fish were inoculated with the highest amount of protein used in the efficacy assays (1 µg g-1) were performed. It was observed that there were no differences between fish injected with the protein buffer and fish injected with 1 µg g-1 of protein (data not shown).

Example 9.—Study of the Toxicity of IKB206$_{tags}$ on Human Cells

Figure 12:
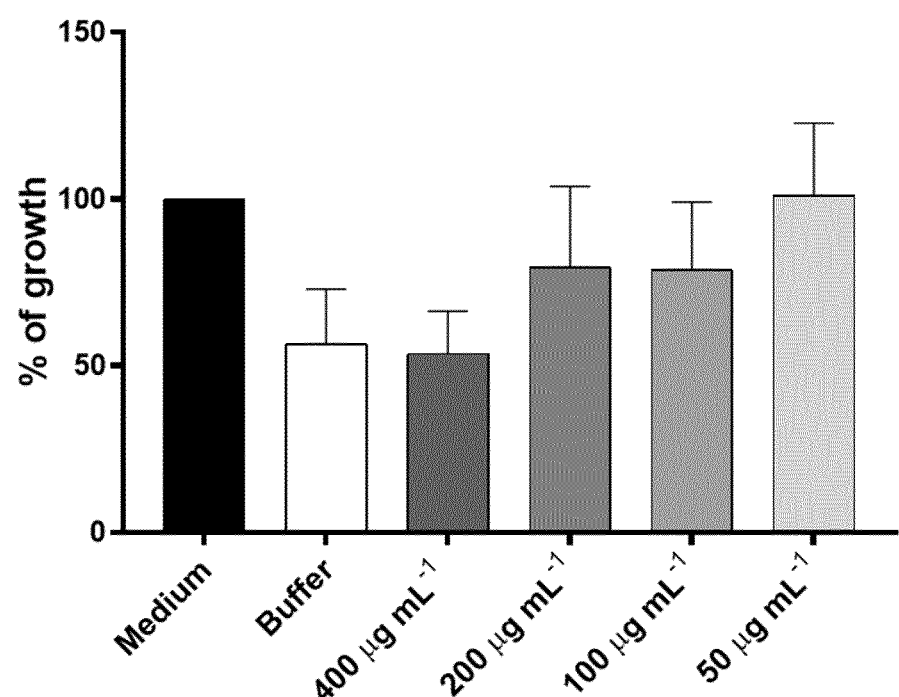
FIG. 12: Cytotoxicity assay on human HEK293 cells. The cytotoxicity of a range of concentrations from 50 to 400 μg mL$^{-1}$ was analyzed. The culture medium in which the cells grow was used as negative control. The data is the mean of 3 independent experiments and statistically analyzed by means of a Tukey test.

To determine the toxicity of IKB206$_{tags}$ on human cells for the possible application of IKB206 in humans, a toxicity assay was performed on a human HEK293 cell line. The buffer in which the IKB206$_{tags}$ protein is dissolved was included in case the toxicity of the assay was associated with the buffer and not the protein. As shown in FIG. 12, no significant differences (p>0.05) were observed between the control (culture media) and the different assayed concentrations.

Example 10.—Study of the Possible Synergistic Effect Between the IKB206$_{tags}$ and Antibiotics Synergistic Effect of IKB206$_{tags}$ & Carbapenem Antibiotics Exploring combinations of two or more antibacterials can be useful because they may act synergistically and, thus, it is an effective way to improve the bactericidal activity of individual drugs. To test the bactericidal effect of IKB206$_{tags}$ combined with antibiotics, we tested some of the drugs most commonly used against MDR *E. coli* disease (Hawkey P.M. et al. 2018). In particular, we used two antibiotics belonging to the carbapenem group. As *E. coli* strain, we selected the standard *E. coli* strain according to the CLSI guidelines, *E. coli* strain ATCC 25922.

Figure 13:
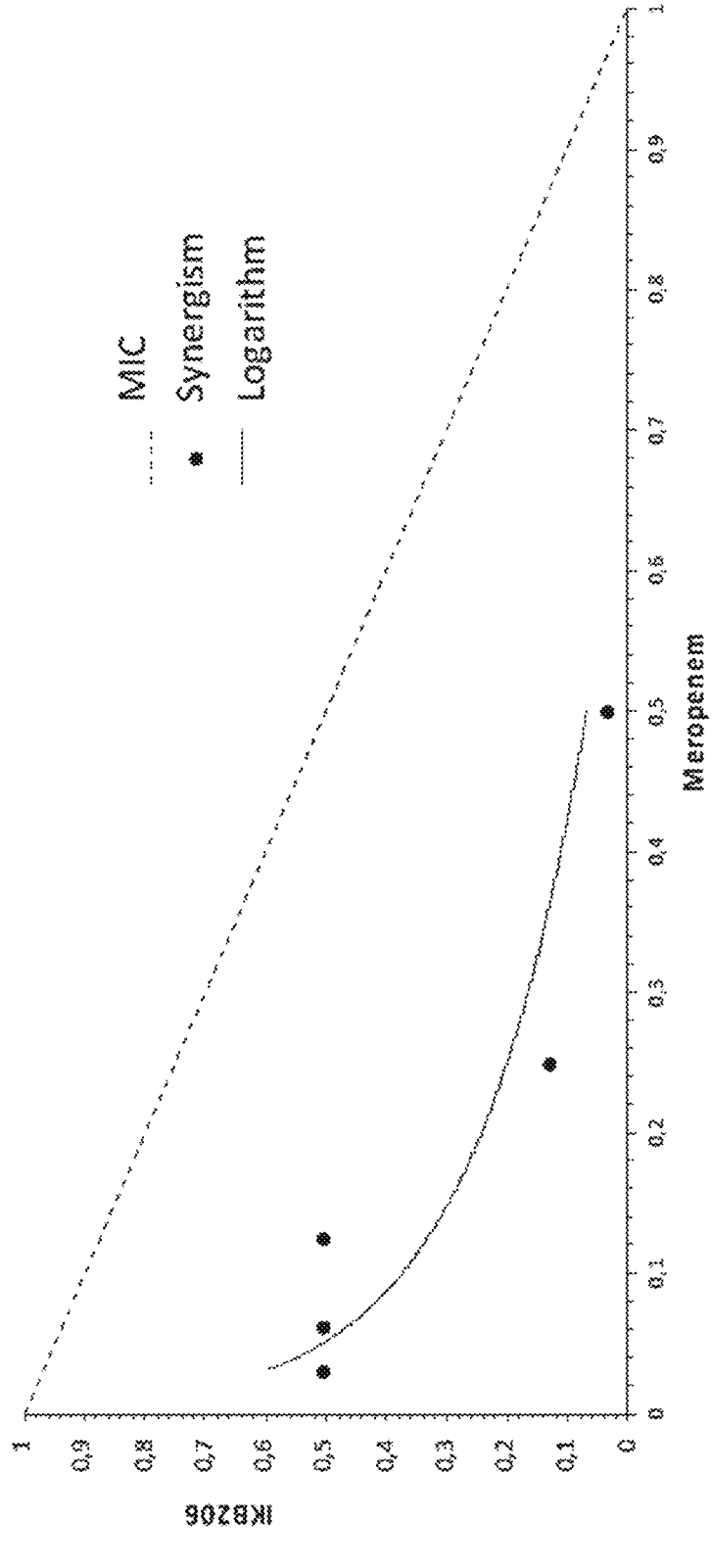
FIG. 13: Representation of Isobolograms (A) IKB206$_{tags}$+meropenem and (B) IKB206$_{tags}$+imipenem. The points below the dotted line representing the MIC are found to be synergistic.
Figure 13:
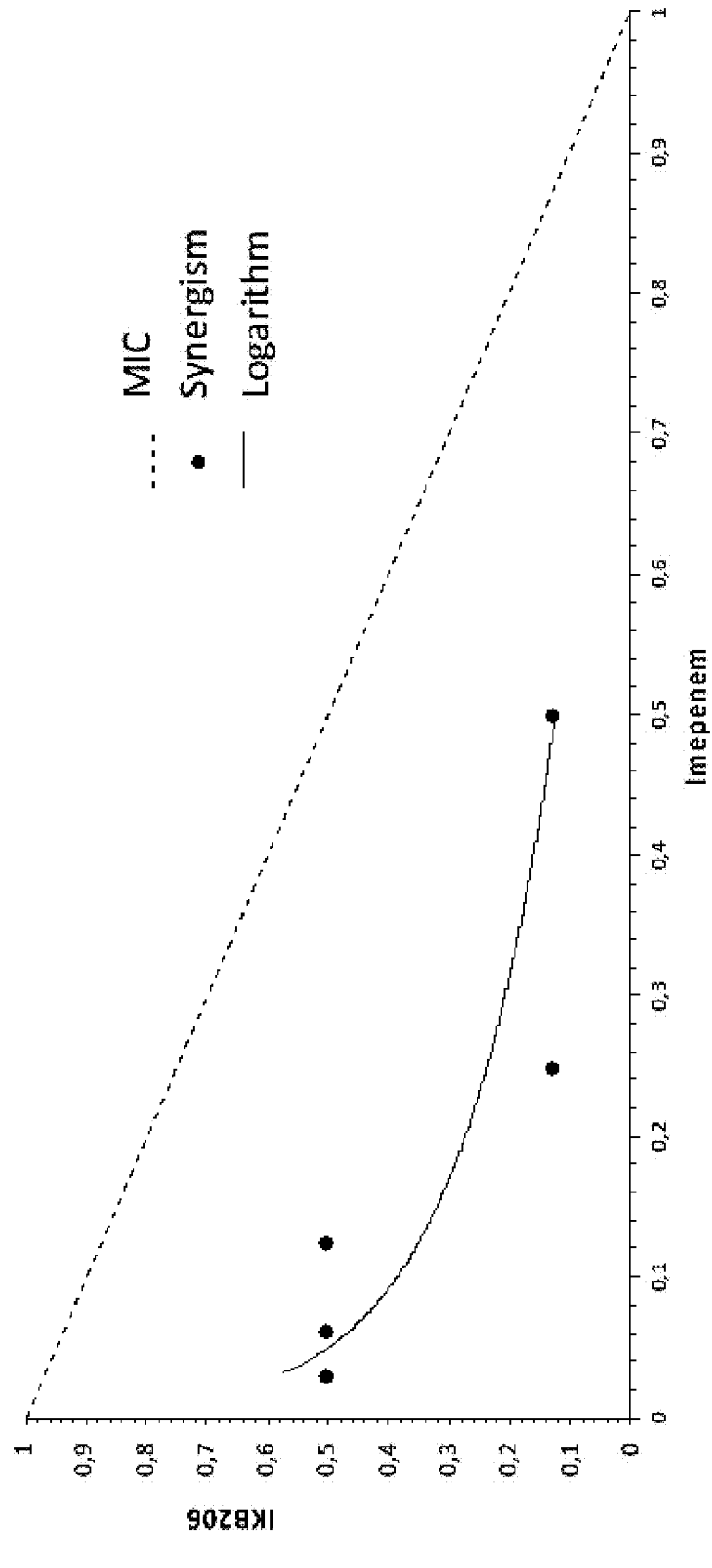

The results of checkerboard in vitro studies testing the combinations used (IKB206$_{tags}$ and antibiotics) are summarized in Table 3 and 4, and the isobolograms for each combination of endolysin and antibiotic are shown in FIG. 13. These data demonstrated both synergistic and additive effects, depending on the particular antibiotic. Interestingly, none of the combinations produced indifferent or antagonistic effects. Synergism was seen using meropenem or imipenem in combination with IKB206$_{tags}$.

TABLE 3

FICI values obtained from the combination between meropenem and IKB206$_{tags}$ through the checkerboard method.

| | | Meropenem | | | | | | | |
| --- | --- | --- | --- | --- | --- | --- | --- | --- | --- |
| | | Absence | 0.03 × MIC | 0.06 × MIC | 0.12 × MIC | 0.25 × MIC | 0.5 × MIC | MIC | 2 × MIC |
| IKB206 | 2 × MIC | | | | | | | | |
| | MIC | | | | | | | | |
| | 0.5 × MIC | | *0.51* | *0.56* | *0.57* | | | | |
| | 0.25 × MIC | | | | | 0.37 | | | |
| | 0.12 × MIC | | | | | | | | |
| | 0.06 × MIC | | | | | | | | |
| | 0.03 × MIC | | | | | | *0.53* | | |
| | Absence | | | | | | | | |

The values that appear in bold indicate synergy and italics partial synergism, the stripers boxes indicate bacterial growth.

TABLE 4

FICI values obtained from the combination between imipenem and IKB206$_{tags}$ through the checkerboard method.

| | | Imipenem | | | | | | |
| --- | --- | --- | --- | --- | --- | --- | --- | --- |
| | | Absence | 0.03 × MIC | 0.06 × MIC | 0.12 × MIC | 0.25 × MIC | 0.5 × MIC | MIC |
| IKB206 | 2 × MIC | | | | | | | |
| | MIC | | | | | | | |
| | 0.5 × MIC | | *0.51* | *0.56* | *0.57* | | | |
| | 0.25 × MIC | | | | | | | |
| | 0.12 × MIC | | | | | 0.37 | 0.62 | |
| | 0.06 × MIC | | | | | | | |
| | 0.03 × MIC | | | | | | | |
| | Absence | | | | | | | |

The values that appear in bold indicate synergy and italic partial synergism, the stripes boxes indicate bacterial growth.

Time-Killing Analysis of Drug Combinations Against *E. coli* Strain

To confirm the possible synergistic activities of IKB206$_{tags}$ with meropenem and imipenem, time-killing assays were performed against the *E. coli* strain ATCC 25922. The range of antibiotics and IKB206$_{tags}$ concentrations was determined according to the checkerboard and isobologram results. These concentrations were used for each treatment, either with a single agent or in combination. The results shown in FIG. 14 demonstrated that the combinations with antibiotic and IKB206 were effective at doses below the MIC of the tested compounds.

Moreover, at some of the tested concentrations the effect was shown to be synergistic, namely where the viable cells were reduced at least 2 log units after 17 h of treatment with respect to the control, in agreement with the CLSI guidelines.

Overall, initial checkerboard experiments suggested a synergistic effect for antibiotics of the carbapenem group. These results were confirmed by the time-killing assays with *E. coli* ATCC 25922 strain which showed clear synergistic effects when meropenem and imipenem were combined with IKB206$_{tags}$.

BIBLIOGRAPHY (1) Farber, L. Antibiotics in Food Preservation. Annu. Rev. Microbiol. 1959. 13:125-140.
(2) Davies, J. y Davies, D. Origins and evolution of antibiotic resistance. Microbiol. Mol. Biol. Rev. MMBR. 2010. 74:417-4335.
(3) Frankel, R. B.; Kalmijn, A. J.; Amann, R.; Ludwig, W.; Petersen, N.; Arakaki, A.; Matsunaga, T.; Bleil, U.; Kirschvink, J. L.; Sievert, S. M.; et al. Sampling the Antibiotic Resistome. Science. 2006. 311:374-378.
(4) Tenover, F. C. Mechanisms of antimicrobial resistance in bacteria. Am. J. Infect. Control. 2006. 34: S3-S10.
(5) Starrels, J. L.; Barg, F. K.; Metlay, J. P. Populations at Risk Patterns and Determinants of Inappropriate Antibiotic Use in Injection Drug Users. J. Gen. Intern. Med. 2009. 24:263-269.
(6) Manjusha Lekshmi 1, Parvathi Ammini 2, Sanath Kumar 1 and Manuel F. Varela 3. The Food Production Environment and the Development of Antimicrobial Resistance in Human Pathogens of Animal Origin. Microorganism. 2017. 5:11.
(7) Smith, K. E.; Besser, J. M.; Hedberg, C. W.; Leano, F. T.; Bender, J. B.; Wicklund, J. H.; Johnson, B. P.; Moore, K. A.; Osterholm, M. T. Quinolone-resistant *Campylobacter jejuni* infections in Minnesota, 1992-1998. Investigation Team. N. Engl. J. Med. 1999. 340:1525-1532.
(8) WHO. The World Is Running Out of Antibiotics, WHO Report Confirms. 2017.
(9) O'Neill, J. Tackling Drug-Restistant Infections Globally: Final Report and Recommendations. 2016.
(10) Adeyi, O. O.; Baris, E.; Jonas, O. B.; Irwin, A.; Berthe, F. C. J.; Le Gall, F. G.; Marquez, P. V.; Nikolic, I. A.; Plante, C. A.; Schneidman, M.; et al. Drug-Resistant Infections: A Threat to Our Economic Future; Final Report; World Bank Group: Washington, DC, USA, 2017.
(11) Antilles N, Blanco A, Camprubí Q, Jove R y Biarnés M. Análisis de resistencias a antimicrobianos de cepas de *E.*

51

*coli* aisladas en aves en España de 1998 a 2013 Centre de Sanitat Avícola de Catalunya i Aragó (CESAC) Reus, Tarragona, España.

(12) Czaplewski, L.; Bax, R.; Clokie, M.; Dawson, M.; Fairhead, H.; Fischetti, V. A.; Foster, S.; Gilmore, B. F.; Hancock, R. E.; Harper, D.; et al. Alternatives to antibiotics-a pipeline portfolio review. Lancet Infect. Dis. 2016. 16:239-251.

(13) Hermoso J. A., García J. L. and García P. Taking aim on bacterial pathogens: from phage therapy to enzybiotics. Curr. Opin. Microbiol. 2007. 10:461-472.

(14) Fischetti V. A., Nelson D. and Schuch R. Reinventing phage therapy: are the parts greater than the sum? Nat. Biotechnol. 2006. 24:1508-11.

(15) Pires, D. P.; Oliveira, H.; *Melo*, L. D.; Sillankorva, S. and Azeredo, J. Bacteriophage-encoded depolymerases: Their diversity and biotechnological applications. Appl. Microbiol. Biotechnol. 2016. 100, 2141-2151.

(16) Nelson D., Loomis L. and Fischetti V. A. Prevention and elimination colonization of mice by group A streptococci by using a bacteriophage lytic enzyme. Proc. Natl. Acad. Sci. USA. 2001. 98:4107-4112.

(17) Yoong P., Schuch R., Nelson D. and Fischetti V. A. Identification of a broadly active phage lytic enzyme with lethal activity against antibiotic-resistant *Enterococcus faecalis* and *Enterococcus faecium*. J Bacteriol. 2004. 186:4808-4812.

(18) Zimmer M., Vukov N., Scherer S. and Loessner M. J.: The murein hydrolase of the bacteriophage φ3626 dual lysis system is active against all tested *Clostridium perfringens* strains. Appl. Environ. Microbiol. 2002. 68:5311-5317.

(19) Cheng Q., Nelson D., Zhu S. and Fischetti V. A.: Removal of group B streptococci colonizing the vagina and oropharynx of mice with a bacteriophage lytic enzyme. Antimicrob. Agents Chemother. 2005. 49:111-117.

(20) McCullers J. A., Karlström A., Iverson A. R., Loeffler J. M. and Fischetti VA: Novel strategy to prevent otitis media caused by colonizing *Streptococcus pneumoniae*. PLOS Pathog. 2007. 3: e28.

(21) Schmelcher M.; Tchang V. S. and Loessner M. J. Domain shuffling and module engineering of *Listeria* phage endolysins for enhanced lytic activity and binding affinity. Microb. Biotechnol. 2011. 4, 651-662.

(22) Díez-Martínez, R.; De Paz H. D.; García-Fernández, E.; Bustamante, N.; Euler, C. W.; Fischetti, V. A.; Menendez, M. and Garcia, P. A novel chimeric phage lysin with high in vitro and in vivo bactericidal activity against *Streptococcus pneumoniae*. J. Antimicrob. Chemother. 2015.70, 1763-1773.

(23) Becker S. C.; Foster-Frey J.; Stodola A. J.; Anacker D. and Donovan D. M. Differentially conserved staphylococcal SH3b_5 cell wall binding domains confer increased staphylolytic and streptolytic activity to a streptococcal prophage endolysin domain. Gene. 2009. 443: 32-41.

(24) Yang H.; Linden S. B.; Wan J.; Yu J.; Nelson D. C. and Wei, H. A chimeolysin with extended-spectrum streptococcal host range found by an induced lysis-based rapid screening method. Sci. Rep. 2015. 5, 17257.

(25) Yang H.; Bi Y.; Shang X.; Wang M.; Linden S. B.; Li Y.; Nelson D. C. and Wei H. Antibiofilm activities of a novel chimeolysin against *Streptococcus mutans* under physiological and cariogenic conditions. Antimicrob. Agents Chemother. 2016. 60:7436-7443.

(26) Briers Y. and Lavigne R. Breaking barriers: Expansion of the use of endolysins as novel antibacterials against Gram-negative bacteria. Future Microbiol. 2015. 10:377-390.

(27) Briers Y., Walmagh M., Van Puyenbroeck V. et al. Engineered endolysin-based 'Artilysins' to combat multidrug-resistant Gram-negative pathogens. MBio. 2014. 5 (4): e 01379-e 01414.

(28) Wang, S., Gu, J., Lv, M., Guo, Z., Yan, G., et al. The antibacterial activity of *E. coli* bacteriophage lysin Lysep3 is enhanced by fusing the *Bacillus amyloliquefaciens* bacteriophage endolysin binding domain D8 to the C-terminal region. J Microbiol. 2017. 55 (5): 403-408.

(29) Heselpoth, R. D., Euler, C. W., Schuch, R. y Fischetti, V. A. Lysocins: Bioengineered Antimicrobials that Deliver Lysins Across the Outer Membrane of Gram-Negative Bacteria. 2019. Antimicrob. Agents Chemother. doi: 10.1128/AAC.00342-19

(30) Loessner, M. J., Kramer, K., Ebel, F. y Scherer, S. C-terminal domains of *Listeria monocytogenes* bacteriophage murein hydrolases determine specific recognition and high-affinity binding to bacterial cell wall carbohydrates. Mol. Microbiol. 2002. 44:335-349.

(31) Schmelcher, M., Shabarova, T., Eugster, M. R., Eichenseher, F., Tchang, V. S., Banz, M., et al. Rapid multiplex detection and differentiation of *Listeria* cells by use of fluorescent phage endolysin cell wall binding domains. Appl. Environ. Microbiol. 2010. 76:5745-5756.

(32) Tikhe, C., and Husseneder, C. Whole genome sequencing and characterization of *Enterobacter* phage Arya isolated from the termite gut. Direct submission National Center for Biotechnology Information, NIH. 2016

(33) Morita, M., Tanji, Y., Orito, Y., Mizoguchi, K., Soejima, A. and Unno, H. Functional analysis of antibacterial activity of *Bacillus amyloliquefaciens* phage endolysin against Gram-negative bacteria. FEBS Letters. 2001. 500: 56-59.

(34) Proietti, P. C., Castellini, C., Pedrazzoli, M., Dal Bosco, A. and Franciosini, M. Bacterial Counts and Characterization of Intestinal Flora in Organic and Conventional Chickens. World's Poultry Science Association (WPSA), Beekbergen, the Netherlands. 2006.

(35) OECD GUIDELINES FOR TESTING OF CHEMICALS: Fish Embryo Acute Toxicity (FET) Test, in 236.

(36) David A and Pancharatna K. Effects of acetaminophen (paracetamol) in the embryonic development of zebrafish, *Danio rerio*. J Appl Toxicol. 2009 7:597-602.

(37) Fischetti, V., Nelson, D. and Schuch, R. Reinventing phage therapy: are the parts greater than the sum? Nat Biotechnology. 2006. 24 (12): 1508-11.

(38) Vázquez, R., García, E. and García, P. Phage Lysins for Fighting Bacterial Respiratory Infections: A New Generation of Antimicrobials. Front Immunol. 2018. 9:2252.

(39) São-José, C. Engineering of Phage-Derived Lytic Enzymes: Improving Their Potential as Antimicrobials. Antibiotics. 2018. 7, 29.

(40) Orito Y., Morita, M., Hori, K., Unno, H. and Tanji, Y. *Bacillus amyloliquefaciens* phage endolysin can enhance permeability of *Pseudomonas aeruginosa* outer membrane and induce cell lysis. Appl Microbiol Biotechnol. 2004. 65 (1): 105-9.

(41) Hojckova, K., Stano, M. y Klucar, L. phiBIOTICS: catalogue of therapeutic enzybiotics, relevant research studies and practical applications. BMC Microbiol. 2013. 13:53.

(42) Letrado P., Corsini, B., Díez-Martínez, R., Bustamante, N., Yuste, J. E. and García, P. Bactericidal synergism between antibiotics and phage endolysin Cpl-711 to kill multidrug-resistant pneumococcus. Future Microbiol. 2018. 13 (11): 1215-1223.

(43) Vázquez, R., Domenech, M., Iglesias-Bexiga, M., Menéndez, M. and García, P. Csl2, a novel chimeric bacteriophage lysin to fight infections caused by *Streptococcus suis*, an emerging zoonotic pathogen. Sci Rep. 2017. 7 (1): 16506.

(44) Hooper, L. V., Littman, D. R. and Macpherson, A. J. Interactions between the microbiota and the immune system. Science. 2012. 336 (6086): 1268-1273.

(45) Ley, R. E., Turnbaugh, P. J., Klein, S. and Gordon, J. I. Microbial ecology: human gut microbes associated with obesity. Nature. 2006. 444:1022.

(46) Cani, P. D. and Delzenne, N. M. The role of the gut microbiota in energy metabolism and metabolic disease. Curr Pharm Des. 2009. 15:1546-1558.

(47) Claus, S. P., Ellero, S. L., Berger, B., Krause, L., Bruttin, A., et al. Colonization-induced host-gut microbial metabolic interaction. Mol Bio. 2011. 2: e00271-e00210.

(48) Spor, A., Koren, O. and Ley, R. Unravelling the effects of the environment and host genotype on the gut microbiome. Nat Rev Microbiol. 2011. 9:279.

(49) Schulfer A. F., Battaglia, T., Alvarez, Y., Bijnens, L., Ruiz, V. E., et al. Intergenerational transfer of antibiotic-perturbed microbiota enhances colitis in susceptible mice. Nat Microbiol. 2018. 3:234.

(50) Le Roy, C. I., Woodward, W. J., Ellis, R. J., La Ragione, R. M. and Claus, S. P. Antibiotic treatment triggers gut dysbiosis and modulates metabolism in a chicken model of gastro-intestinal infection. BMC Vet Res. 2019. 25 (1): 37.

(51) Kelley L. A, Mezulis S, Yates C. M, Wass M. N, Sternberg M. J. The Phyre2 web portal for protein modeling, prediction and analysis. Nat Protoc. 2015 June; 10 (6): 845-58. doi: 10.1038/nprot.2015.053.

(52) Waterhouse, A., Bertoni, M., Bienert, S., Studer, G., Tauriello, G., Gumienny, R., Heer, F. T., de Beer, T. A. P., Rempfer, C., Bordoli, L., Lepore, R., Schwede, T. SWISS-MODEL: homology modelling of protein structures and complexes. Nucleic Acids Res. 46 (W1), W296-W303 (2018)

(53) Daopin, S., Alber, T., Baase, W. A., Wozniak, J. A., Matthews, B. W. Structural and thermodynamic analysis of the packing of two alpha-helices in bacteriophage T4 lysozyme. (1991) J Mol Biol 221:647-667

(54) Babu K, Arulandu A, Sankaran K. The structure of DLP12 endolysin exhibiting alternate loop conformation and comparative analysis with other endolysins. Proteins. 2018 Feb; 86 (2): 210-217. Doi: 10.1002/prot.25428. Epub 2017 Dec. 1.

(55) Mooers, B. H., Matthews, B. W. Extension to 2268 atoms of direct methods in the ab initio determination of the unknown structure of bacteriophage P22 lysozyme. (2006) Acta Crystallogr D Biol Crystallogr 62:165-176

(56) Sykilinda N N, Nikolaeva A Y, Shneider M M, Mishkin D V, Patutin A A, Popov V O, Boyko K M, Klyachko N L, Miroshnikov K A Structure of an *Acinetobacter* Broad-Range Prophage Endolysin Reveals a C-Terminal a-Helix with the Proposed Role in Activity against Live Bacterial Cells. Viruses. 2018 Jun. 6; 10 (6): 309. doi: 10.3390/v10060309.

(57) Schmelcher M, Donovan D M, Loessner M J.; Bacteriophage endolysins as novel antimicrobials. Future Microbiol. 2012; 7 (10): 1147-1171.

(58) Minogue T D, Daligault H A, Davenport K W, Bishop-Lilly K A, Broomall S M, Bruce D C, Chain P S, Chertkov O, Coyne S R, Freitas T, Frey K G, Gibbons H S, Jaissle J, Redden C L, Rosenzweig C N, Xu Y, Johnson S L. Complete Genome Assembly of *Escherichia coli* ATCC 25922, a Serotype 06 Reference Strain. Genome Announc. 2014 September-Oct; 2 (5): e00969-14.

(59) Nelson D C, Schmelcher M, Rodriguez-Rubio L, Klumpp J, Pritchard D G, Dong S, Donovan D M., Endolysins as antimicrobials, Adv Virus Res. 2012; 83:299-365.

(60) Vaara M. Agents that increase the permeability of the outer membrane. Microbiol Rev. 56 (3): 395-441 (1992).

(61) Studier F W. Protein production by auto-induction in high density shaking cultures. Protein Expr Purif. 2005 May; 41 (1): 207-34. doi: 10.1016/j.pep.2005.01.016

(62) Santin and Cascales. Measure of peptidoglycan hydrolase activity. Methods Mol Biol. 1615:151-158 (2017).

(63) European Centre for Disease Prevention and Control. Surveillance of antimicrobial resistance in Europe-Annual report of the European Antimicrobial Resistance Surveillance Network (EARS-Net) 2017. Stockholm: ECDC; 2018.

(64) Moody J A. Synergism testing: broth microdilution checkerboard and broth macrodilution methods. In: Isenberg H D, editor. Clinical Microbiology Procedures Handbook. American Society for Microbiology; DCUSA: 1992. pp. 5.18.1-28.

(65) Moellering E G., Jr. Antimicrobial combinations. In: Lorian V, editor. Antibiotics in Laboratory Medicine. The Williams & Wilkins Co.; MDUSA: 1996. pp. 330-396

(66) Pettersen, E. F.; Goddard, T. D.; Huang, C. C.; Couch, G. S.; Greenblatt, D. M.; Meng, E. C.; Ferrin, T. E. UCSF Chimera-A visualization system for exploratory research and analysis. J. Comput. Chem. 2004, 25, 1605-1612.

(67) Peter M Hawkey, Roderic E Warren, David M Livermore, Cliodna A M McNulty, David A Enoch, Jonathan A Otter, A Peter R Wilson. Treatment of infections caused by multidrug-resistant Gram-negative bacteria: report of the British Society for Antimicrobial Chemotherapy/Healthcare Infection Society/British Infection Association Joint Working Party. Journal of Antimicrobial Chemotherapy, Volume 73, Issue suppl_3, 1 Mar. 2018, Pages iii2-iii78.

(68) Huttner A. and Gambillara V. The development and early clinical testing of the ExPEC4V conjugate vaccine against uropathogenic *Escherichia coli*. Clin Microbiol Infect. 2018 October; 24 (10): 1046-1050.

(69) Wong J E, Midtgaard S R, Gysel K, Thygesen M B, Sørensen K K, Jensen K J, Stougaard J, Thirup S, Blaise M An intermolecular binding mechanism involving multiple LysM domains mediates carbohydrate recognition by an endopeptidase.

(70) Rennell D, Bouvier S E, Hardy L W, Poteete A R. Systematic Mutation of Bacteriophage T4 Lysozyme. J MolBiol 1991; 222:67-88.

(71) Kuroki R, Weaver L H, Matthews B W. Structure-based design of a lysozyme with altered catalytic activity. Nat Struct Biol1995; 2:1007-1011 (72) Kuroki R, Weaver L H, Matthews B W. Structural basis of the conversion of T4 lysozyme into a transglycosidase by reengineering the active site. Proc Natl Acad Sci USA 1999; 96:8949-8954.

(73) Xu M, Arockiasamy A, Struck D K, Swanson S, Sacchettini J C, Young R. Disulfide isomerization after membrane release of its SAR domain activates P1 lysozyme. Science 2005; 307:113-117

(74) Maciejewska B, Żrubek K, Espaillat A, Wiśniewska M, Rembacz K P, Cava F, Dubin G, Drulis-Kawa Z Modular endolysin of *Burkholderia* AP3 phage has the largest lysozyme-like catalytic subunit discovered to date and no catalytic aspartate residue. Sci Rep. 2017 Nov. 6; 7 (1): 14501. doi: 10.1038/s41598-017-14797-9.
(75) Sun Q, Kuty G F, Arockiasamy A, Xu M, Young R, Sacchettini J C. Regulation of a muralytic enzyme by dynamic membrane topology. Nat Struct Mol Biol. 2009

November; 16 (11): 1192-4. doi: 10.1038/nsmb.1681. Epub 2009 Nov. 1.
(76) Masi, M., Réfregiers, M., Pos, K. et al. Mechanisms of envelope permeability and antibiotic influx and efflux in Gram-negative bacteria. Nat Microbiol 2, 17001 (2017).
(77) Düring, K., Porsch, P., Mahn, A., Brinkmann, O. and Gieffers, W. (1999) FEBS Lett. 449, 93-100.

---

The invention claimed is:

1. A chimeric protein consisting of amino acid sequence SEQ ID NO: 5.

2. The chimeric protein according to claim 1, wherein said chimeric protein has bacteriostatic or bactericidal activity against Gram-negative bacteria.

3. The chimeric protein according to claim 2, wherein said Gram-negative bacteria is one or more selected from the group consisting of the genus *Acinetobacter, Pseudomonas, Escherichia* and *Klebsiella.*

4. The chimeric protein according to claim 2, wherein said Gram-negative bacteria is one or more selected from the group consisting of *E. coli, K. pneumoniae, A. baumannii* and *P. aeruginosa.*

5. A polynucleotide comprising a nucleic acid molecule encoding the chimeric protein according to claim 1.

6. The polynucleotide according to claim 5, comprising: comprising a nucleic acid sequence consisting of SEQ ID NO: 9 .

7. A vector comprising the polynucleotide according to claim 5.

8. A host cell comprising the vector according to claim 7.

9. A method for producing the chimeric protein according to claim 1, wherein said method comprises:

i. introducing a vector comprising a polynucleotide comprising a nucleic acid molecule encoding the chimeric protein into an appropriate host cell;

ii. culturing the host cell under conditions suitable for the expression of said chimeric protein.

10. The method of claim 9, wherein said method further comprises after step (ii):

iii. isolating and/or purifying said chimeric protein.

11. A composition comprising the chimeric protein according to claim 1.

12. The composition according to claim 11, when said composition is a pharmaceutical composition and further comprises a pharmaceutically acceptable carrier, vehicle or excipient.

13. A kit comprising the chimeric protein according to claim 1.

14. A method for a prophylactic or therapeutic treatment of a Gram-negative bacterial infection in a subject, wherein said treatment comprises administering a therapeutically effective amount of the chimeric protein according to claim 1, or a pharmaceutical composition comprising the chimeric protein, to the subject, wherein said Gram-negative bacteria is one or more selected from the group consisting of the genus *Acinetobacter, Pseudomonas, Escherichia* and *Klebsiella.*

15. The method according to claim 14, wherein the administering is in combination with one or more antibiotics.

16. The method according to claim 15, wherein said antibiotic is a carbapenem.

17. The method according to claim 15, wherein said antibiotic is selected from imipenem and meropenem.

18. The method according to claim 14, wherein said Gram-negative bacteria is one or more selected from the group consisting of *E. coli, K. pneumoniae, A. baumannii* and *P. aeruginosa.*

19. An in vitro method of inhibiting the growth, reducing the population, or killing of Gram-negative bacteria, the method comprising contacting the bacteria with the chimeric protein according to claim 1 or a pharmaceutical composition comprising the chimeric protein, wherein said Gram negative bacteria is one or more selected from the group consisting of the genus *Acinetobacter, Pseudomonas, Escherichia* and *Klebsiella.*

20. The in vitro method according to claim 19, wherein said Gram-negative bacteria is one or more selected from the group consisting of *E. coli, K. pneumoniae, A. baumannii* and *P. aeruginosa.*

21. A method for disinfecting materials and/or surfaces, comprising contacting: the chimeric protein according to claim 1; or a composition comprising the chimeric protein with the materials and/or surfaces.

* * * * *

SEQUENCE LISTING

<160> NUMBER OF SEQ ID NOS: 9

<210> SEQ ID NO 1
<211> LENGTH: 163
<212> TYPE: PRT
<213> ORGANISM: Enterobacter phage Arya
<220> FEATURE:
<221> NAME/KEY: MISC_FEATURE
<222> LOCATION: (1)..(163)
<223> OTHER INFORMATION: Endolysin

<400> SEQUENCE: 1

```
Met Lys Thr Ser Pro Asn Gly Ile Ala Val Thr Lys Tyr Phe Glu Ser
1               5                   10                  15

Phe Glu Ala Arg Ala Tyr Pro Asp Pro Ala Thr Gly Gly Lys Pro Tyr
            20                  25                  30

Thr Ile Gly Phe Gly Thr Thr Val Tyr Pro Ser Gly Ala Pro Val Arg
        35                  40                  45

Leu Gly Asp Val Cys Thr Lys Glu Gln Ala Glu Lys Tyr Leu Gln Asn
    50                  55                  60

Asp Leu Ala Lys Phe Glu Lys Ile Val Ser Asp Ala Val Arg Val Pro
65                  70                  75                  80

Leu Asn Gln Gly Gln Phe Asp Ala Leu Val Ser Phe Thr Tyr Asn Leu
                85                  90                  95

Gly Pro Ala Asn Leu Arg Ser Ser Thr Leu Leu Lys Lys Leu Asn Ala
            100                 105                 110

Gly Asp Tyr Ala Gly Ala Ala Lys Glu Phe Pro Arg Trp Asn Arg Ala
        115                 120                 125

Asn Gly Lys Val Met Lys Gly Leu Thr Arg Arg Arg Ala Ala Glu Gln
    130                 135                 140

Cys Leu Phe Glu Gly Met Gly Gly Ala Ser Ala Ile Glu Arg Gly Val
145                 150                 155                 160

Ala Ala Ala
```

<210> SEQ ID NO 2
<211> LENGTH: 116
<212> TYPE: PRT
<213> ORGANISM: Bacillus amyloliquefaciens phage
<220> FEATURE:
<221> NAME/KEY: MISC_FEATURE
<222> LOCATION: (1)..(116)
<223> OTHER INFORMATION: cell permeability domain (D8)

<400> SEQUENCE: 2

```
Asn Ser Gly Thr Pro Lys Asn Val Ser Arg Gly Thr Ser Ser Thr Lys
1               5                   10                  15

Thr Thr Pro Lys Tyr Lys Val Lys Asn Gly Asp Asn Leu Thr Lys Ile
            20                  25                  30

Ala Lys Lys His Asn Thr Thr Val Ala Thr Leu Leu Lys Leu Asn Pro
        35                  40                  45
```

```
Gly Ile Lys Asp Pro Asn Met Ile Arg Val Gly Gln Thr Leu Asn Val
    50              55                  60

Thr Gly Ser Gly Gly Lys Thr His Lys Val Lys Ser Gly Asp Thr Leu
65              70                  75                  80

Ser Lys Ile Ala Val Asp Asn Lys Thr Thr Val Ser Lys Leu Met Asn
                85                  90                  95

Leu Asn Pro Glu Ile Thr Asn Pro Asn His Ile Lys Val Gly Gln Thr
            100                 105                 110

Ile Arg Leu Ser
        115

<210> SEQ ID NO 3
<211> LENGTH: 279
<212> TYPE: PRT
<213> ORGANISM: Artificial Sequence
<220> FEATURE:
<223> OTHER INFORMATION: Chimeric endolysin (SEQ ID NO:1 + SEQ ID NO:2)
<220> FEATURE:
<221> NAME/KEY: MISC_FEATURE
<222> LOCATION: (1)..(179)

<400> SEQUENCE: 3

Met Lys Thr Ser Pro Asn Gly Ile Ala Val Thr Lys Tyr Phe Glu Ser
1               5                   10                  15

Phe Glu Ala Arg Ala Tyr Pro Asp Pro Ala Thr Gly Gly Lys Pro Tyr
                20                  25                  30

Thr Ile Gly Phe Gly Thr Thr Val Tyr Pro Ser Gly Ala Pro Val Arg
            35                  40                  45

Leu Gly Asp Val Cys Thr Lys Glu Gln Ala Glu Lys Tyr Leu Gln Asn
    50                  55                  60

Asp Leu Ala Lys Phe Glu Lys Ile Val Ser Asp Ala Val Arg Val Pro
65                  70                  75                  80

Leu Asn Gln Gly Gln Phe Asp Ala Leu Val Ser Phe Thr Tyr Asn Leu
                85                  90                  95

Gly Pro Ala Asn Leu Arg Ser Ser Thr Leu Leu Lys Lys Leu Asn Ala
            100                 105                 110

Gly Asp Tyr Ala Gly Ala Ala Lys Glu Phe Pro Arg Trp Asn Arg Ala
            115                 120                 125

Asn Gly Lys Val Met Lys Gly Leu Thr Arg Arg Arg Ala Ala Glu Gln
    130                 135                 140

Cys Leu Phe Glu Gly Met Gly Gly Ala Ser Ala Ile Glu Arg Gly Val
145                 150                 155                 160

Ala Ala Ala Asn Ser Gly Thr Pro Lys Asn Val Ser Arg Gly Thr Ser
                165                 170                 175

Ser Thr Lys Thr Thr Pro Lys Tyr Lys Val Lys Asn Gly Asp Asn Leu
            180                 185                 190

Thr Lys Ile Ala Lys Lys His Asn Thr Thr Val Ala Thr Leu Leu Lys
        195                 200                 205

Leu Asn Pro Gly Ile Lys Asp Pro Asn Met Ile Arg Val Gly Gln Thr
    210                 215                 220

Leu Asn Val Thr Gly Ser Gly Gly Lys Thr His Lys Val Lys Ser Gly
225                 230                 235                 240

Asp Thr Leu Ser Lys Ile Ala Val Asp Asn Lys Thr Thr Val Ser Lys
            245                 250                 255

Leu Met Asn Leu Asn Pro Glu Ile Thr Asn Pro Asn His Ile Lys Val
            260                 265                 270
```

-continued

```
Gly Gln Thr Ile Arg Leu Ser
        275

<210> SEQ ID NO 4
<211> LENGTH: 6
<212> TYPE: PRT
<213> ORGANISM: Artificial Sequence
<220> FEATURE:
<223> OTHER INFORMATION: thrombin cutting site
<220> FEATURE:
<221> NAME/KEY: MISC_FEATURE
<222> LOCATION: (1)..(6)

<400> SEQUENCE: 4

Leu Val Pro Arg Gly Ser
1               5

<210> SEQ ID NO 5
<211> LENGTH: 329
<212> TYPE: PRT
<213> ORGANISM: Artificial Sequence
<220> FEATURE:
<223> OTHER INFORMATION: chimeric endolysin (IKB206tags)
<220> FEATURE:
<221> NAME/KEY: MISC_FEATURE
<222> LOCATION: (1)..(329)

<400> SEQUENCE: 5

Met Lys Glu Thr Ala Ala Ala Lys Phe Glu Arg Gln His Met Asp Ser
1               5                   10                  15

Pro Asp Leu Gly Thr Leu Val Pro Arg Gly Ser Met Ala Ile Ser Asp
            20                  25                  30

Pro Met Lys Thr Ser Pro Asn Gly Ile Ala Val Thr Lys Tyr Phe Glu
        35                  40                  45

Ser Phe Glu Ala Arg Ala Tyr Pro Asp Pro Ala Thr Gly Gly Lys Pro
    50                  55                  60

Tyr Thr Ile Gly Phe Gly Thr Thr Val Tyr Pro Ser Gly Ala Pro Val
65                  70                  75                  80

Arg Leu Gly Asp Val Cys Thr Lys Glu Gln Ala Glu Lys Tyr Leu Gln
                85                  90                  95

Asn Asp Leu Ala Lys Phe Glu Lys Ile Val Ser Asp Ala Val Arg Val
            100                 105                 110

Pro Leu Asn Gln Gly Gln Phe Asp Ala Leu Val Ser Phe Thr Tyr Asn
        115                 120                 125

Leu Gly Pro Ala Asn Leu Arg Ser Ser Thr Leu Leu Lys Lys Leu Asn
    130                 135                 140

Ala Gly Asp Tyr Ala Gly Ala Ala Lys Glu Phe Pro Arg Trp Asn Arg
145                 150                 155                 160

Ala Asn Gly Lys Val Met Lys Gly Leu Thr Arg Arg Arg Ala Ala Glu
                165                 170                 175

Gln Cys Leu Phe Glu Gly Met Gly Gly Ala Ser Ala Ile Glu Arg Gly
            180                 185                 190

Val Ala Ala Ala Asn Ser Gly Thr Pro Lys Asn Val Ser Arg Gly Thr
        195                 200                 205

Ser Ser Thr Lys Thr Thr Pro Lys Tyr Lys Val Lys Asn Gly Asp Asn
    210                 215                 220

Leu Thr Lys Ile Ala Lys Lys His Asn Thr Thr Val Ala Thr Leu Leu
225                 230                 235                 240

Lys Leu Asn Pro Gly Ile Lys Asp Pro Asn Met Ile Arg Val Gly Gln
                245                 250                 255
```

-continued

```
Thr Leu Asn Val Thr Gly Ser Gly Gly Lys Thr His Lys Val Lys Ser
            260                 265                 270

Gly Asp Thr Leu Ser Lys Ile Ala Val Asp Asn Lys Thr Thr Val Ser
        275                 280                 285

Lys Leu Met Asn Leu Asn Pro Glu Ile Thr Asn Pro Asn His Ile Lys
    290                 295                 300

Val Gly Gln Thr Ile Arg Leu Ser Leu Gly Thr Leu Val Pro Arg Gly
305                 310                 315                 320

Ser Leu Glu His His His His His His
            325
```

```
<210> SEQ ID NO 6
<211> LENGTH: 489
<212> TYPE: DNA
<213> ORGANISM: Artificial Sequence
<220> FEATURE:
<223> OTHER INFORMATION: polynucleotide encoding SEQ ID NO:1
<220> FEATURE:
<221> NAME/KEY: misc_feature
<222> LOCATION: (1)..(489)

<400> SEQUENCE: 6
atgaaaacct ctccaaatgg tatcgccgtt accaagtact tcgaatcatt tgaagcccgc       60
gcataccctg accccgccac tggcggtaaa ccatacacga ttggcttcgg aaccactgtc      120
tacccgtctg gcgcacccgt ccgtttaggg gatgtgtgta cgaaagaaca ggccgagaaa      180
tatttacaaa atgacttggc gaaattcgag aagattgtat ctgacgcagt gcgcgttccc      240
cttaatcaag gtcagtttga cgcgttagtg tcatttacgt ataacttagg acccgccaat      300
ttgcgcagca gtaccctgtt aaaaaagttg aacgctgggg actatgcggg ggccgctaaa      360
gagtttccgc gttggaaccg tgcaaacggt aaagtgatga aaggtttgac acgtcgccgc      420
gcggcagaac aatgtttgtt tgaagggatg ggaggcgcga gcgcgattga acgtggtgta      480
gccgctgca                                                             489
```

```
<210> SEQ ID NO 7
<211> LENGTH: 348
<212> TYPE: DNA
<213> ORGANISM: Artificial Sequence
<220> FEATURE:
<223> OTHER INFORMATION: Polynucleotide encoding a polypeptide of SEQ ID
      NO:2
<220> FEATURE:
<221> NAME/KEY: misc_feature
<222> LOCATION: (1)..(348)

<400> SEQUENCE: 7
aacagtggga caccaaagaa tgtttcccgc ggaacctcgt ccacgaagac aacacctaag       60
tataaggtaa aaaatggtga caacttaact aaaatcgcga agaaacataa tactacagta      120
gcgacattgc tgaaacttaa tccagggatc aaagacccca acatgattcg tgtagggcag      180
actttaaatg ttacagggtc cggtgggaaa actcataaag tcaagtcggg tgacacactg      240
agtaaaatcg cagttgataa taagacgact gttagcaagt tgatgaatct taacccggaa      300
atcactaatc ctaaccatat caaagtcggc cagacaatcc gtttgagc                   348
```

```
<210> SEQ ID NO 8
<211> LENGTH: 837
<212> TYPE: DNA
<213> ORGANISM: Artificial Sequence
<220> FEATURE:
```

-continued

```
<223> OTHER INFORMATION: Polynucleotide sequence encoding SEQ ID NO:3
<220> FEATURE:
<221> NAME/KEY: misc_feature
<222> LOCATION: (1)..(837)

<400> SEQUENCE: 8
atgaaaacct ctccaaatgg tatcgccgtt accaagtact tcgaatcatt tgaagcccgc        60 gcatacccctg accccgccac tggcggtaaa ccatacacga ttggcttcgg aaccactgtc       120
tacccgtctg gcgcacccgt ccgtttaggg gatgtgtgta cgaaagaaca ggccgagaaa       180
tatttacaaa atgacttggc gaaattcgag aagattgtat ctgacgcagt gcgcgttccc       240
cttaatcaag gtcagtttga cgcgttagtg tcatttacgt ataacttagg acccgccaat       300
ttgcgcagca gtaccctgtt aaaaaagttg aacgctgggg actatgcggg ggccgctaaa       360
gagtttccgc gttggaaccg tgcaaacggt aaagtgatga aggtttgac acgtcgccgc        420 gcggcagaac aatgtttgtt tgaagggatg ggaggcgcga gcgcgattga acgtggtgta       480
gccgctgcaa acagtgggac accaaagaat gtttcccgcg gaacctcgtc cacgaagaca       540
acacctaagt ataaggtaaa aaatggtgac aacttaacta aaatcgcgaa gaaacataat       600
actacagtag cgacattgct gaaacttaat ccagggatca aagaccccaa catgattcgt       660
gtagggcaga ctttaaatgt tacagggtcc ggtgggaaaa ctcataaagt caagtcgggt       720
gacacactga gtaaaatcgc agttgataat aagacgactg ttagcaagtt gatgaatctt       780
aacccggaaa tcactaatcc taaccatatc aaagtcggcc agacaatccg tttgagc          837

<210> SEQ ID NO 9
<211> LENGTH: 987
<212> TYPE: DNA
<213> ORGANISM: Artificial Sequence
<220> FEATURE:
<223> OTHER INFORMATION: polynucleotide encoding SEQ ID NO:5
<220> FEATURE:
<221> NAME/KEY: misc_feature
<222> LOCATION: (1)..(987)

<400> SEQUENCE: 9
atgaaagaaa ccgctgctgc taaattcgaa cgccagcaca tggacagccc agatctgggt        60
accctggtgc cacgcggttc catggcgata tcggatccga tgaaaacctc tccaaatggt       120
atcgccgtta ccaagtactt cgaatcattt gaagcccgcg catacctga ccccgccact        180 ggcggtaaac catacacgat tggcttcgga accactgtct acccgtctgg cgcacccgtc       240
cgtttagggg atgtgtgtac gaaagaacag gccgagaaat atttacaaaa tgacttggcg       300
aaattcgaga agattgtatc tgacgcagtg cgcgttcccc ttaatcaagg tcagtttgac       360
gcgttagtgt catttacgta taacttagga cccgccaatt tgcgcagcag taccctgtta       420
aaaaagttga acgctgggga ctatgcgggg gccgctaaag agtttccgcg ttggaaccgt       480
gcaaacggta aagtgatgaa aggtttgaca cgtcgccgcg cggcagaaca atgtttgttt       540
gaagggatgg gaggcgcgag cgcgattgaa cgtggtgtag ccgctgcaaa cagtgggaca       600
ccaaagaatg tttcccgcgg aacctcgtcc acgaagacaa cacctaagta taaggtaaaa       660
aatggtgaca acttaactaa aatcgcgaag aaacataata ctacagtagc gacattgctg       720
aaacttaatc cagggatcaa agaccccaac atgattcgtg tagggcagac tttaaatgtt       780
```

-continued

```
acagggtccg gtgggaaaac tcataaagtc aagtcgggtg acacactgag taaaatcgca     840
gttgataata agacgactgt tagcaagttg atgaatctta acccggaaat cactaatcct     900
aaccatatca aagtcggcca gacaatccgt ttgagcctgg gtaccctggt gccacgcggt     960
tccctcgagc accaccacca ccaccac                                        987
```